(12) United States Patent
Dixon et al.

(10) Patent No.: US 11,011,267 B2
(45) Date of Patent: *May 18, 2021

(54) BED/ROOM/PATIENT ASSOCIATION SYSTEMS AND METHODS

(71) Applicant: Hill-Rom Services, Inc., Batesville, IN (US)

(72) Inventors: Steven A. Dixon, Cincinnati, OH (US); Keith A. Huster, Sunman, IN (US); Michael A. Hood, Batesville, IN (US); James M. Allen, Batesville, IN (US); John D. Christie, Batesville, IN (US); Jack Barney Sing, Batesville, IN (US); Dan R. Tallent, Hope, IN (US); Umesh J. Rajani, Cary, NC (US); Clay G. Owsley, Pittsboro, IN (US); Thomas F. Heil, Batesville, IN (US); Richard Joseph Schuman, Sr., Cary, NC (US); Timothy D. Wildman, Metamora, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 589 days.

This patent is subject to a terminal disclaimer.

(21) Appl. No.: 15/784,693

(22) Filed: Oct. 16, 2017

(65) Prior Publication Data
US 2018/0039743 A1 Feb. 8, 2018

Related U.S. Application Data

(63) Continuation of application No. 14/487,279, filed on Sep. 16, 2014, now Pat. No. 9,830,424.

(Continued)

(51) Int. Cl.
*A61G 7/05* (2006.01)
*G16H 40/20* (2018.01)
*G16H 40/67* (2018.01)

(52) U.S. Cl.
CPC ............... *G16H 40/20* (2018.01); *A61G 7/05* (2013.01); *G16H 40/67* (2018.01)

(58) Field of Classification Search
CPC ...... B60T 17/22; B60T 7/085; G06F 19/3406; G06F 19/3462
See application file for complete search history.

(56) References Cited

U.S. PATENT DOCUMENTS

| 1,758,546 A | 5/1930 | Wartmann |
| 2,330,356 A | 9/1943 | Belliveau |

(Continued)

FOREIGN PATENT DOCUMENTS

| EP | 2031535 A2 | 3/2009 |
| WO | 2006/105269 A1 | 10/2006 |

OTHER PUBLICATIONS

Reference Manual, Laird WB45NBT, Version 1.0, revised Aug. 20, 2013, 37 pages.

(Continued)

*Primary Examiner* — Reginald R Reyes
(74) *Attorney, Agent, or Firm* — Barnes & Thornburg LLP

(57) ABSTRACT

Systems and methods of associating beds and/or rooms and/or patients are provided. One system and method involves using a signature of emitted light to determine a location of a patient bed in a healthcare facility. Another system and method involves reading a bar code from an array of redundant bar codes. Still another system and method involves manually entering location information on a graphical user interface of a patient bed for subsequent (Continued)

transmission. A further system and method involves sending bed ID and location ID along parallel paths from two independent circuits on a patient bed for receipt by two different transceivers and ultimately by two different remote computers that cooperate to associate the bed ID with the location ID. Still a further system and method involves using circuitry on a bed to mutate a received location ID and a bed ID into a single unique mutated ID such as by adding the location ID and bed ID and then performing a hashing operation.

19 Claims, 28 Drawing Sheets

Related U.S. Application Data

(60) Provisional application No. 61/879,399, filed on Sep. 18, 2013.

(56) References Cited

U.S. PATENT DOCUMENTS

| | | |
|---|---|---|
| 2,335,524 A | 11/1943 | Lomax |
| 2,736,888 A | 2/1956 | McLain |
| 2,896,021 A | 7/1959 | Philipps |
| D188,659 S | 8/1960 | Locke |
| 3,054,201 A | 9/1962 | Burns |
| 3,098,220 A | 7/1963 | De Graaf |
| 3,181,141 A | 4/1965 | Villiers |
| 3,439,320 A | 4/1969 | Ward |
| 3,478,344 A | 11/1969 | Schwitzgebel et al. |
| 3,553,383 A | 1/1971 | Rochtus |
| 3,599,199 A | 8/1971 | Bunting |
| 3,599,200 A | 8/1971 | Bunting |
| 3,659,586 A | 5/1972 | Johns et al. |
| 3,696,384 A | 10/1972 | Lester |
| 3,739,329 A | 6/1973 | Lester |
| 3,767,859 A | 10/1973 | Doering et al. |
| 3,805,227 A | 4/1974 | Lester |
| 3,805,265 A | 4/1974 | Lester |
| 3,810,136 A | 5/1974 | Lang et al. |
| 3,913,153 A | 10/1975 | Adams et al. |
| 3,973,200 A | 8/1976 | Åkerberg |
| 4,052,567 A | 10/1977 | MacKay |
| 4,067,005 A | 1/1978 | Levy et al. |
| 4,126,768 A | 11/1978 | Grenzow |
| 4,150,284 A | 4/1979 | Trenkler et al. |
| 4,151,407 A | 4/1979 | McBride et al. |
| 4,183,015 A | 1/1980 | Drew et al. |
| 4,216,462 A | 8/1980 | McGrath et al. |
| 4,224,596 A | 9/1980 | Knickel |
| 4,225,953 A | 9/1980 | Simon et al. |
| 4,228,426 A | 10/1980 | Roberts |
| 4,237,344 A | 12/1980 | Moore |
| 4,264,982 A | 4/1981 | Sakarya |
| 4,275,385 A | 6/1981 | White |
| 4,279,433 A | 7/1981 | Petaja |
| 4,298,863 A | 11/1981 | Natitus et al. |
| 4,331,953 A | 5/1982 | Blevins et al. |
| 4,356,475 A | 10/1982 | Neumann et al. |
| 4,363,029 A | 12/1982 | Piliavin et al. |
| 4,363,137 A | 12/1982 | Salisbury |
| 4,418,334 A | 11/1983 | Burnett |
| 4,455,548 A | 6/1984 | Burnett |
| 4,489,387 A | 12/1984 | Lamb et al. |
| 4,491,947 A | 1/1985 | Frank |
| 4,495,495 A | 1/1985 | Ormanns et al. |
| 4,495,496 A | 1/1985 | Miller, III |
| 4,532,419 A | 7/1985 | Takeda |
| 4,539,560 A | 9/1985 | Fleck et al. |
| 4,556,932 A | 12/1985 | Lehrer et al. |
| 4,577,060 A | 3/1986 | Webb et al. |
| 4,577,185 A | 3/1986 | Andersen |
| 4,578,671 A | 3/1986 | Flowers |
| 4,593,273 A | 6/1986 | Narcisse |
| 4,598,275 A | 7/1986 | Ross et al. |
| 4,601,064 A | 7/1986 | Shipley |
| 4,638,313 A | 1/1987 | Sherwood, Jr. et al. |
| 4,648,123 A | 3/1987 | Schrock |
| 4,649,385 A | 3/1987 | Aires et al. |
| 4,654,629 A | 3/1987 | Bezos et al. |
| 4,663,625 A | 5/1987 | Yewen |
| 4,677,599 A | 6/1987 | Obayashi et al. |
| 4,680,790 A | 7/1987 | Packard et al. |
| 4,688,026 A | 8/1987 | Scribner et al. |
| 4,699,149 A | 10/1987 | Rice |
| 4,706,689 A | 11/1987 | Man |
| 4,709,330 A | 11/1987 | Yokoi et al. |
| 4,740,788 A | 4/1988 | Konneker |
| 4,748,668 A | 5/1988 | Shamir et al. |
| 4,752,951 A | 6/1988 | Konneker |
| 4,792,798 A | 12/1988 | Wilowski |
| 4,795,905 A | 1/1989 | Zierhut |
| 4,803,599 A | 2/1989 | Trine et al. |
| 4,814,751 A | 3/1989 | Hawkins et al. |
| 4,833,452 A | 5/1989 | Currier |
| 4,833,467 A | 5/1989 | Kobayashi et al. |
| 4,835,372 A | 5/1989 | Gombrich et al. |
| 4,837,568 A | 6/1989 | Snaper |
| 4,839,975 A | 6/1989 | Elmer |
| 4,843,640 A | 6/1989 | Juengel |
| 4,849,615 A | 7/1989 | Mallet |
| 4,853,692 A | 8/1989 | Wolk et al. |
| 4,857,716 A | 8/1989 | Gombrich et al. |
| 4,862,088 A | 8/1989 | Etienne et al. |
| 4,871,997 A | 10/1989 | Adriaenssens et al. |
| 4,899,135 A | 2/1990 | Ghahariiran |
| 4,947,152 A | 8/1990 | Hodges |
| 4,955,000 A | 9/1990 | Nastrom |
| 4,958,645 A | 9/1990 | Cadell et al. |
| 4,967,195 A | 10/1990 | Shipley |
| 4,980,679 A | 12/1990 | Klaubert |
| 4,990,892 A | 2/1991 | Guest et al. |
| 4,998,095 A | 3/1991 | Shields |
| 4,998,939 A | 3/1991 | Potthast et al. |
| 5,005,005 A | 4/1991 | Brossia et al. |
| 5,006,830 A | 4/1991 | Merritt |
| 5,014,040 A | 5/1991 | Weaver et al. |
| 5,027,314 A | 6/1991 | Linwood et al. |
| 5,031,156 A | 7/1991 | Watts et al. |
| 5,041,086 A | 8/1991 | Koenig et al. |
| 5,062,151 A | 10/1991 | Shipley |
| 5,065,154 A | 11/1991 | Kaiser et al. |
| 5,079,808 A | 1/1992 | Brown |
| 5,086,290 A | 2/1992 | Murray et al. |
| 5,103,108 A | 4/1992 | Crimmins |
| 5,119,104 A | 6/1992 | Heller |
| 5,124,991 A | 6/1992 | Allen |
| 5,131,040 A | 7/1992 | Knapczyk |
| 5,137,033 A | 8/1992 | Norton |
| 5,153,584 A | 10/1992 | Engira |
| 5,164,886 A | 11/1992 | Chang |
| 5,164,985 A | 11/1992 | Nysen et al. |
| 5,217,003 A | 6/1993 | Wilk |
| 5,231,273 A | 7/1993 | Caswell et al. |
| 5,266,944 A | 11/1993 | Carroll et al. |
| 5,274,311 A | 12/1993 | Littlejohn et al. |
| 5,276,496 A | 1/1994 | Heller et al. |
| 5,283,781 A | 2/1994 | Buda et al. |
| 5,291,399 A | 3/1994 | Chaco |
| 5,317,309 A | 5/1994 | Vercellotti et al. |
| 5,319,191 A | 6/1994 | Crimmins |
| 5,319,355 A | 6/1994 | Russek |
| 5,319,363 A | 6/1994 | Welch et al. |
| 5,334,851 A | 8/1994 | Good et al. |
| 5,339,259 A | 8/1994 | Puma et al. |
| 5,341,126 A | 8/1994 | Boykin |
| 5,351,149 A | 9/1994 | Crimmins |
| 5,355,222 A | 10/1994 | Heller et al. |
| 5,357,254 A | 10/1994 | Kah, Jr. |
| 5,363,425 A | 11/1994 | Mufti et al. |
| 5,375,604 A | 12/1994 | Kelly et al. |

(56) References Cited

U.S. PATENT DOCUMENTS

| | | |
|---|---|---|
| 5,387,993 A | 2/1995 | Heller et al. |
| 5,396,224 A | 3/1995 | Dukes et al. |
| 5,396,227 A | 3/1995 | Carroll et al. |
| 5,402,469 A | 3/1995 | Hopper et al. |
| 5,416,695 A | 5/1995 | Stutman et al. |
| 5,421,177 A | 6/1995 | Sieber et al. |
| 5,434,775 A | 7/1995 | Sims et al. |
| 5,446,678 A | 8/1995 | Saltzstein et al. |
| RE35,035 E | 9/1995 | Shipley |
| 5,455,560 A | 10/1995 | Owen |
| 5,455,851 A | 10/1995 | Chaco et al. |
| 5,458,123 A | 10/1995 | Unger |
| 5,461,390 A | 10/1995 | Hoshen |
| 5,465,082 A | 11/1995 | Chaco |
| 5,471,404 A | 11/1995 | Mazer |
| 5,475,367 A | 12/1995 | Prevost |
| 5,482,036 A | 1/1996 | Diab et al. |
| 5,515,426 A | 5/1996 | Yacenda et al. |
| 5,519,380 A | 5/1996 | Edwards |
| 5,534,851 A | 7/1996 | Russek |
| 5,534,876 A | 7/1996 | Erickson et al. |
| 5,537,459 A | 7/1996 | Price et al. |
| 5,548,637 A | 8/1996 | Heller et al. |
| 5,549,113 A | 8/1996 | Halleck et al. |
| 5,561,412 A | 10/1996 | Novak et al. |
| 5,568,119 A | 10/1996 | Schipper et al. |
| 5,572,195 A | 11/1996 | Heller et al. |
| 5,576,952 A | 11/1996 | Stutman et al. |
| 5,579,001 A | 11/1996 | Dempsey et al. |
| 5,588,005 A | 12/1996 | Ali et al. |
| 5,594,786 A | 1/1997 | Chaco et al. |
| 5,621,388 A | 4/1997 | Sherburne et al. |
| 5,627,524 A | 5/1997 | Fredrickson et al. |
| 5,629,678 A | 5/1997 | Gargano et al. |
| 5,633,742 A | 5/1997 | Shipley |
| 5,635,907 A | 6/1997 | Bernard et al. |
| 5,636,245 A | 6/1997 | Ernst et al. |
| 5,639,393 A | 6/1997 | Veltum et al. |
| 5,640,002 A | 6/1997 | Ruppert et al. |
| 5,640,146 A | 6/1997 | Campana, Jr. |
| 5,640,953 A | 6/1997 | Bishop et al. |
| 5,650,769 A | 7/1997 | Campana, Jr. |
| 5,650,770 A | 7/1997 | Schlager et al. |
| 5,661,457 A | 8/1997 | Ghaffari et al. |
| 5,664,035 A | 9/1997 | Tsuji et al. |
| 5,664,270 A | 9/1997 | Bell et al. |
| 5,682,139 A | 10/1997 | Pradeep et al. |
| 5,686,888 A | 11/1997 | Welles, II et al. |
| 5,686,902 A | 11/1997 | Reis et al. |
| 5,687,109 A | 11/1997 | Protigal et al. |
| 5,687,735 A | 11/1997 | Dempsey et al. |
| 5,689,229 A | 11/1997 | Chaco et al. |
| 5,691,980 A | 11/1997 | Welles, II et al. |
| 5,699,038 A | 12/1997 | Ulrich et al. |
| 5,705,980 A | 1/1998 | Shapiro |
| 5,708,421 A | 1/1998 | Boyd |
| 5,708,423 A | 1/1998 | Ghaffari et al. |
| 5,713,856 A | 2/1998 | Eggers et al. |
| 5,719,761 A | 2/1998 | Gatti et al. |
| 5,731,757 A | 3/1998 | Layson, Jr. |
| 5,742,237 A | 4/1998 | Bledsoe |
| 5,742,238 A | 4/1998 | Fox |
| 5,745,037 A | 4/1998 | Guthrie et al. |
| 5,748,148 A | 5/1998 | Heiser et al. |
| 5,751,246 A | 5/1998 | Hertel |
| 5,752,917 A | 5/1998 | Fuchs |
| 5,754,125 A | 5/1998 | Pearce |
| 5,760,704 A | 6/1998 | Barton et al. |
| 5,764,162 A | 6/1998 | Ehrlich |
| 5,767,788 A | 6/1998 | Ness |
| 5,767,791 A | 6/1998 | Stoop et al. |
| 5,771,003 A | 6/1998 | Seymour |
| 5,776,056 A | 7/1998 | Bu et al. |
| 5,781,442 A | 7/1998 | Engleson et al. |
| 5,781,632 A | 7/1998 | Odom |
| 5,792,063 A | 8/1998 | Danielsson et al. |
| 5,793,290 A | 8/1998 | Eagleson et al. |
| 5,808,564 A | 9/1998 | Simms et al. |
| 5,812,056 A | 9/1998 | Law |
| 5,822,418 A | 10/1998 | Yacenda et al. |
| 5,822,544 A | 10/1998 | Chaco et al. |
| 5,828,306 A | 10/1998 | Curran |
| 5,831,533 A | 11/1998 | Kanno |
| 5,838,223 A | 11/1998 | Gallant et al. |
| 5,838,472 A | 11/1998 | Welch et al. |
| 5,844,488 A | 12/1998 | Musick |
| 5,867,821 A | 2/1999 | Ballantyne et al. |
| 5,877,675 A | 3/1999 | Rebstock et al. |
| 5,878,143 A | 3/1999 | Moore |
| 5,897,506 A | 4/1999 | Cohn |
| 5,898,459 A | 4/1999 | Smith et al. |
| 5,910,776 A | 6/1999 | Black |
| 5,933,488 A | 8/1999 | Marcus et al. |
| 5,936,527 A | 8/1999 | Isaacman et al. |
| 5,936,539 A | 8/1999 | Fuchs |
| 5,942,986 A | 8/1999 | Shabot et al. |
| 5,944,659 A | 8/1999 | Flach et al. |
| 5,956,660 A | 9/1999 | Neumann |
| 5,963,133 A | 10/1999 | Monjo |
| 5,963,137 A | 10/1999 | Waters, Sr. |
| 5,973,598 A | 10/1999 | Beigel |
| 5,974,389 A | 10/1999 | Clark et al. |
| 5,991,728 A | 11/1999 | DeBusk et al. |
| 5,995,937 A | 11/1999 | DeBusk et al. |
| 5,997,476 A | 12/1999 | Brown |
| RE36,530 E | 1/2000 | Heller et al. |
| 6,014,633 A | 1/2000 | DeBusk et al. |
| 6,026,818 A | 2/2000 | Blair et al. |
| 6,028,514 A | 2/2000 | Lemelson et al. |
| 6,031,458 A | 2/2000 | Jacobsen et al. |
| 6,031,459 A | 2/2000 | Lake |
| 6,031,460 A | 2/2000 | Banks |
| 6,034,603 A | 3/2000 | Steeves |
| 6,034,622 A | 3/2000 | Levine |
| 6,037,879 A | 3/2000 | Tuttle |
| 6,040,773 A | 3/2000 | Vega et al. |
| 6,049,278 A | 4/2000 | Guthrie et al. |
| 6,049,290 A | 4/2000 | Halstead |
| 6,052,710 A | 4/2000 | Saliba et al. |
| 6,054,927 A | 4/2000 | Brickell |
| 6,055,487 A | 4/2000 | Margery et al. |
| 6,055,506 A | 4/2000 | Frasca, Jr. |
| 6,057,758 A | 5/2000 | Dempsey et al. |
| 6,057,782 A | 5/2000 | Koenig |
| 6,067,019 A | 5/2000 | Scott |
| 6,069,555 A | 5/2000 | Skitek et al. |
| 6,069,564 A | 5/2000 | Hatano et al. |
| 6,069,570 A | 5/2000 | Herring |
| 6,075,707 A | 6/2000 | Ferguson et al. |
| 6,076,166 A | 6/2000 | Moshfeghi et al. |
| 6,078,251 A | 6/2000 | Landt et al. |
| 6,078,259 A | 6/2000 | Brady et al. |
| 6,078,261 A | 6/2000 | Davsko |
| 6,078,631 A | 6/2000 | Yabe et al. |
| RE36,791 E | 7/2000 | Heller |
| 6,084,512 A | 7/2000 | Elberty et al. |
| 6,085,069 A | 7/2000 | Sharpe |
| 6,085,493 A | 7/2000 | DeBusk et al. |
| 6,088,362 A | 7/2000 | Turnbull et al. |
| 6,091,332 A | 7/2000 | Eberhardt et al. |
| 6,091,530 A | 7/2000 | Duckworth |
| 6,093,146 A | 7/2000 | Filangeri |
| 6,097,301 A | 8/2000 | Tuttle |
| 6,097,308 A | 8/2000 | Albert et al. |
| 6,100,804 A | 8/2000 | Brady et al. |
| 6,101,390 A | 8/2000 | Jayaraman et al. |
| 6,104,295 A | 8/2000 | Gaisser et al. |
| 6,104,311 A | 8/2000 | Lastinger |
| 6,111,506 A | 8/2000 | Yap et al. |
| 6,114,962 A | 9/2000 | Wiklof et al. |
| 6,118,379 A | 9/2000 | Kodukula et al. |
| 6,127,928 A | 10/2000 | Issacman et al. |
| 6,130,612 A | 10/2000 | Castellano et al. |
| 6,133,832 A | 10/2000 | Winder et al. |

(56) References Cited

U.S. PATENT DOCUMENTS

| | | |
|---|---|---|
| 6,133,837 A | 10/2000 | Riley |
| 6,137,411 A | 10/2000 | Tyren |
| 6,137,412 A | 10/2000 | Herzer |
| 6,137,414 A | 10/2000 | Federman |
| 6,144,301 A | 11/2000 | Frieden |
| 6,144,303 A | 11/2000 | Federman |
| 6,147,592 A | 11/2000 | Ulrich et al. |
| 6,148,291 A | 11/2000 | Radican |
| 6,150,948 A | 11/2000 | Watkins |
| 6,150,950 A | 11/2000 | Shen Liu |
| 6,154,135 A | 11/2000 | Kane et al. |
| 6,154,139 A | 11/2000 | Heller |
| 6,157,302 A | 12/2000 | Kolton et al. |
| 6,160,881 A | 12/2000 | Beyda et al. |
| 6,169,484 B1 | 1/2001 | Schuchman et al. |
| 6,169,485 B1 | 1/2001 | Campana, Jr. |
| 6,177,861 B1 | 1/2001 | MacLellan et al. |
| 6,183,417 B1 | 2/2001 | Geheb et al. |
| 6,203,495 B1 | 3/2001 | Bardy |
| 6,204,765 B1 | 3/2001 | Brady et al. |
| 6,204,813 B1 | 3/2001 | Wadell et al. |
| 6,208,250 B1 | 3/2001 | Dixon et al. |
| 6,211,666 B1 | 4/2001 | Acker |
| 6,211,781 B1 | 4/2001 | McDonald |
| 6,211,796 B1 | 4/2001 | Toms et al. |
| 6,215,389 B1 | 4/2001 | Schmidt |
| 6,222,440 B1 | 4/2001 | Heller |
| 6,228,029 B1 | 5/2001 | Eccardt et al. |
| 6,236,319 B1 | 5/2001 | Pitzer et al. |
| 6,241,668 B1 | 6/2001 | Herzog |
| 6,249,234 B1 | 6/2001 | Ely et al. |
| 6,259,355 B1 | 7/2001 | Chaco et al. |
| 6,262,666 B1 | 7/2001 | Lodichand |
| 6,264,614 B1 | 7/2001 | Albert et al. |
| 6,268,797 B1 | 7/2001 | Berube et al. |
| 6,275,153 B1 | 8/2001 | Brooks |
| 6,279,183 B1 | 8/2001 | Kummer et al. |
| 6,280,409 B1 | 8/2001 | Stone et al. |
| 6,285,742 B1 | 9/2001 | Haumann et al. |
| 6,287,253 B1 | 9/2001 | Ortega et al. |
| 6,289,237 B1 | 9/2001 | Mickle et al. |
| 6,293,699 B1 | 9/2001 | Bailey et al. |
| 6,294,953 B1 | 9/2001 | Steeves |
| 6,302,844 B1 | 10/2001 | Walker et al. |
| 6,314,556 B1 | 11/2001 | DeBusk et al. |
| 6,320,510 B2 | 11/2001 | Menkedick et al. |
| 6,333,690 B1 | 12/2001 | Nelson et al. |
| 6,343,064 B1 | 1/2002 | Jabbarnezhad |
| 6,344,794 B1 | 2/2002 | Ulrich et al. |
| 6,348,777 B1 | 2/2002 | Brown et al. |
| 6,353,413 B1 | 3/2002 | White et al. |
| 6,362,725 B1 | 3/2002 | Ulrich et al. |
| 6,364,834 B1 | 4/2002 | Reuss et al. |
| 6,398,727 B1 | 6/2002 | Bui et al. |
| 6,400,956 B1 | 6/2002 | Richton |
| 6,406,426 B1 | 6/2002 | Reuss et al. |
| 6,407,335 B1 | 6/2002 | Franklin-Lees et al. |
| 6,412,980 B1 | 7/2002 | Lounsberry et al. |
| 6,416,471 B1 | 7/2002 | Kumar et al. |
| 6,418,416 B1 | 7/2002 | Rosenberg et al. |
| 6,421,649 B1 | 7/2002 | Rattner |
| 6,424,264 B1 | 7/2002 | Giraldin et al. |
| 6,439,769 B1 | 8/2002 | Polkus et al. |
| 6,441,742 B1 | 8/2002 | Lovely et al. |
| 6,442,290 B1 | 8/2002 | Ellis et al. |
| 6,445,299 B1 | 9/2002 | Rojas, Jr. |
| 6,450,956 B1 | 9/2002 | Rappaport et al. |
| 6,462,656 B2 | 10/2002 | Ulrich et al. |
| 6,486,792 B1 | 11/2002 | Moster et al. |
| 6,486,794 B1 | 11/2002 | Calistro et al. |
| 6,493,568 B1 | 12/2002 | Bell et al. |
| 6,494,831 B1 | 12/2002 | Koritzinsky |
| 6,510,344 B1 | 1/2003 | Halpern |
| 6,516,324 B1 | 2/2003 | Jones et al. |
| 6,526,310 B1 | 2/2003 | Carter et al. |
| 6,529,164 B1 | 3/2003 | Carter |
| 6,533,453 B1 | 3/2003 | Heidsieck et al. |
| 6,535,576 B2 | 3/2003 | Vafi et al. |
| 6,544,174 B2 | 4/2003 | West et al. |
| 6,551,243 B2 | 4/2003 | Bocionek et al. |
| 6,553,106 B1 | 4/2003 | Gould et al. |
| 6,554,174 B1 | 4/2003 | Aceves |
| 6,556,630 B1 | 4/2003 | Brinsfield et al. |
| 6,560,274 B1 | 5/2003 | Leitgeb et al. |
| 6,572,556 B2 | 6/2003 | Stoycos et al. |
| 6,575,901 B2 | 6/2003 | Stoycos et al. |
| 6,581,204 B2 | 6/2003 | DeBusk et al. |
| 6,584,182 B2 | 6/2003 | Brodnick |
| 6,584,454 B1 | 6/2003 | Hummel, Jr. et al. |
| 6,585,645 B2 | 7/2003 | Hutchinson |
| 6,589,170 B1 | 7/2003 | Flach et al. |
| 6,593,528 B2 | 7/2003 | Franklin-Lees et al. |
| 6,593,845 B1 | 7/2003 | Friedman et al. |
| 6,594,146 B2 | 7/2003 | Frangesch et al. |
| 6,594,519 B2 | 7/2003 | Stoycos et al. |
| 6,600,418 B2 | 7/2003 | Francis et al. |
| 6,600,421 B2 | 7/2003 | Freeman |
| 6,603,494 B1 | 8/2003 | Banks et al. |
| 6,609,115 B1 | 8/2003 | Mehring et al. |
| 6,616,606 B1 | 9/2003 | Petersen et al. |
| 6,622,088 B2 | 9/2003 | Hood |
| 6,640,246 B1 | 10/2003 | Gary, Jr. et al. |
| 6,643,238 B2 | 11/2003 | Nakajima |
| 6,650,346 B1 | 11/2003 | Jaeger et al. |
| 6,659,947 B1 | 12/2003 | Carter et al. |
| 6,665,385 B2 | 12/2003 | Rogers et al. |
| 6,665,820 B1 | 12/2003 | Frowein et al. |
| 6,669,630 B1 | 12/2003 | Joliat et al. |
| 6,671,547 B2 | 12/2003 | Lyster et al. |
| 6,671,563 B1 | 12/2003 | Engelson et al. |
| 6,685,633 B2 | 2/2004 | Albert et al. |
| 6,689,091 B2 | 2/2004 | Bui et al. |
| 6,693,513 B2 | 2/2004 | Tuttle |
| 6,693,514 B2 | 2/2004 | Perea, Jr. et al. |
| 6,694,367 B1 | 2/2004 | Miesbauer et al. |
| 6,694,509 B1 | 2/2004 | Stoval et al. |
| 6,697,765 B2 | 2/2004 | Kuth |
| 6,707,476 B1 | 3/2004 | Hochstedler |
| 6,714,913 B2 | 3/2004 | Brandt et al. |
| 6,721,818 B1 | 4/2004 | Nakamura |
| 6,726,634 B2 | 4/2004 | Freeman |
| 6,727,818 B1 | 4/2004 | Wildman et al. |
| 6,731,311 B2 | 5/2004 | Bufe et al. |
| 6,731,908 B2 | 5/2004 | Berliner et al. |
| 6,731,989 B2 | 5/2004 | Engleson et al. |
| 6,740,033 B1 | 5/2004 | Olejniczak et al. |
| 6,747,560 B2 | 6/2004 | Stevens, III |
| 6,747,562 B2 | 6/2004 | Giraldin et al. |
| 6,749,566 B2 | 6/2004 | Russ |
| 6,751,630 B1 | 6/2004 | Franks et al. |
| 6,754,545 B2 | 6/2004 | Haeuser et al. |
| 6,754,883 B2 | 6/2004 | DeBusk et al. |
| 6,756,918 B2 | 6/2004 | Fomukong |
| 6,759,959 B2 | 7/2004 | Wildman |
| 6,763,541 B2 | 7/2004 | Mahoney et al. |
| 6,771,172 B1 | 8/2004 | Robinson et al. |
| 6,773,396 B2 | 8/2004 | Flach et al. |
| 6,778,225 B2 | 8/2004 | David |
| 6,781,517 B2 | 8/2004 | Moster et al. |
| 6,784,797 B2 | 8/2004 | Smith et al. |
| 6,791,460 B2 | 9/2004 | Dixon et al. |
| 6,792,396 B2 | 9/2004 | Inda et al. |
| 6,798,533 B2 | 9/2004 | Tipirneni |
| 6,801,227 B2 | 10/2004 | Bocionek et al. |
| 6,807,543 B2 | 10/2004 | Muthya |
| 6,812,824 B1 | 11/2004 | Goldinger et al. |
| 6,825,763 B2 | 11/2004 | Ulrich et al. |
| 6,826,578 B2 | 11/2004 | Brackett et al. |
| 6,828,992 B1 | 12/2004 | Freeman et al. |
| 6,829,796 B2 | 12/2004 | Salvatini et al. |
| 6,830,549 B2 | 12/2004 | Bui et al. |
| 6,832,199 B1 | 12/2004 | Kucek et al. |
| 6,838,992 B2 | 1/2005 | Tenarvitz |
| 6,840,117 B2 | 1/2005 | Hubbard, Jr. |

(56) References Cited

U.S. PATENT DOCUMENTS

| | | |
|---|---|---|
| 6,843,415 B2 | 1/2005 | Vogler |
| 6,847,435 B2 | 1/2005 | Honda et al. |
| 6,847,814 B1 | 1/2005 | Vogeleisen |
| 6,859,761 B2 | 2/2005 | Bensky et al. |
| 6,868,256 B2 | 3/2005 | Dooley et al. |
| 6,871,211 B2 | 3/2005 | Labounty et al. |
| 6,873,884 B2 | 3/2005 | Brackett et al. |
| 6,876,303 B2 | 4/2005 | Reeder et al. |
| 6,876,985 B2 | 4/2005 | Kawanaka |
| 6,884,255 B1 | 4/2005 | Newton |
| 6,885,288 B2 | 4/2005 | Pincus |
| 6,891,909 B2 | 5/2005 | Hurley et al. |
| 6,897,780 B2 | 5/2005 | Ulrich et al. |
| 6,904,161 B1 | 6/2005 | Becker et al. |
| 6,909,995 B2 | 6/2005 | Shiraishi |
| 6,912,549 B2 | 6/2005 | Rotter et al. |
| 6,915,170 B2 | 7/2005 | Engleson et al. |
| 6,925,367 B2 | 8/2005 | Fontius |
| 6,930,878 B2 | 8/2005 | Brackett et al. |
| 6,954,148 B2 | 10/2005 | Pulkkinen et al. |
| 6,958,706 B2 | 10/2005 | Chaco et al. |
| 6,968,194 B2 | 11/2005 | Aljadeff et al. |
| 6,972,682 B2 | 12/2005 | Lareau et al. |
| 6,988,989 B2 | 1/2006 | Weiner et al. |
| 6,998,985 B2 | 2/2006 | Reisman et al. |
| 6,998,986 B2 | 2/2006 | Smith |
| 7,002,468 B2 | 2/2006 | Eveland et al. |
| 7,003,443 B2 | 2/2006 | Ford et al. |
| 7,005,980 B1 | 2/2006 | Schmidt et al. |
| 7,009,495 B2 | 3/2006 | Hughes et al. |
| 7,009,516 B2 | 3/2006 | Enea |
| 7,014,100 B2 | 3/2006 | Zierolf |
| 7,019,663 B2 | 3/2006 | Sharony |
| 7,030,761 B2 | 4/2006 | Bridgelall et al. |
| 7,030,811 B2 | 4/2006 | Goren et al. |
| 7,034,684 B2 | 4/2006 | Boman et al. |
| 7,034,690 B2 | 4/2006 | Chaco |
| 7,035,818 B1 | 4/2006 | Bandy et al. |
| 7,038,573 B2 | 5/2006 | Bann |
| 7,038,584 B2 | 5/2006 | Carter |
| 7,038,588 B2 | 5/2006 | Boone et al. |
| 7,038,589 B2 | 5/2006 | Schmidt et al. |
| 7,042,358 B2 | 5/2006 | Moore |
| 7,042,361 B2 | 5/2006 | Kazdin et al. |
| 7,044,387 B2 | 5/2006 | Becker et al. |
| 7,046,153 B2 | 5/2006 | Oja et al. |
| 7,046,162 B2 | 5/2006 | Dunstan |
| 7,049,594 B2 | 5/2006 | Wu et al. |
| 7,053,779 B2 | 5/2006 | Thompson |
| 7,053,781 B1 | 5/2006 | Haire et al. |
| 7,053,831 B2 | 5/2006 | Dempsey et al. |
| 7,056,289 B2 | 6/2006 | Kasper et al. |
| 7,057,509 B2 | 6/2006 | Gualdi et al. |
| 7,061,366 B2 | 6/2006 | Bell et al. |
| 7,061,384 B2 | 6/2006 | Fujimoto |
| 7,062,455 B1 | 6/2006 | Tobey |
| 7,068,143 B2 | 6/2006 | Doering et al. |
| 7,071,820 B2 | 7/2006 | Callaway |
| 7,071,843 B2 | 7/2006 | Hashida et al. |
| 7,075,438 B2 | 7/2006 | Kent et al. |
| 7,080,061 B2 | 7/2006 | Kabala |
| 7,084,740 B2 | 8/2006 | Bridgelall |
| 7,091,879 B2 | 8/2006 | Swetlik et al. |
| 7,092,376 B2 | 8/2006 | Schuman |
| 7,099,895 B2 | 8/2006 | Dempsey |
| 7,102,510 B2 | 9/2006 | Boling et al. |
| 7,106,189 B2 | 9/2006 | Burneske et al. |
| 7,116,230 B2 | 10/2006 | Klowak |
| 7,117,027 B2 | 10/2006 | Zheng et al. |
| 7,138,913 B2 | 11/2006 | Mackenzie et al. |
| 7,142,112 B2 | 11/2006 | Buckingham et al. |
| 7,151,455 B2 | 12/2006 | Lindsay et al. |
| 7,152,791 B2 | 12/2006 | Chappidi et al. |
| 7,154,397 B2 | 12/2006 | Zerhusen et al. |
| 7,158,030 B2 | 1/2007 | Chung |
| 7,164,354 B1 | 1/2007 | Panzer |
| 7,165,040 B2 | 1/2007 | Ehrman et al. |
| 7,167,095 B2 | 1/2007 | Carrender |
| 7,170,407 B2 | 1/2007 | Wagner |
| 7,174,172 B2 | 2/2007 | Sharony et al. |
| 7,190,778 B2 | 3/2007 | Kucmerowski |
| 7,196,621 B2 | 3/2007 | Kochis |
| 7,199,716 B2 | 4/2007 | Shanks et al. |
| 7,202,785 B2 | 4/2007 | Maloney |
| 7,203,690 B2 | 4/2007 | Braun et al. |
| 7,209,790 B2 | 4/2007 | Thompson et al. |
| 7,218,231 B2 | 5/2007 | Higham |
| 7,225,241 B2 | 5/2007 | Yada |
| 7,230,536 B2 | 6/2007 | Shinada et al. |
| 7,242,306 B2 | 7/2007 | Wildman et al. |
| 7,242,308 B2 | 7/2007 | Ulrich et al. |
| 7,248,880 B2 | 7/2007 | Gheorghiu et al. |
| 7,248,933 B2 | 7/2007 | Wildman |
| 7,259,676 B2 | 8/2007 | Knadle, Jr. et al. |
| 7,265,668 B1 | 9/2007 | Brosius |
| 7,269,427 B2 | 9/2007 | Hoctor et al. |
| 7,277,048 B2 | 10/2007 | Hessing |
| 7,277,889 B2 | 10/2007 | Addonisio et al. |
| 7,283,046 B2 | 10/2007 | Culpepper et al. |
| 7,283,423 B2 | 10/2007 | Holm et al. |
| 7,286,868 B2 | 10/2007 | Govari |
| 7,292,151 B2 | 11/2007 | Ferguson et al. |
| 7,295,115 B2 | 11/2007 | Aljadeff et al. |
| 7,295,132 B2 | 11/2007 | Steiner |
| 7,298,359 B2 | 11/2007 | Kim et al. |
| 7,301,451 B2 | 11/2007 | Hastings |
| 7,304,577 B2 | 12/2007 | Waldner et al. |
| 7,304,578 B1 | 12/2007 | Sayers et al. |
| 7,304,579 B2 | 12/2007 | Diorio et al. |
| 7,307,522 B2 | 12/2007 | Dawson |
| 7,313,403 B2 | 12/2007 | Gong et al. |
| 7,315,248 B2 | 1/2008 | Egbert |
| 7,315,281 B2 | 1/2008 | Dejanovic et al. |
| 7,319,386 B2 | 1/2008 | Collins, Jr. et al. |
| 7,319,395 B2 | 1/2008 | Puzio et al. |
| 7,319,397 B2 | 1/2008 | Chung et al. |
| 7,319,412 B1 | 1/2008 | Coppinger et al. |
| 7,321,305 B2 | 1/2008 | Göllü |
| 7,333,018 B2 | 2/2008 | Singh et al. |
| 7,336,187 B2 | 2/2008 | Hubbard, Jr. et al. |
| 7,336,563 B2 | 2/2008 | Holm |
| 7,339,477 B2 | 3/2008 | Puzio et al. |
| 7,339,479 B2 | 3/2008 | Nishimura |
| 7,362,656 B2 | 4/2008 | Holm |
| 7,370,808 B2 | 5/2008 | Eastin |
| 7,375,648 B1 | 5/2008 | Mulka et al. |
| 7,375,654 B2 | 5/2008 | Culpepper et al. |
| 7,376,123 B2 | 5/2008 | Reuss |
| 7,394,385 B2 | 7/2008 | Franco, Jr. et al. |
| 7,411,509 B2 | 8/2008 | Rosenfeld et al. |
| 7,415,212 B2 | 8/2008 | Matsushita et al. |
| 7,417,544 B2 | 8/2008 | Artem et al. |
| 7,443,299 B2 | 10/2008 | Forster |
| 7,446,664 B2 | 11/2008 | White |
| 7,473,097 B2 | 1/2009 | Raby et al. |
| 7,474,224 B2 | 1/2009 | Long et al. |
| 7,515,044 B2 | 4/2009 | Welch et al. |
| 7,518,502 B2 | 4/2009 | Austin et al. |
| 7,538,679 B2 | 5/2009 | Shanks |
| 7,541,927 B2 | 6/2009 | Dupler et al. |
| 7,551,083 B2 | 6/2009 | Modes et al. |
| 7,567,794 B2 | 7/2009 | Dempsey |
| 7,598,853 B2 | 10/2009 | Becker et al. |
| 7,623,250 B2 | 11/2009 | Moctezuma de la Barrera et al. |
| 7,627,334 B2 | 12/2009 | Cohen et al. |
| 7,664,686 B2 | 2/2010 | Czyszczewski et al. |
| 7,667,572 B2 | 2/2010 | Husak et al. |
| 7,714,728 B2 | 5/2010 | Koblasz |
| 7,724,147 B2 | 5/2010 | Brown |
| 7,725,195 B2 | 5/2010 | Lima et al. |
| 7,734,476 B2 | 6/2010 | Wildman et al. |
| 7,737,850 B2 | 6/2010 | Malik |
| 7,750,793 B2 | 7/2010 | Juels |
| 7,755,541 B2 | 7/2010 | Wisherd et al. |

(56) References Cited

U.S. PATENT DOCUMENTS

| | | |
|---|---|---|
| 7,756,723 B2 | 7/2010 | Rosow et al. |
| 7,761,320 B2 | 7/2010 | Fliess et al. |
| 7,765,286 B2 | 7/2010 | Mark |
| 7,800,914 B2 | 9/2010 | Dully |
| 7,844,505 B1 | 11/2010 | Arneson et al. |
| 7,848,760 B2 | 12/2010 | Caspi et al. |
| 7,869,861 B2 | 1/2011 | Moctezuma de la Barrera et al. |
| 7,890,349 B2 | 2/2011 | Cole et al. |
| 7,893,842 B2 | 2/2011 | Deutsch |
| 7,907,053 B2 | 3/2011 | Wildman et al. |
| 7,916,023 B2 | 3/2011 | Rado |
| 7,920,050 B2 | 4/2011 | Juels et al. |
| 7,928,844 B2 | 4/2011 | Mackenzie et al. |
| 7,933,780 B2 | 4/2011 | De La Huerga |
| 7,958,087 B2 | 6/2011 | Blumenau |
| 7,966,008 B2 | 6/2011 | Graves et al. |
| 8,026,821 B2 | 9/2011 | Reeder et al. |
| 8,031,057 B2 | 10/2011 | McNeely et al. |
| 8,073,558 B2 | 12/2011 | Koch et al. |
| 8,102,254 B2 | 1/2012 | Becker et al. |
| 8,160,677 B2 | 4/2012 | Gielen et al. |
| 8,164,444 B2 | 4/2012 | Anderson et al. |
| 8,190,730 B2 | 5/2012 | Dempsey |
| 8,223,009 B2 | 7/2012 | Anderson et al. |
| 8,248,467 B1 | 8/2012 | Ganick et al. |
| 8,272,892 B2 | 9/2012 | McNeely et al. |
| 8,284,047 B2 | 10/2012 | Collins, Jr. et al. |
| 8,310,364 B2 | 11/2012 | Derks et al. |
| 8,319,633 B2 | 11/2012 | Becker et al. |
| 8,321,302 B2 | 11/2012 | Bauer et al. |
| 8,334,898 B1 | 12/2012 | Ryan et al. |
| 8,334,901 B1 | 12/2012 | Ganick et al. |
| 8,390,462 B2 | 3/2013 | Belz et al. |
| 8,416,072 B2 | 4/2013 | Tenarvitz |
| 8,416,290 B2 | 4/2013 | Ryan et al. |
| 8,432,438 B2 | 4/2013 | Ryan et al. |
| 8,436,896 B2 | 5/2013 | Staats et al. |
| 8,447,626 B2 | 5/2013 | Sun et al. |
| 8,457,502 B2 | 6/2013 | Ryan et al. |
| 8,461,968 B2 | 6/2013 | Ball et al. |
| 8,461,982 B2 | 6/2013 | Becker et al. |
| 8,514,071 B2 | 8/2013 | Derks et al. |
| 8,516,514 B2 | 8/2013 | Belz et al. |
| 8,519,823 B2 | 8/2013 | Rinkes |
| 8,520,065 B2 | 8/2013 | Staats et al. |
| 8,558,660 B2 | 10/2013 | Nix et al. |
| 8,604,916 B2 | 12/2013 | McNeely et al. |
| 8,604,917 B2 | 12/2013 | Collins et al. |
| 8,610,562 B2 | 12/2013 | Weiner et al. |
| 8,650,045 B2 | 2/2014 | Baldock et al. |
| 8,674,826 B2 | 3/2014 | Becker et al. |
| 8,689,376 B2 | 4/2014 | Becker et al. |
| 8,752,045 B2 | 6/2014 | Fitzgerald et al. |
| 8,781,847 B2 | 7/2014 | Simms et al. |
| 9,020,963 B2 | 4/2015 | Goodman et al. |
| 9,026,301 B2 | 5/2015 | Zini et al. |
| 9,830,424 B2 | 11/2017 | Dixon et al. |
| 2001/0050610 A1 | 12/2001 | Gelston |
| 2001/0051765 A1 | 12/2001 | Walker et al. |
| 2002/0044059 A1 | 4/2002 | Reeder et al. |
| 2002/0067273 A1 | 6/2002 | Jaques et al. |
| 2002/0070867 A1 | 6/2002 | Conway et al. |
| 2002/0165733 A1 | 11/2002 | Pulkkinen et al. |
| 2002/0173286 A1 | 11/2002 | Lindoff et al. |
| 2002/0173991 A1 | 11/2002 | Avitall |
| 2003/0010345 A1 | 1/2003 | Koblasz et al. |
| 2003/0028449 A1 | 2/2003 | Heinen et al. |
| 2003/0132845 A1 | 7/2003 | McDaniel, III |
| 2003/0149598 A1 | 8/2003 | Santoso et al. |
| 2003/0176798 A1 | 9/2003 | Simon |
| 2004/0024660 A1 | 2/2004 | Ganesh et al. |
| 2004/0106854 A1 | 6/2004 | Muraki |
| 2004/0186358 A1 | 9/2004 | Chernow et al. |
| 2005/0071198 A1 | 3/2005 | Krupa |
| 2005/0122119 A1 | 6/2005 | Barlow |
| 2005/0131729 A1 | 6/2005 | Melby et al. |
| 2006/0012474 A1 | 1/2006 | Lu et al. |
| 2006/0022818 A1 | 2/2006 | Piltonen |
| 2006/0028336 A1 | 2/2006 | Glenn et al. |
| 2006/0031259 A1 | 2/2006 | Gibson et al. |
| 2006/0038676 A1 | 2/2006 | Richards |
| 2006/0071774 A1 | 4/2006 | Brown et al. |
| 2006/0082444 A1 | 4/2006 | Sweeney, II et al. |
| 2006/0097863 A1 | 5/2006 | Horowitz et al. |
| 2006/0135083 A1 | 6/2006 | Leinonen et al. |
| 2006/0161214 A1 | 7/2006 | Patel |
| 2006/0220798 A1 | 10/2006 | Willis |
| 2006/0253590 A1 | 11/2006 | Nagy et al. |
| 2007/0005558 A1 | 1/2007 | Canfield |
| 2007/0015960 A1 | 1/2007 | Gornert et al. |
| 2007/0033072 A1 | 2/2007 | Bildirici |
| 2007/0073116 A1 | 3/2007 | Kiani et al. |
| 2007/0093879 A1 | 4/2007 | Bek et al. |
| 2007/0123173 A1 | 5/2007 | Stobbe |
| 2007/0129967 A1 | 6/2007 | Thompson et al. |
| 2007/0157385 A1* | 7/2007 | Lemire ............... A61G 7/0509<br>5/600 |
| 2007/0210917 A1 | 9/2007 | Collins, Jr. et al. |
| 2007/0271122 A1 | 11/2007 | Zaleski |
| 2008/0004993 A1 | 1/2008 | Horspool et al. |
| 2008/0026713 A1 | 1/2008 | Sekhar et al. |
| 2008/0040244 A1 | 2/2008 | Ricciuti et al. |
| 2008/0100706 A1 | 5/2008 | Breed |
| 2008/0106418 A1 | 5/2008 | Sloan et al. |
| 2008/0108372 A1 | 5/2008 | Breed |
| 2008/0126125 A1 | 5/2008 | Lichtenstein et al. |
| 2008/0126126 A1 | 5/2008 | Ballai |
| 2008/0136621 A1 | 6/2008 | Malik et al. |
| 2008/0136635 A1 | 6/2008 | Malik |
| 2008/0140544 A1 | 6/2008 | Ehrman et al. |
| 2008/0180322 A1 | 7/2008 | Islam et al. |
| 2008/0201388 A1 | 8/2008 | Wood et al. |
| 2008/0215360 A1 | 9/2008 | Dicks et al. |
| 2008/0238676 A1 | 10/2008 | Dhillon et al. |
| 2008/0242945 A1 | 10/2008 | Gugliotti et al. |
| 2008/0300918 A1 | 12/2008 | Tenenbaum et al. |
| 2008/0312974 A2 | 12/2008 | Rosow et al. |
| 2008/0312975 A2 | 12/2008 | Rosow et al. |
| 2009/0018882 A1 | 1/2009 | Burton et al. |
| 2009/0033500 A1 | 2/2009 | Malik et al. |
| 2009/0079549 A1 | 3/2009 | Ruder |
| 2009/0300507 A1 | 12/2009 | Raghavan et al. |
| 2010/0001838 A1 | 1/2010 | Miodownik et al. |
| 2010/0217618 A1 | 8/2010 | Piccirillo et al. |
| 2010/0289885 A1 | 11/2010 | Lu et al. |
| 2011/0050411 A1 | 3/2011 | Schuman et al. |
| 2011/0125513 A1 | 5/2011 | Tenarvitz et al. |
| 2011/0125524 A1 | 5/2011 | Tenarvitz et al. |
| 2011/0208541 A1 | 8/2011 | Wilson et al. |
| 2011/0227740 A1 | 9/2011 | Wohltjen |
| 2012/0316892 A1* | 12/2012 | Huster ............... G16H 40/20<br>705/2 |
| 2013/0069771 A1 | 3/2013 | Frondorf |
| 2014/0207490 A1* | 7/2014 | Shindo ............... G16H 20/70<br>705/3 |
| 2015/0081335 A1 | 3/2015 | Dixon et al. |

OTHER PUBLICATIONS

EP Search Report for Application No. EP 14185232.7-1952, dated Mar. 16, 2015, 6 pages.

Summons to Attend Oral Proceedings issued by the European Patent Office for European Patent Application No. 14185232.7; dated Nov. 13, 2020 (9 pages).

* cited by examiner

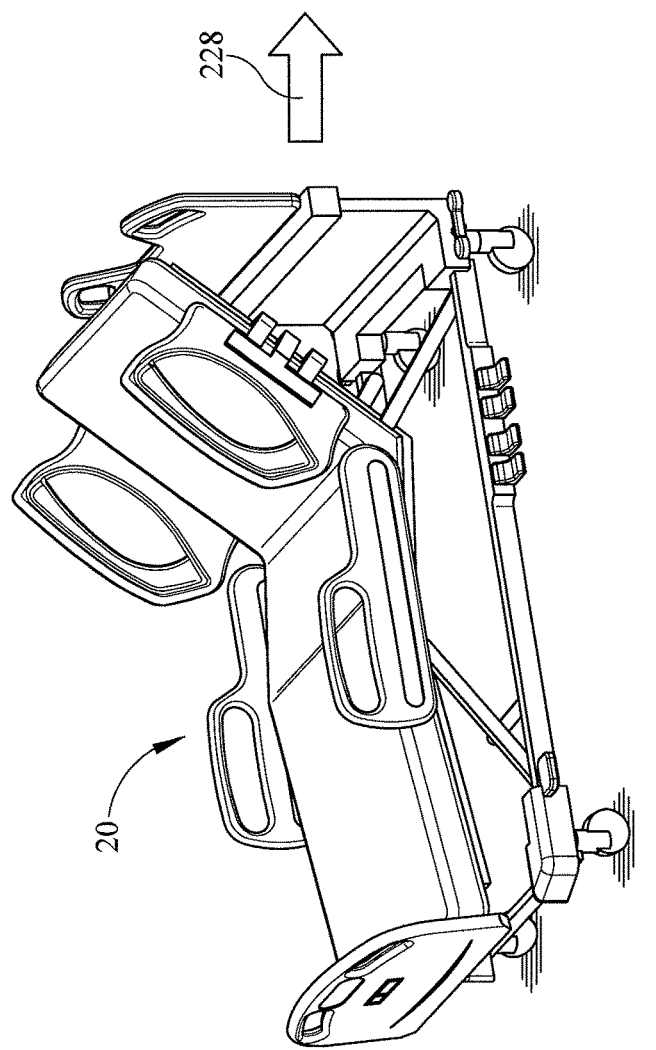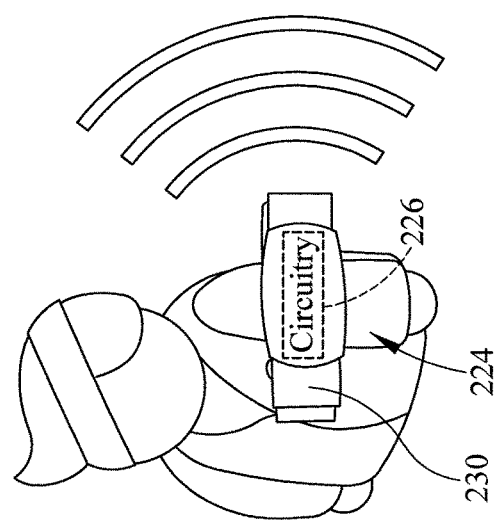
FIG. 19

BED/ROOM/PATIENT ASSOCIATION SYSTEMS AND METHODS

CROSS REFERENCE TO RELATED APPLICATIONS

The present application is a continuation of U.S. application Ser. No. 14/487,279, filed Sep. 16, 2014, now U.S. Pat. No. 9,830,424, which claims the benefit, under 35 U.S.C. § 119(e), of U.S. Provisional Application No. 61/879,399, filed Sep. 18, 2013, and each of which is hereby incorporated by reference herein in its entirety.

BACKGROUND

The present disclosure relates to systems and methods for associating beds, rooms, and/or patients and particularly, to such association systems and methods used in a healthcare facility.

Systems and methods for determining the location of a patient bed within a healthcare facility are known. In some of the known systems, a locating tag is attached to the bed and periodically transmits a wireless signal that includes a tag identifier (aka a "tag ID") which is a string of characters such as letters and/or numbers and/or symbols that uniquely identify the tag. In some such prior art systems, a set of wireless receivers are mounted at fixed locations throughout the healthcare facility and are coupled to the computer network of the healthcare facility. A receiver in the vicinity of a tag receives the tag ID and transmits it along with a receiver ID to other computer devices of the network. Each receiver ID corresponds to a location in the healthcare facility. Thus, one or more remote computer devices are able to determine the location of the bed based on the tag ID and the receiver ID.

In many of the prior art systems, the wireless signal from the tag is an infrared signal that requires an uninterrupted line of sight to a receiver. If the line of sight is blocked, the receiver does not receive the signal from the tag. Thus, in more recent times, the desire has been to use radio frequency (RF) tags but the drawback with those systems is that RF signals are able to penetrate floors, ceilings and walls in a healthcare facility such that multiple receivers sometimes receive the same wireless RF signal and further processing of some type is needed to resolve the ambiguity of the bed's location. Some prior art systems have resolved the ambiguities by analyzing signal strength or analyzing time of flight information.

In some known prior art systems, patient beds have circuitry that transmits a bed ID, as opposed to a tag ID, as well as bed status data from the beds. Typically, the transmissions are made over a cable that extends from the bed to some sort of interface unit mounted to a wall in a room, but there is the option to do this wirelessly in some prior art systems by using a wireless interface unit mounted to the room wall. In any event, the interface unit that receives the transmissions from the bed, either via a wired or wireless connection, is then connected to the network of the healthcare facility, typically, via a wired connection. In these prior art systems, the installation of interface units just to receive bed ID and bed status data is an added cost to the overall network of the healthcare facility.

The use of wireless access points in healthcare facilities to receive Wi-Fi signals from a variety of equipment and computer devices is becoming more widespread. Thus, there is a need to develop systems and methods for making bed-to-room associations or patient-to-room associations or patient-to-bed associations or patient-to-bed-to-room associations that minimize the amount of specialized receivers, interface units, or other equipment that must be coupled to the network of the facility.

SUMMARY

The present invention may comprise one or more of the features recited in the appended claims and/or the following features which each are considered to be optional and which, alone or in any combination, may comprise patentable subject matter:

A system for use in a healthcare facility that may have a network may be provided according to this disclosure. The system may include a light source that may emit visible light that may have a signature that may be unique to a location of the healthcare facility. The system may also include a patient bed that may have circuitry that may analyze the light from the light source to determine the signature corresponding to the location. The circuitry may be configured to transmit data corresponding to the signature and to transmit bed identifier (ID) to the network.

In some embodiments, the signature may comprise a specified wavelength. The light source may be programmable to emit light at the specified wavelength. Alternatively or additionally, the signature may comprise a specified pulse frequency that may be sufficiently great so as to be imperceptible by human vision. The light source may be programmable to emit light at the specified pulse frequency. Thus, the signature may comprise a specified wavelength at a specified pulse frequency in some embodiments. In such embodiments, the light source may be programmable to emit light at the specified wavelength and at the specified pulse frequency.

According to this disclosure, the light source may comprise a light bulb that provides room lighting. In other embodiment, the light source may comprise a display screen, such as one that may be mounted to a ceiling or a wall of a room of the healthcare facility. The display screen may be the display screen of a computer device such as the display screen of a room station of a nurse call system, for example. There may be a light source in a number of rooms and the signature from the light source, be it a light bulb or a display screen, may be different for each room. The light source may include at least one light emitting diode (LED).

Further according to this disclosure, the circuitry of the patient bed may include a red-green-blue image sensor that may sense the light emitted by the light source. Alternatively or additionally, the circuitry of the patient bed may include a camera that receives the light emitted by the light source.

The system may further include a computer device that may be coupled to the network remote from the light source and the patient bed. The computer device may determine the location of the healthcare facility in which the light source may be located based on the data corresponding to the signature. The computer device may associate the bed ID with the location of the healthcare facility.

In some embodiments, the circuitry of the patient bed may wirelessly transmits the data corresponding to the signature and the bed ID to the computer device via a wireless access point of the network. Alternatively or additionally, the circuitry of the patient bed may transmit the data corresponding to the signature and the bed ID to the computer device via a wired connection from the bed to the network.

According to some embodiments, a light source may emit visible light and infrared (IR) light. The IR light may have a signature that may be unique to a location of the healthcare facility. A patient bed may include circuitry that may analyze the IR light from the light source to determine the signature corresponding to the location. The circuitry may be configured to transmit data corresponding to the signature and to transmit bed identifier (ID) to the network.

In some embodiments, the IR light may only be emitted when the visible light is turned off. According to this disclosure, the light source may include an energy storage device that may power the IR light while the visible light is turned off. The energy storage device may be charged when the visible light is turned on.

In some embodiments, the visible light may also be emitted with the signature such that the visible light and the IR light have the same signature. For example, the signature may comprise a specified pulse frequency. The specified pulse frequency may be programmable.

Further according to this disclosure, another system for use in a healthcare facility having a network may be provided. The system may include an array of redundant bar codes and a patient bed that may be spaced from the array of redundant bar codes. The patient bed may include circuitry that may comprise a bar code reader that may read at least one of the redundant bar codes in the array. The circuitry may be configured to transmit data corresponding to the at least one of the redundant bar codes and to transmit bed identifier (ID) to the network.

The array of redundant bar codes may be affixed to a vertical surface in a room of the healthcare facility. In such embodiments, the patient bed may include a frame that may have longitudinally spaced ends. The bar code reader may be mounted adjacent to one of the longitudinally spaced ends. The vertical surface may comprise a wall of the room or a panel of an architectural product that may be mounted to a wall of the room. The architectural product may include a bed locator unit, a headwall unit, or a column, for example. Alternatively or additionally, the array of redundant bar codes may be affixed to a horizontal surface in the room, such as the floor. The patient bed may include a frame and the bar code reader may be coupled to the frame so as to point downwardly toward the floor.

In some embodiments, the array of redundant bar codes may include at least one row having at least three identical bar codes. In other embodiments, the array of redundant bar codes may include at least three rows each having at least three identical bar codes. It should be appreciated that this disclosure contemplates any number of rows and columns of redundant bar codes greater or lesser in number than three.

Another system contemplated by this disclosure may include a patient bed that may have a frame, circuitry that may be carried by the frame, and a graphical user interface that may be carried by the frame and that may be coupled to the circuitry. The graphical user interface may display at least one user interface screen that may be used by a caregiver to manually enter location data that may be indicative of a location in a healthcare facility that may be occupied by the patient bed. The circuitry may transmit off of the bed the location data entered by the caregiver and a bed identification (ID).

In some embodiments, the location data may comprise a room number. The graphical user interface may include a change button that may be selected to initiate a change of the location data. A keyboard screen may appear on the graphical user interface in response to the change button being selected. The keyboard screen may permit the caregiver to type new location data that may be indicative of a new location that may be occupied by the patient bed.

In some embodiments, the system may include at least one remote computer device that may receive the location data and the bed ID for purposes of making a bed-to-room association. The patient bed may be coupled to the at least one remote computer device via a network of the healthcare facility. The location data and the bed ID may be transmitted off of the bed in the form of a wireless transmission. The circuitry also may transmit bed status data off of the bed.

In some embodiments, the location data may include unit data that may be indicative of a unit of the healthcare facility that may be occupied by the patient bed and a room number of the unit in which the patient bed may be situated. The graphical user interface may display a first screen that may be used to select the unit of the healthcare facility that may be occupied by the patient bed from a menu of units and a second screen that may be used to select the room number from a menu of room numbers.

Further according to this disclosure, a system for associating a bed to a room of a healthcare facility may include a locator unit that may be fixed in place and that may transmit a location ID. The system may include a patient bed that may have first circuitry that may have a first ID and that may receive the location ID. The patient bed may have second circuitry that may be independent of the first circuitry. The second circuitry may be configured to transmit a bed ID and bed status data.

The system may further have a first transceiver that may be spaced from the locator unit and that may be spaced from the patient bed. The first transceiver may receive the first ID and location ID transmitted by the first circuitry. A second transceiver of the system may be spaced from and independent of the first transceiver. The second transceiver may receive the bed ID and the bed status data that may be transmitted by the second circuitry.

The system may also have a first remote computer device that may receive the location ID and first ID that may be transmitted to the first remote computer device by the first transceiver. The system may further have a second remote computer device that may receives the bed ID and the bed status data which may be transmitted to the second computer device by the second transceiver. The first and second remote computer devices may cooperate to associate the location ID and the bed status data with the bed ID.

In some embodiments, the first circuitry may be included as part of a tag that may attach to an exterior surface of the patient bed. The first circuitry may transmit the first ID and the location ID using a first wireless transmission technology. The second circuitry may transmit the bed ID and the bed status data using a second wireless transmission technology. The first wireless transmission technology may differ from the second wireless transmission technology. For example, the first wireless transmission technology may comprise one of infrared technology, radio frequency technology, and ultrasonic technology and the second wireless transmission technology may comprise a different one of infrared technology, radio frequency technology, and ultrasonic technology.

Another system according to this disclosure may include a locator unit that may be fixed in place and that may transmit a location ID in a first format. The system may also include a patient bed that may have a bed ID and circuitry that may have stored therein ID translation software. The circuitry may receive the location ID in the first format and, in accordance with the ID translation software, may convert the location ID to a modified ID that may have a second format different than the first format. The circuitry may transmit the bed ID and the modified ID such that the location ID received by the circuitry of the patient bed may not be transmitted by the circuitry.

The system may further include a remote computer device that may receive the bed ID and the modified ID and that may determine a location of the patient bed based on the modified ID. The modified ID may include a room number of a room in a healthcare facility in which the patient bed may be located and the translation software may include a look up table that may convert the location ID into the room number of the modified ID. The location ID may have a different number of bits of information than the modified ID.

Yet another system according to this disclosure may comprise a locator unit that may be fixed in place and that transmits a location ID. The system further may have a patient bed that may have a bed ID and circuitry that may have stored therein ID mutation software. The circuitry may receive the location ID and, in accordance with the ID mutation software, may mutate the location ID and the bed ID into a mutated ID. The mutated ID may be a single unique ID. The circuitry may transmit the mutated ID, whereby neither the location ID received by the circuitry nor the bed ID of the patient bed may be transmitted by the circuitry.

According to some embodiments, mutating the location ID and the bed ID into the mutated ID may include adding the location ID and the bed ID to create an added ID. Mutating the location ID and the bed ID into the mutated ID may further include applying a hashing function to the added ID to create a hashed ID. While any suitable hashing function is contemplated by this disclosure, in some embodiments, the hashing function may comprise a cryptographic hashing function.

The system may further comprise a remote computer device that may having decoding software that may determine the location ID and the bed ID based on the hashed ID. For example, the decoding software may include a look up table that may identify a location ID and a bed ID for each possible hashed ID. Alternatively or additionally, the decoding software may generate comparison hashed ID's by sequentially adding and hashing all known bed ID's with all known location ID's until one of the comparison hashed ID's matches the hashed ID then storing in an association database the location ID and the bed ID that caused the comparison hashed ID to match the hashed ID.

According to each of the embodiments contemplated herein, the circuitry of the patient bed may also transmit bed status data and/or a patient ID of a patient assigned to the patient bed. According to some embodiments, the remote computer device may having decoding software that determines the location ID and bed ID based on the hashed ID and that associates the location ID, bed ID and the bed status data and/or the patient ID in a database.

According to this disclosure, a method may include receiving, with circuitry on a patient bed, light from a light source that may emit visible light that may have a signature that may be unique to a location of the healthcare facility. The method may further include analyzing, using software stored in the circuitry of the patient bed, the light from the light source to determine the signature corresponding to the location, and transmitting, using the circuitry of the patient bed, data corresponding to the signature and a bed ID. In some embodiments, the method further may include receiving, with a remote computer device, the bed ID and the data corresponding to the signature and associating the location of the patient bed with the patient bed.

Another method according to this disclosure may include receiving, with circuitry on a patient bed, light from a light source that may be operable to emit IR light that may have a signature that is unique to a location of the healthcare facility and that may also be operable to emit visible light. The method may further include analyzing, using software stored in the circuitry of the patient bed, the IR light from the light source to determine the signature corresponding to the location and transmitting, using the circuitry of the patient bed, data corresponding to the signature and a bed ID.

In some embodiments, the method may further include receiving, with a remote computer device, the bed ID and the data corresponding to the signature and associating the location of the patient bed with the patient bed based on the data corresponding to the signature. The IR light that may have the signature may be transmitted only when the visible light is turned off.

In some embodiments, the method further includes receiving, with the circuitry of the patient bed, visible light that may have the signature such that the visible light and the IR light may have the same signature. The signature of the visible light and/or the IR light may comprise a specified pulse frequency. As mentioned above, the specified pulse frequency may be programmable.

Yet another method according to this disclosure includes scanning, using a bar code scanner of a patient bed, at least one bar code from an array of redundant bar codes that may be mounted to a surface in a room. The bar code may be indicative of a location of the room. The method may further include transmitting off of the patient bed, using circuitry of the patient bed, data that may correspond to the at least one of the redundant bar codes and a bed ID.

In some embodiments, the method may further include receiving the data corresponding to the at least one of the redundant bar codes and receiving the bed ID at a remote computer device and associating the patient bed with the location based on the data corresponding to the at least one of the redundant bar codes and the bed ID. According to this disclosure, the surface to which the array of redundant bar codes may be mounted may comprise a surface of a room wall, a surface of architectural equipment in the room, or a floor surface.

Still another method according to this disclosure includes displaying, on a graphical user interface of a patient bed, fields that a caregiver may select to manually enter location data indicative of a location in a healthcare facility occupied by the patient bed. The method may further include receiving, on the graphical user interface, selections from the caregiver of the location data and transmitting, from the patient bed, the location data entered by the caregiver and a bed ID.

In some embodiments, the method may further comprise receiving the location data and receiving the bed ID at a remote computer device and associating the patient bed with the location based on the location data and the bed ID. The location data may comprise a room number in some embodiments and may comprise a unit number (or a unit name) and a room number in other embodiments.

Still a further method contemplated by this disclosure includes transmitting a location ID from a locator unit that may be fixed in place in a room of a healthcare facility, receiving, with first circuitry of a patient bed that may be spaced from the locator unit, the location ID. The method may further include transmitting, from the first circuitry, a first ID and the location ID and transmitting, from second circuitry of the patient bed, a bed ID and bed status data. Still further the method may include receiving, with a first transceiver that may be spaced from the locator unit and spaced from the patient bed, the first ID and location ID transmitted by the first circuitry and receiving, with a second transceiver that may be spaced from and independent of the first transceiver, the bed ID and the bed status data transmitted by the second circuitry. The method may also include transmitting the location ID and the first ID from the first transceiver, transmitting the bed ID and the bed status data from the second transceiver, receiving, with a first remote computer device, the location ID and first ID transmitted by the first transceiver, receiving, with a second remote computer device, the bed ID and the bed status data transmitted by the second transceiver, and associating the location ID with the bed status data and the bed ID via cooperation between the first and second remote computer devices.

According to this disclosure, another method may include transmitting a location ID from a locator unit that may be fixed in place in a healthcare facility. The location ID may have a first format. The method also may include receiving the location ID with circuitry of a patient bed that may be spaced from the locator unit and that has a bed ID. The further may include converting the location ID that may have the first format to a modified ID that may have a second format using translation software that may be stored in the circuitry of the patient bed. The second format may be different than the first format. The method may include transmitting, using the circuitry, the bed ID and the modified ID, whereby the location ID received by the circuitry of the patient bed may not be transmitted by the circuitry.

In some embodiments, the method further comprises receiving, with a remote computer device, the bed ID and the modified ID and determining, with the remote computer device, a location of the patient bed based on the modified ID. The modified ID may include a room number of a room in a healthcare facility in which the patient bed may be located and the translation software on the patient bed may include a look up table that may be used to convert the location ID into the room number of the modified ID. In some embodiments, the location ID has a different number of bits of information than the modified ID.

Still another method according to this disclosure may include transmitting a location ID from a locator unit that may be fixed in place in a room of a healthcare facility, receiving the location ID in circuitry of a patient bed having a bed ID, and mutating the location ID and the bed ID into a mutated ID using ID mutation software that may be stored in the circuitry. The mutated ID may be a single unique ID. The method may further include transmitting the mutated ID from the patient bed, whereby neither the location ID received by the circuitry nor the bed ID of the patient bed may be transmitted by the patient bed.

In some embodiments, mutating the location ID and the bed ID into the mutated ID may include adding the location ID and the bed ID to create an added ID. Mutating the location ID and the bed ID into the mutated ID may further comprise applying a hashing function to the added ID to create a hashed ID. The hashing function may comprise a cryptographic hashing function, for example.

The method may further comprise determining the location ID and the bed ID based on the hashed ID at a remote computer using decoding software. The decoding software may include a look up table that identifies a location ID and a bed ID for each possible hashed ID. Alternatively or additionally, the decoding software may generate comparison hashed ID's by sequentially adding and hashing all known bed ID's with all known location ID's until one of the comparison hashed ID's matches the hashed ID then storing in an association database the location ID and the bed ID that caused the comparison hashed ID to match the hashed ID.

In some embodiments, the method may further include transmitting bed status data from the patient bed and, optionally, using a remote computer device to determine the location ID and the bed ID based on the hashed ID and to associate the location ID, bed ID and bed status data in a database. Alternatively or additionally, the method may include transmitting from the patient bed a patient ID of a patient assigned to the patient bed and, optionally, using a remote computer device to determine the location ID and bed ID based on the hashed ID and to associate the location ID, bed ID and patient ID in a database.

According to another aspect of this disclosure, a hospital bed for use with a locating and tracking system may be provided and may include a patient support structure that may be configured to support a patient. The hospital bed may further have circuitry that may be carried by the patient support structure and that may be in communication with the locating and tracking system. The hospital bed may have an indicator that may be coupled to the circuitry and that may be signaled by the circuitry to provide an indication that a successful bed-to-room association has been made.

In some embodiments, the indicator may comprise a light. The light may be turned on in response to the successful bed-to-room association being made and the light may be turned off in the absence of the successful bed-to-room association. The light may be illuminated a first color in response to the successful bed-to-room association being made and the light may be illuminated a second color in the absence of the successful bed-to-room association. The indication that a successful bed-to-room association has been made may be communicated to the circuitry from the locating and tracking system.

The hospital bed may further include an indicator module that may be attachable as a unit to the patient support structure. The indicator module may include a housing and the indicator may be carried by the housing. The circuitry may be carried by the housing. Alternatively or additionally, the indicator module may include module circuitry that may be in communication with the circuitry.

The hospital bed may have at least one other indicator. The at least one other indicator may include a communication indicator to indicate that a successful communication link has been established to a network of a healthcare facility. Alternatively or additionally, the at least one other indicator may include an alarm monitor indicator to indicate that one or more conditions of the hospital bed have been selected using a remote computer for monitoring of alarm conditions. Further alternatively or additionally, the at least one other indicator may include a signal strength indicator that may indicate a strength of a wireless communication link. For example, the signal strength indicator may comprise a multi-color light that may be illuminated different colors to indicate different levels of signal strength of the wireless communication link.

According to this disclosure, a method may include receiving at a first computer device that is remote from a bed, bed data transmitted from the bed. The method may include receiving at the first computer device, prospective bed-to-room association data transmitted from a second computer device to indicate that the bed is in a particular location, the second computer device may be included as part of a locating system. According to the method, after receiving the prospective bed-to-room association data, the first computer device may analyze the bed data to determine if it includes information indicating that a power cord of the bed is plugged into a power outlet. If the bed data includes information indicating that the power cord is plugged into a power outlet, the method includes storing the prospective bed-to-room association data in a database associated with the first computer device as finalized bed-to-room association data.

In some embodiments, the method further includes transmitting a message from the first computer device to the bed to notify the bed that a successful bed-to-room location has been made. Alternatively or additionally, the method includes indicating on the bed that a successful bed-to-room association has been made. For example, indicating on the bed that a successful bed-to-room association has been made may comprise illuminating a light on the bed and/or displaying location information on a graphical display of the bed.

The method may further comprise detecting at the bed that the power cord has become unplugged from the power outlet and ceasing indicating on the bed that a successful bed-to-room association has been made. The method may also comprise transmitting further bed data from the bed to the first computer device. The further bed data may include information indicating that the power cord is unplugged.

In some embodiments, the method may further include disassociating the bed from the particular location at the first computer device after receiving at the first computer device the further bed data including the information that the power cord is unplugged. The method may further comprise displaying on a display screen coupled to the first computer device information to indicate that the bed-to-room association no longer exists.

According to another aspect of the present disclosure, a system may include a bed that may have bed circuitry that may be configured to control bed functions, to receive wireless signals, and to transmit signals. The system may also include a heart rate monitor that may be worn by a patient. The heart rate monitor may have monitor circuitry that may be programmed to store a medical record number (MRN) of the patient. The monitor circuitry also may be configured to transmit the MRN wirelessly to the bed circuitry. The bed circuitry may be configured to transmit bed identification (ID) data and the MRN. A first remote computer device may be configured to receive the bed ID data and the MRN of the patient and may be configured to generate patient-to-bed association data for storage in a database based on the bed ID data and the MRN.

In some embodiments, the monitor circuitry also may be configured to transmit heart rate data to the bed circuitry. The bed circuitry may be configured to transmit the heart rate data to the first remote computer device. Alternatively or additionally, the bed circuitry may be configured to transmit the heart rate data to a second remote computer device. In some embodiments, the heart rate monitor may have an arm strap that may attach to an arm of the patient. Alternatively or additionally, the heart rate monitor may have a chest strap that may attach to a chest of the patient.

According to still a further aspect of this disclosure, a system includes a bed that may have bed circuitry that may be configured to control bed functions, to receive wireless signals, and to transmit signals. The system may include a heart rate monitor that may be worn by a patient. The heart rate monitor may have monitor circuitry that may store monitor identification (ID) data. The monitor circuitry may transmit the monitor ID data wirelessly to the bed circuitry. The bed circuitry may, in turn, transmit bed identification (ID) data and the monitor ID data. The system may further have a first remote computer device that may receive the bed ID data and the monitor ID data, that may correlate the monitor ID data with a medical record number (MRN) of the patient and that may generate patient-to-bed association data for storage in a database based on the bed ID data and the MRN.

In some embodiments, the monitor circuitry also may be configured to transmit heart rate data to the bed circuitry. In such embodiments, the bed circuitry may be configured to transmit the heart rate data to the first remote computer device. Alternatively or additionally, the bed circuitry may be configured to transmit the heart rate data to a second remote computer device. In some embodiments, the heart rate monitor may have an arm strap that attaches to an arm of the patient. Alternatively or additionally, the heart rate monitor may have a chest strap that attaches to a chest of the patient.

According to yet another aspect of this disclosure, a system may comprise a bed may have a first radio frequency (RF) communication module that may have first identification (ID) data. The first RF communication module may transmit bed data and the first ID data wirelessly from the bed. The bed may have a power cord that carries a transponder. The system may further include a second RF communication module that may be spaced from the bed and situated adjacent to a wall of a room in which the bed is located. The second RF communication module may have second ID data. The second RF communication module may receive the bed data and first ID data transmitted wirelessly from the first RF communication module of the bed.

The system may also have a transponder reader that may be situated adjacent to the wall of the room and that may be configured to read wireless information from the transponder including the first ID data. The system may include a communication circuit that is situated adjacent to the wall of the room. The communication circuit may be coupled to the transponder reader and coupled to the second RF communication module. The communication circuit may be configured to receive the first ID data from the transponder reader and to receive the second ID data from the second RF communication module. The communication circuit may pair the first and second RF communication modules so that the second RF communication module only accepts communication packets from the first RF communication module. Alternatively or additionally, the communication circuit may pair the first and second RF communication modules so that the communication board only accepts communication packets from the second RF communication module if the packets contain the first ID data.

In some embodiments, the bed may further include a Wi-Fi communication module. In such embodiments, the first RF communication module and the Wi-Fi communication module may be controlled so as to send wireless transmissions in different, non-overlapping time slots. In some embodiments, the communication circuit may be configured to send the bed data received via the first and second RF communication modules to a remote computer device.

The system may further have a data cable that may extend from the bed and which may be coupleable to the communication circuit. Thus, the communication circuit may receive the bed data transmitted by the bed over the data cable when the communication circuit is coupled to the data cable. The communication circuit may cease to accept bed data from the second RF communication module and may accept only the bed data transmitted over the data cable. In some embodiments, the bed may include a siderail and the first RF communication module may be coupled to the siderail.

The transponder may comprise an RFID tag, if desired. For example, the RFID tag may be molded into a plug body of the power cord or may be situated on a label attached to the power cord. The transponder reader may comprise a loop antenna. The loop antenna may be located adjacent a power outlet to which the power cord couples.

Further according to this disclosure, a system may include a bed that may have a first radio frequency (RF) communication module that may have first identification (ID) data and a second RF communication module that may have second ID data. The first and second RF communication modules may transmit bed data and the respective first and second ID data wirelessly from the bed. The bed may have a power cord that may carry a transponder. A third RF communication module may be spaced from the bed and situated adjacent to a wall of a room in which the bed is located. The third RF communication module may have third ID data. The third RF communication module may receive wireless transmissions from the first and second RF communication modules of the bed. The wireless transmissions may include the bed data and the respective first and second ID data transmitted wirelessly.

The system may further have a transponder reader that may be situated adjacent to the wall of the room and that may be configured to read wireless information from the transponder including the first ID data and the second ID data. A communication circuit of the system may be situated adjacent to the wall of the room. The communication circuit may be coupled to the transponder reader and may be coupled to the third RF communication module. The communication circuit may be configured to receive the first and second ID data from the transponder reader and to receive the third ID data from the second RF communication module. The communication circuit may pair the first and second RF communication modules with the third RF communication module so that the third RF communication module only accepts communication packets from the first communication module or the second communication module.

In some embodiments, the third RF communication module may be configured to assess signal strength of the wireless transmissions from the first and second RF communication modules and to communicate only with the first or second RF communication module that may have greater signal strength. Thus, the third RF communication module may operate as a master and the first and second RF communication modules may each operate as a slave. If the third RF communication module is unable to communicate with the first and second RF communication modules, then an alarm may be triggered by the third RF communication module.

In some embodiments, the bed may further include a Wi-Fi communication module. The first and second RF communication modules and the Wi-Fi communication module may be controlled so as to send wireless transmissions in different, non-overlapping time slots. The communication circuit may be configured to send the bed data received via the third RF communication module to a remote computer device.

The system may further include a data cable which may extend from the bed and which may be coupleable to the communication circuit. The communication circuit may receive the bed data transmitted by the bed over the data cable when the communication circuit is coupled to the data cable. The communication circuit may be configured to cease accepting bed data from the third RF communication module and to accept the bed data transmitted over the data cable. The bed may include a first siderail and a second siderail. The first RF communication module may be coupled to the first siderail and the second RF communication module may be coupled to the second siderail.

In the system having the first, second and third communication modules, the transponder may comprise an RFID tag such as one molded into a plug body of the power cord or on a label attached to the power cord. In such a system, the transponder reader may comprises a loop antenna such as one that may be located adjacent a power outlet to which the power cord couples.

Still further according to this disclosure, a bed-to-room association system may comprise a bed that may have a power cord that may carry a first RFID component and a receptacle module that may carry a second RFID component. The receptacle module may have a receptacle into which the power cord may plug to receive power and to bring the first and second RFID components into communicative proximity. The receptacle module may have an indicator that may be activated in response to successful communication being established between the first and second RFID components.

In some embodiments, the indicator may comprise a light. The light may comprise a light ring, for example. The light ring may surround the receptacle. The first RFID component may comprise one of an RFID tag and an RFID reader and the second RFID component may comprise another of the RFID tag and RFID reader.

Also according to this disclosure, an apparatus for communicating with a nurse call system of a healthcare facility may be provided. The apparatus may include a bed that may have a first transceiver for wireless communication of bed identification (ID) data and bed status data. The apparatus may also include a handheld pillow speaker unit that may have a second transceiver in wireless communication with the first transceiver. The pillow speaker unit may be in hardwired communication with the nurse call system. Thus, the pillow speaker unit may serve as a communication intermediary between the bed and the nurse call system.

In some embodiments, the apparatus may further include an interface unit that may be fixed with respect to a wall in a patient room. The pillow speaker unit may have a cable with a plug that may plug into the interface unit. The interface unit may be communicatively coupled to the nurse call system.

The pillow speaker unit may include a first set of user inputs that may be used to control at least one of the following: a television, a room light, and at least one window shade. The bed may include a second set of user inputs that may be used to control at least one of the following: the television, the room light, and the at least one window shade.

In some embodiments, use of the second set of user inputs may be communicated from the first transceiver of the bed to the second transceiver of the pillow speaker unit. Thus, the pillow speaker unit may include user inputs that are used to control bed functions.

It is contemplated by this disclosure that the pillow speaker unit may include a set of manual buttons and a touchscreen graphical display that displays electronic buttons. The manual buttons may include at least one of the following: a nurse call button, a reading light button, and a room light button. The manual buttons may further include at least one of the following: a television control button, a radio control button, and a telephone dial pad button. The electronic buttons may include buttons that may be used to send distinct preprogrammed messages to at least one caregiver. At least one of the manual buttons and at least one of the electronic buttons may control a same function.

According to a further aspect of the present disclosure, a pillow speaker unit that may communicate with a nurse call system in a healthcare facility is provided. The pillow speaker unit may include a handheld housing, a set of manual buttons that may be accessible on the housing, and a touchscreen graphical display that may display electronic buttons. At least one of the manual buttons and at least one of the electronic buttons may be usable to send a respective signal to the nurse call system. The pillow speaker unit may include the features discussed previously.

Additional features, which alone or in combination with any other feature(s), such as those listed above and/or those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which:

FIG. 19 is a diagrammatic view showing a patient-to-bed association system in which a wireless heart rate monitor sends data, including the patient's medical record number (MRN), to circuitry of a hospital bed which, in turn, transmits the patient's MRN and a bed ID for used by a remote computer device to associate the patient to the bed;

DETAILED DESCRIPTION

Figure 15:
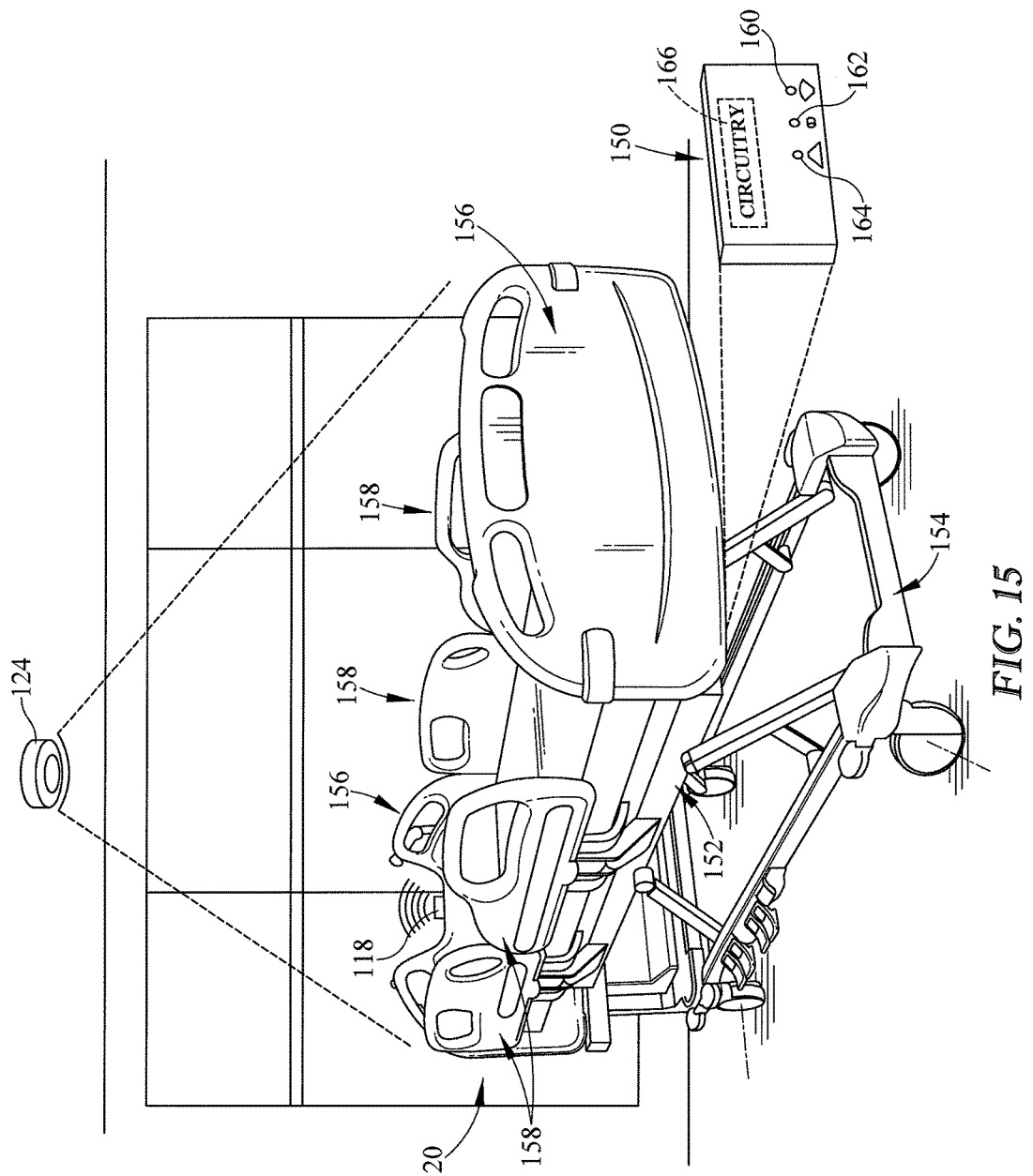
FIG. 15 is a perspective view showing an indicator module exploded away from a hospital bed, the indicator module having three LED's, one of which is illuminated to indicate that a successful bed-to-room association has been made.
Figure 16:
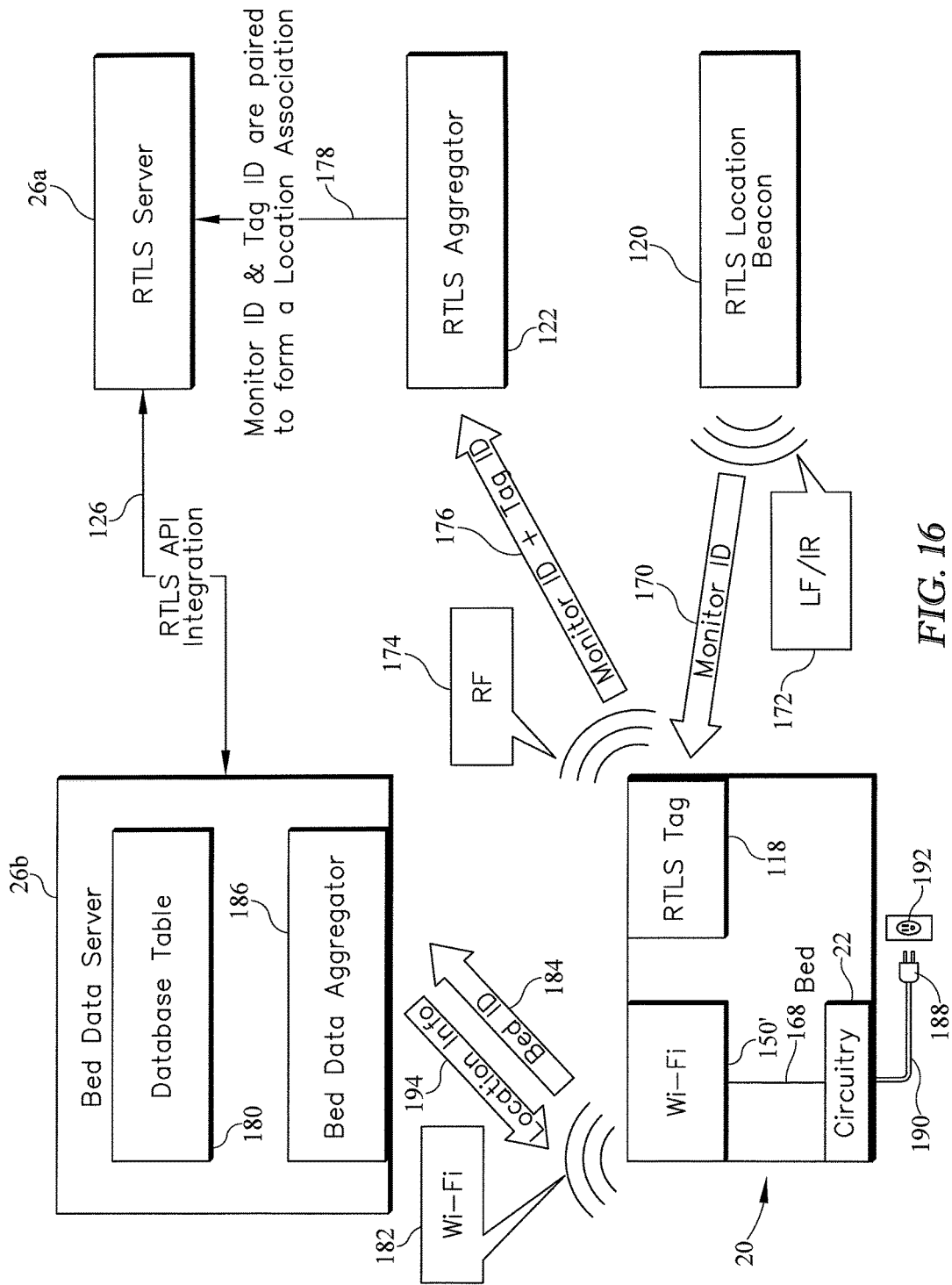
FIG. 16 is a block diagram of a wireless bed-to-room association system similar to that of FIG. 12 showing that location information is transmitted from a remote server to the circuitry of the hospital bed.
Figure 20:
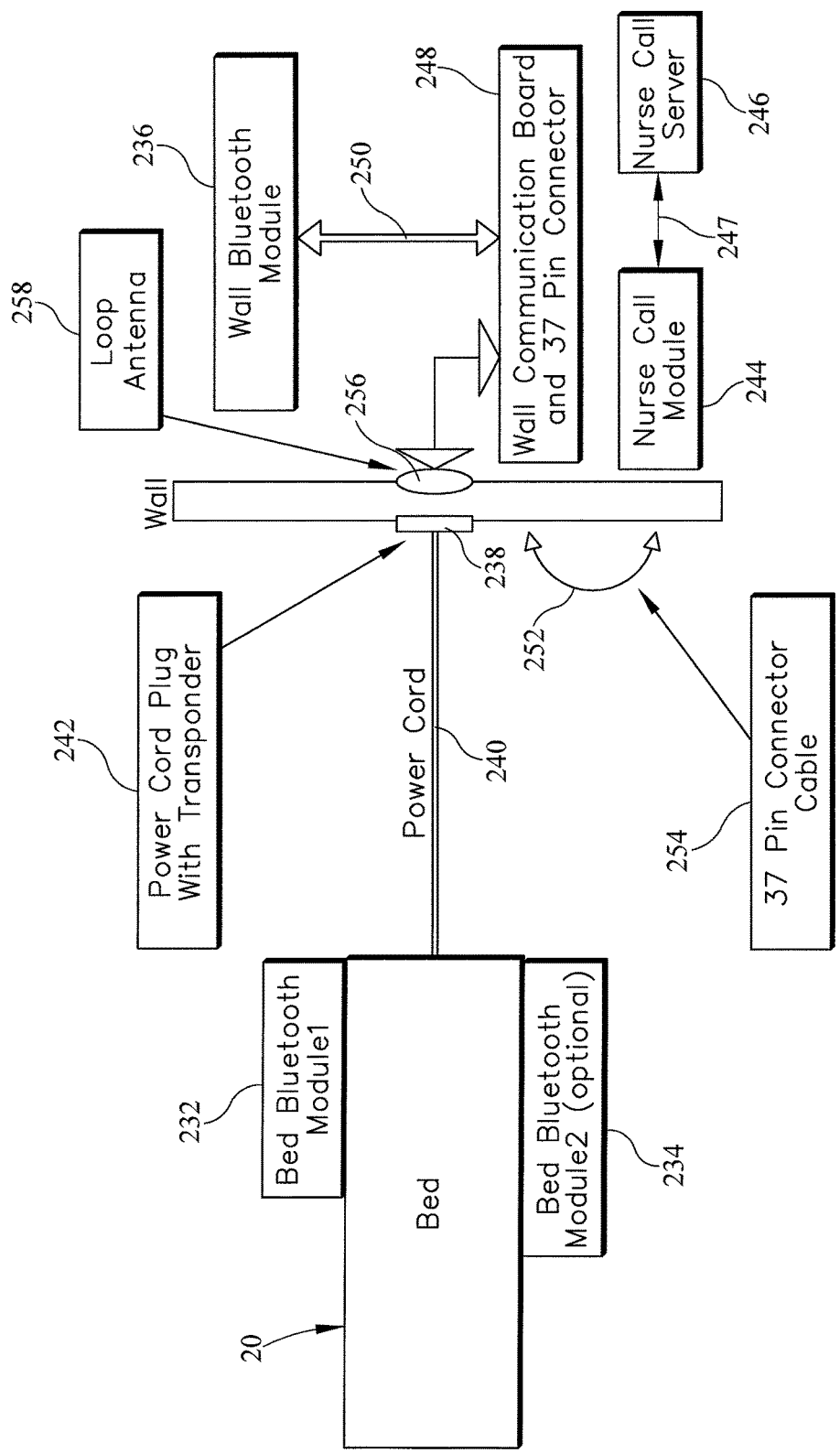
FIG. 20 is a block diagram of another bed data system in which a bed equipped with one or two bed Bluetooth (BT) modules communicates with a wall BT module for transmission of bed data after a BT pairing operation is conducted based on transmission of bed BT module ID data via a transponder carried by a plug of a power cord of the hospital bed.
Figure 25:
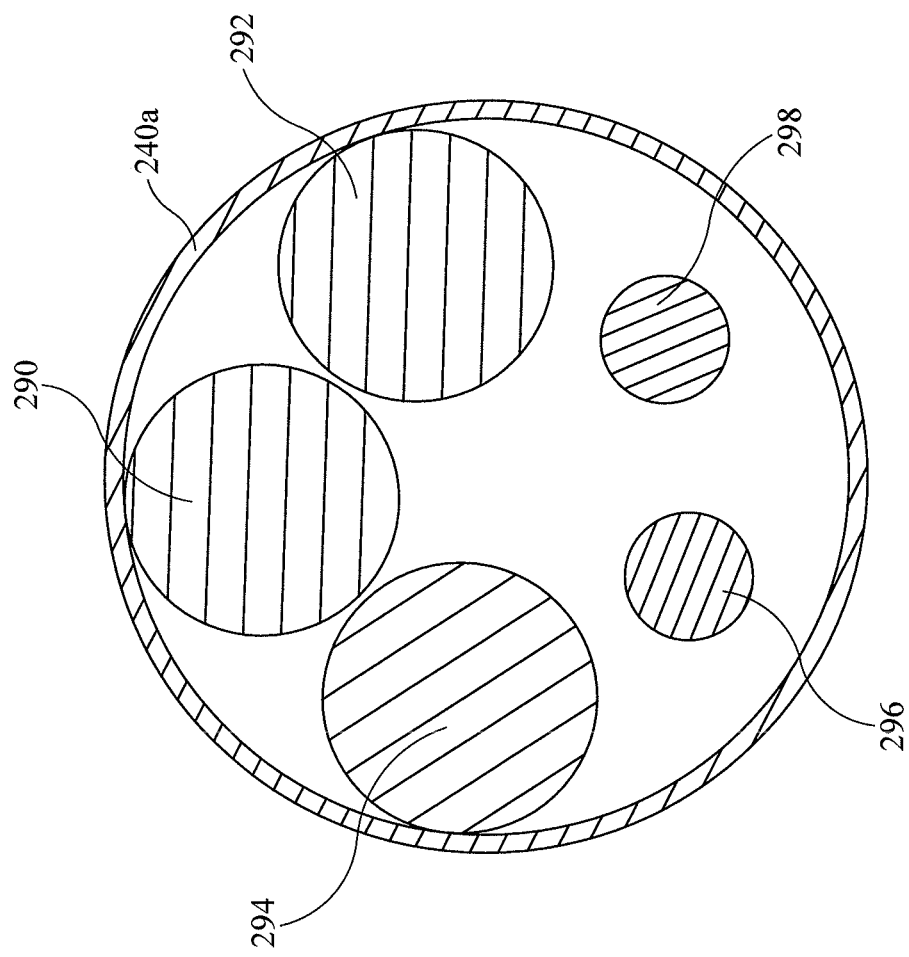
FIG. 25 is a diagrammatic cross-sectional view of the AC cord of FIGS. 23 and 24.
Figure 26:
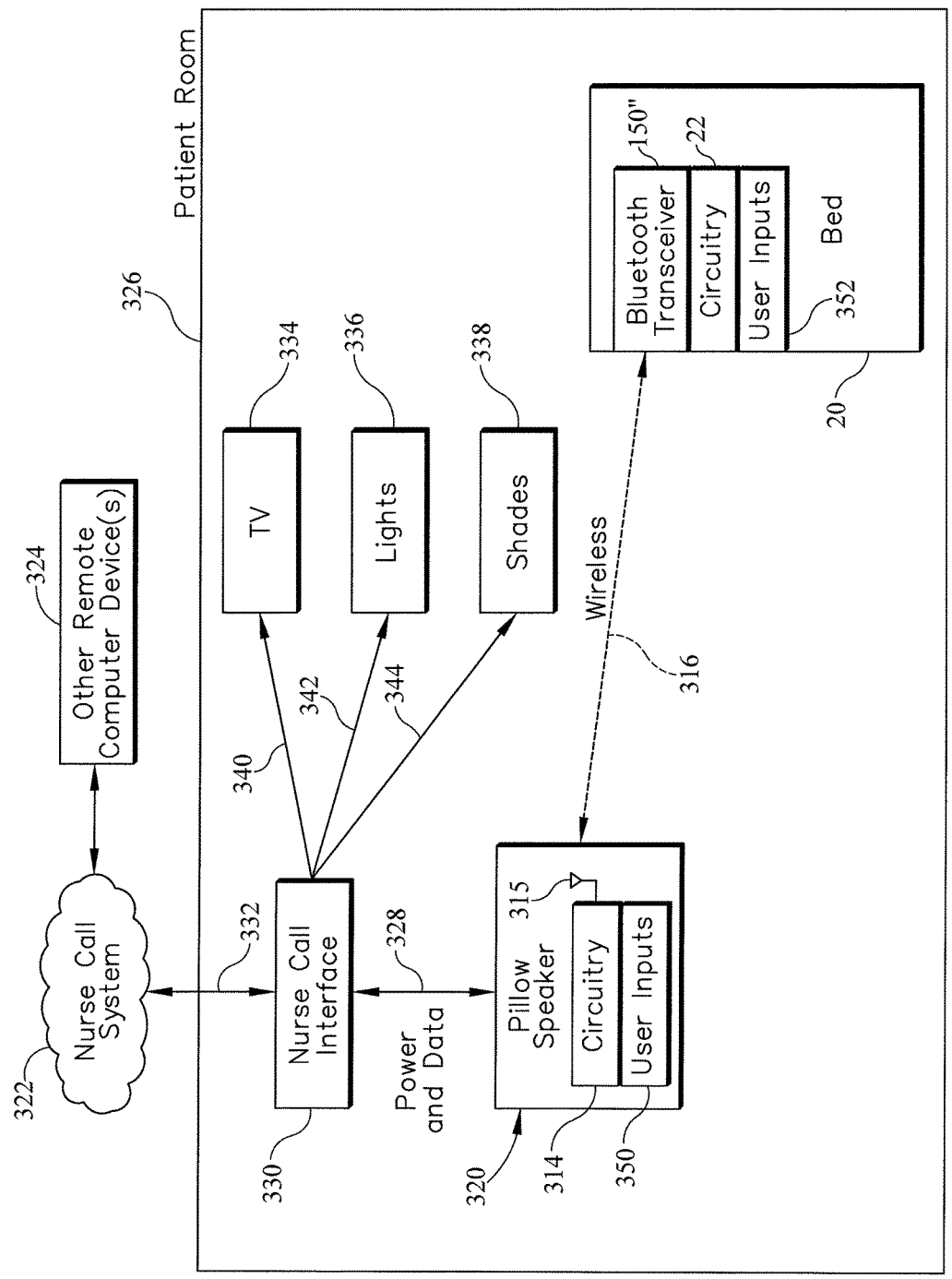
FIG. 26 is a diagrammatic view of a further bed-to-room association system in which wireless communication is established between circuitry of a bed and a handheld pillow speaker which acts as a communication intermediary between the bed and a nurse call system as well as one or more other remote computer devices.

Throughout FIGS. 1-28, a bed 20 has circuitry 22 that transmits data of various types in various embodiments as discussed below via a network 24 to one or more remote computer devices 26. FIGS. 1-4, 13 and 14 each show a diagrammatic transmitter 28 that is coupled to, or included as part of, circuitry 22. It should be understood that each bed 20 has a transmitter of some type, such as illustrative transmitter 28 which, in some embodiments, is included as part of a transceiver. It is contemplated by this disclosure that transmitter 28 transmits data wirelessly, but that is not to say that transmitter 28 is excluded from sending data over a wired connection to network 24 in contemplated embodiments, if desired. In FIGS. 15 and 16, modules 150, 150', respectively, are included on bed 20 and have wireless communication capability. In FIG. 20, a first module 232 and an optional, second module 234 are included on bed 20 and have wireless communication capability. In FIG. 26, bed 20 has a module 150" with wireless communication capability.

While circuitry 22 is shown in the various figures as a single diagrammatic block, it should be understood that the single block is intended to represent all of the circuitry found on a patient bed and such circuitry may be embodied in separate, but interconnected, modules and/or circuit boards. In other words, circuitry 22 of patient bed 20 comprises a large complex circuit. See, for example, "Service Manual, Progressa™ Bed From Hill-Rom," © 2013, Hill-Rom Services, Inc.; "Service Manual, TotalCare® Bed System From Hill-Rom," © 2008, Hill-Rom Services, Inc.; and "Service Manual, VersaCare® Bed From Hill-Rom," 2008, Hill-Rom Services, Inc.; each of which is hereby incorporated by reference herein. See also U.S. Pat. Nos. 5,771,511 and 7,506,390, each of which is hereby incorporated by reference herein.

Furthermore, network 24 (aka Ethernet 24 in FIGS. 13 and 14) is represented diagrammatically by a cloud image in the various figures. This image is intended to represent all of the hardware components and software that make up various types of networks in a healthcare facility. The architecture and functionality of such networks can vary widely. Suffice it to say that, in some embodiments, the networks 24 contemplated herein have wireless access points for wireless connectivity to the network by various devices, including bed 20. Alternatively or additionally, networks 24 contemplated herein have ports, such as ports that receive RJ-45 connectors, for wired connection of various devices, including bed 20, to the respective network 45. Thus, network 24 includes, for example, computer devices such as nurse call computers, electronic medical records (EMR) computers, admission/discharge/transfer (ADT) computers, and the like. Examples of the type of communication equipment included in various embodiments of a nurse call system (as well as network 24, in general) can be found in U.S. Pat. Nos. 8,598,995; 8,384,526; 8,169,304; 8,046,625; 7,746,218; 7,538,659; 7,319,386; 7,242,308; 6,897,780; 6,362,725; 6,147,592; 5,838,223; 5,699,038 and 5,561,412, all of which are hereby incorporated by reference herein in their entirety to the extent that they are not inconsistent with the present disclosure which shall control as to any inconsistencies.

The various embodiments disclosed herein relate to systems and methods for making bed-to-room associations in a healthcare facility. This is accomplished by associating a bed identifier (ID) and a location identifier (ID) in a database of a computer device 26, such as a server or other computer. The term "room" in the phrase "bed-to-room" is intended to include not just patient rooms, but also hallways, service areas, supply rooms, elevators, cleaning rooms, and any other location in a healthcare facility which may be occupied by a bed. In each of the embodiments disclosed herein, other types of data may also be associated with the bed and/or room in the database, such as a patient ID, bed status data, data from other types of medical equipment (e.g., IV pumps, therapy equipment, vital signs equipment, and so forth), and data from other medical systems (e.g., electronic medical records (EMR) system, admission/discharge/transfer (ADT) system, pharmacy system, laboratory system, and so forth). Thus, patient-to-room; patient-to-bed; and patient-to-bed-to-room systems and methods are contemplated herein. It should also be appreciated that the order of association makes no difference and that "bed-to-room" and "room-to-bed" associations mean the same thing and that "patient-to-bed-to-room" and "room-to-patient-to-bed" associations mean the same thing, just to give a couple examples.

Figure 1:
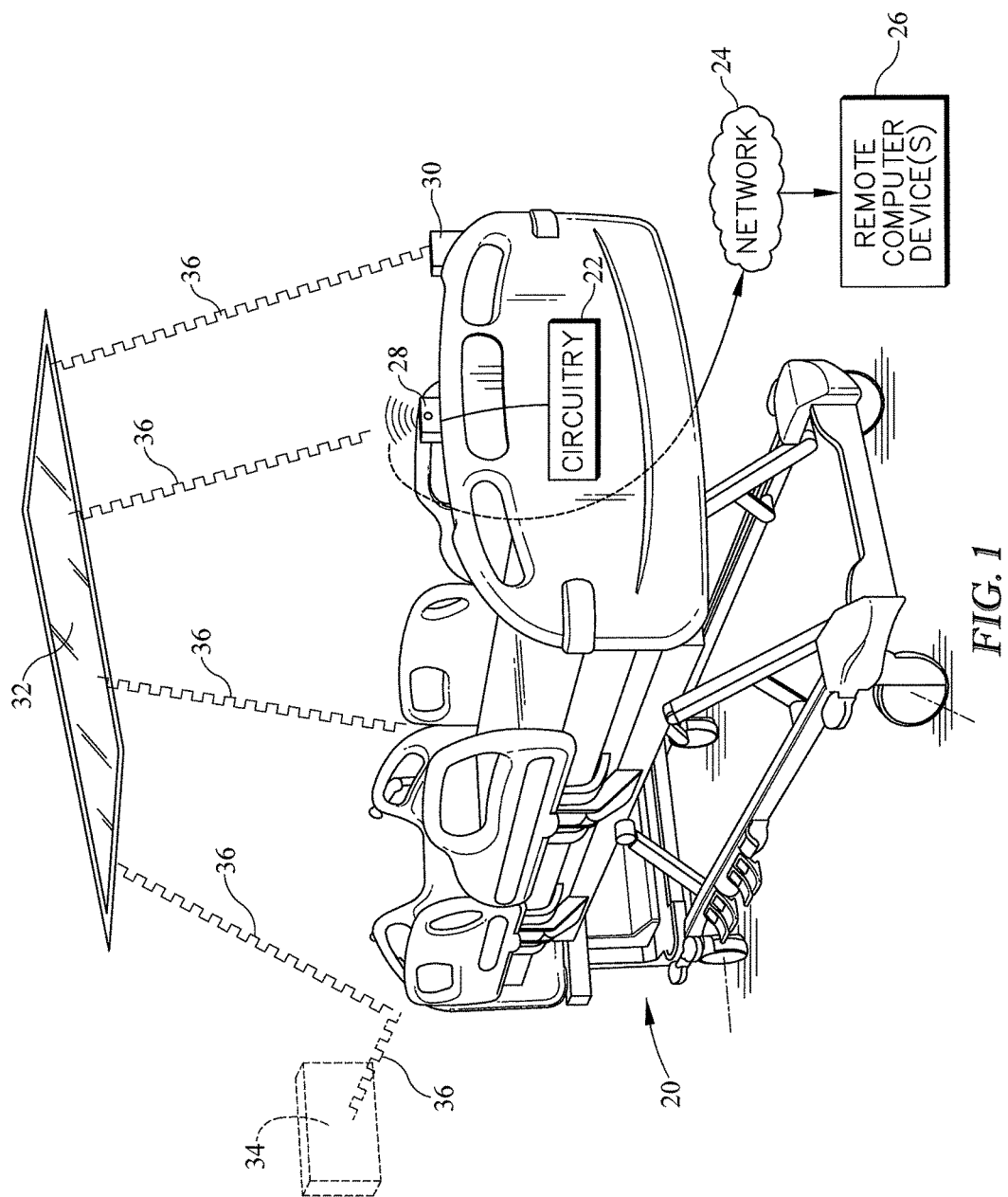
FIG. 1 is perspective view of a patient bed having a sensor that receives light emitted from an overhead display screen (in solid) or from a wall-mounted display screen (in phantom), the light having a signature (indicated diagrammatically via a square wave) that is unique for the location occupied by the bed, the bed having circuitry (shown diagrammatically) that analyzes the signature and transmits data corresponding to the signature and transmits a bed identifier (ID) to one or more remote computer devices (shown diagrammatically) via a network (shown diagrammatically)

Referring now to FIG. 1, bed 20 has a sensor 30 that receives light emitted from an overhead display screen 32. In an alternative embodiment, screen 32 is omitted and the light received by sensor 30 is emitted from a wall-mounted display 34 screen (in phantom). Screen 32, in some embodiment, us operated to display one or more nature scenes that are conducive to a patients recovery and/or one or more night sky scenes that are conducive to helping the patient fall asleep. Screen 34, in some embodiments, is included as part of a room station of a nurse call system or as part of some other computer device in the room.

The light emitted from screens 32, 34 is visible light that has a signature 36 (indicated diagrammatically via a square wave). The signature 36 is unique for the location occupied by the bed 20. That is, the signature of the light emitted from screens 32, 34 is different for different rooms. Circuitry 30 is coupled to sensor 30 and analyzes the emitted light to determine its signature 36. In some embodiments, sensor 30 comprises a camera and in other embodiments, sensor 30 comprises a red-green-blue (RGB) image sensor chip. The signature 36 is emitted at a specified wavelength and/or at a specified pulsed frequency. The pulsed frequency is sufficiently large and/or the wavelength is sufficiently short in duration so as to be imperceptible to human vision. The specified wavelength and/or the specified pulse frequency is unique to each room. Thus, by analyzing the emitted light to determine the signature 36, data corresponding to the signature 36 is usable to determine the location of bed 20 in the associated healthcare facility.

Circuitry 22 commands transmitter 28 to transmit data corresponding to the signature and also commands transmitter 28 to transmit a bed identifier (ID) to at least one remote computer device 26 via a network 24. Typically, the data corresponding to the signature and the bed ID are included in the same message packet. The remote computer device 26 then makes the bed-to-room association based on the data corresponding to the signature and the bed ID. Thus, the remote computer device 26 includes a table or other similar type of relational database that correlates the data corresponding to the signature with a particular location, such as a patient room number, in the healthcare facility.

Figure 2:
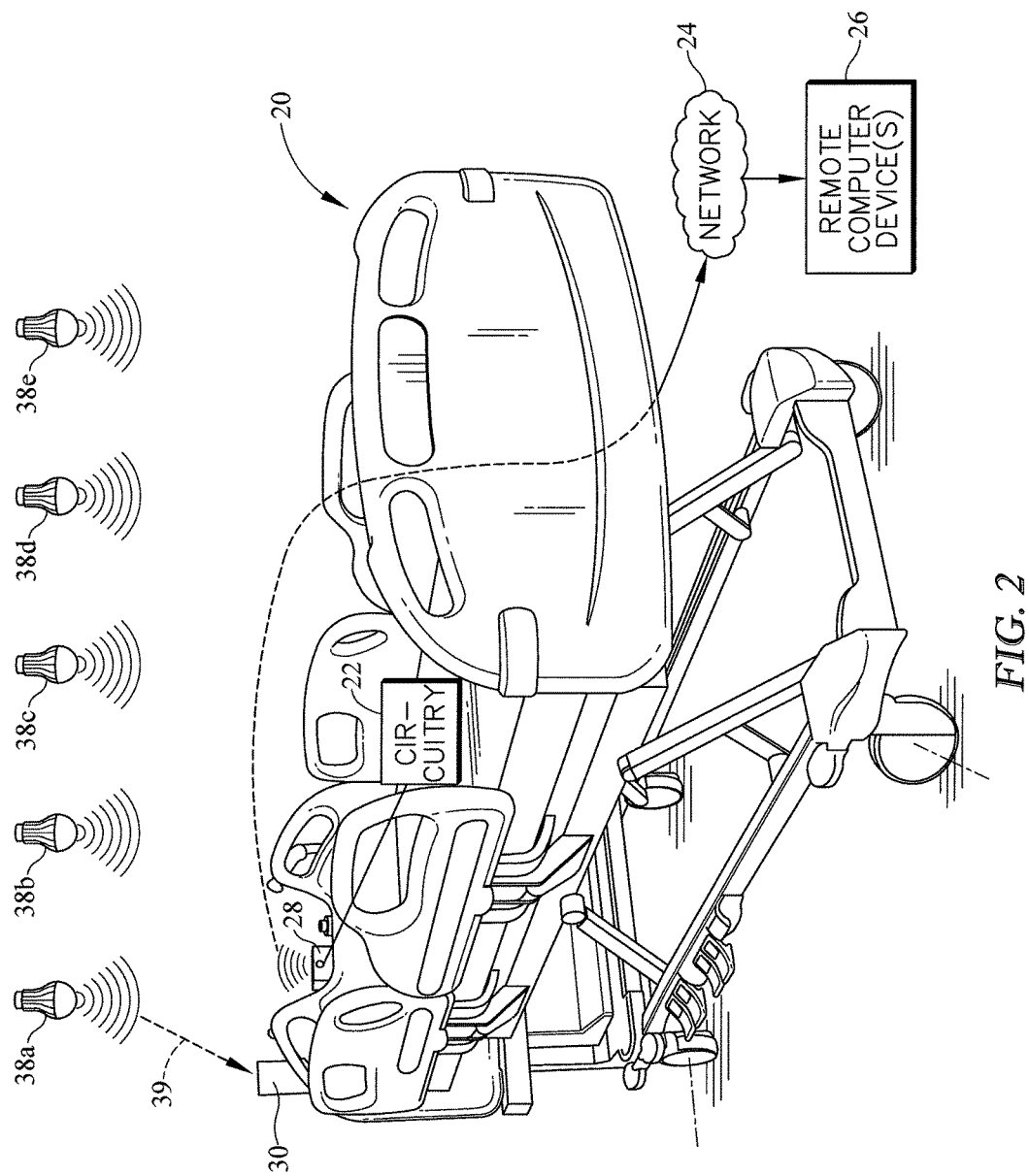
FIG. 2 is a diagrammatic perspective view showing a number of light bulbs that each emit light having a unique signature, each bulb being associated with a different room, and showing a sensor receiving the light and signature from a first bulb, the bed having circuitry that analyzes the signature and transmits data corresponding to the signature and transmits a bed ID to one or more remote computer devices via the network.

Referring now to FIG. 2, light bulbs 38a-e are shown diagrammatically and each light bulb 38a-e emits light having a unique signature. It should be understood that each bulb 38a-e is located in a different room of the healthcare facility. In the illustrative example of FIG. 2, bulb 38a is in communication with bed 20. Thus, sensor 30 receives the light and signature from a first bulb 32a as indicated diagrammatically in FIG. 2 with dashed arrow 39. Just like the embodiment of FIG. 1, circuitry 22 of bed 20 analyzes the emitted light to determine the signature and transmits data corresponding to the signature and transmits bed ID to at least one remote computer device 36 via the network 24 and computer device 36 makes the bed-to-room association based on the received signature data and bed ID.

In some embodiments, bulbs 38a-e are high-power white LED lightbulbs that are programmable to emit a specified wavelength at a specified pulsed frequency. For example, bulbs 38 are programmable to emit different percentages of blue, red and green light (e.g., 11% blue, 30% red, and 59% green) which still appear generally as white light. In some embodiments, the bulb 38a-e in each room emit the same percentage of blue, red and green light, but at a different pulsed frequency for each room. In some embodiments, sensor 30 is embodied as a simple photovoltaic sensor and the unique light signatures are created by varying a power duty cycle of the associated light source without regard to wavelength. For example, the light source is turned on and off (e.g., flickered) at a specified frequency which is imperceptible to human vision but which is unique to each room.

Suitable programmable bulbs 38a-e are available from ByteLight of Boston, Mass. See also, U.S. Pat. Nos. 8,520,065; 8,457,502; 8,436,896; 8,432,438; 8,416,290; 8,334,901; 8,334,898; and 8,248,467; each of which is hereby incorporated by reference herein.

In some embodiments, in order to enable locating to take place in rooms that have the light source turned off, a source of infrared (IR) light is emitted with a signature and sensed by sensor 30. The processing thereafter is the same as described above with regard to signatures included in the light emitted from screens 32, 34 and bulbs 38a-e. The IR light pulses, in some embodiments, are at a lower frequency which is possible because IR light is not visible to humans anyway. Thus, a visible light signature and an IR light signature may each indicate the same room, although their pulsed frequencies are different. In other embodiments, the IR light pulses are at the same pulsed frequency as the visible light pulses. In any event, it should be understood that the IR light signatures are different from room to room.

A lower amount of power is used to drive the IR light sources when the light sources of visible and IR light are in night mode. While it is possible for the IR light source to be separate from the light sources described above, it is contemplated by this disclosure that the IR light source is included in the same light source that emits visible light when in the on state. In such embodiments, when the visible light source is turned on, some of the applied power is stored in a battery or capacitor or other energy storage device and is used to drive the IR light source after the visible light source is turned off. In some embodiment, therefore, the IR light source only operates when the visible light is turned off. In other embodiments, the IR light source operates all the time.

In some embodiments, bed 20 includes two sensors 30, one for the visible light and one for the IR light. However, combined RGB and IR image or light sensors are known in the art. See, for example, U.S. Patent Application Publication No. 2010/00289885 which is hereby incorporated by reference herein. Such a device or similar such devices may be used as the sensor 30 of bed 20 if desired.

Figure 3:
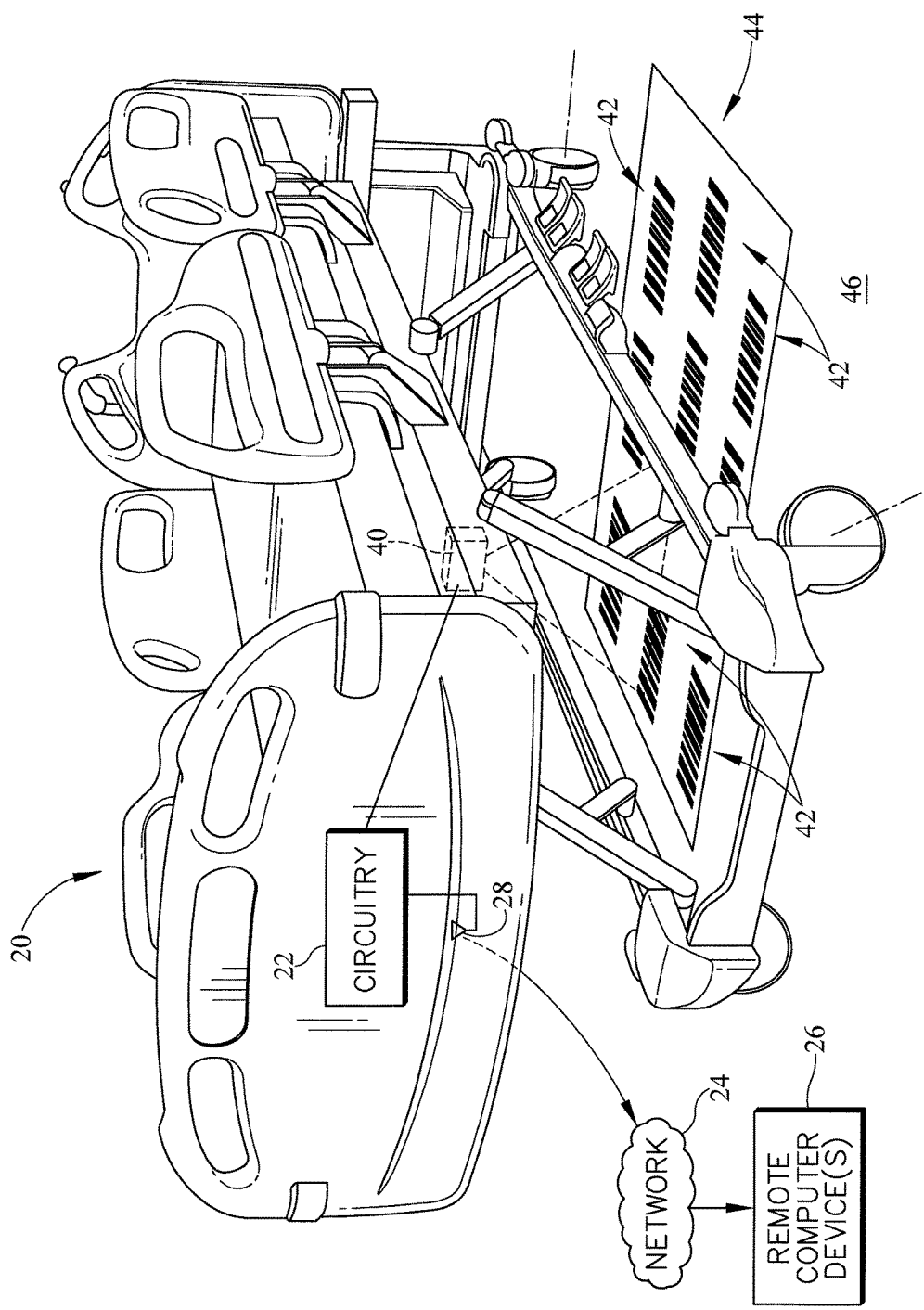
FIG. 3 is a perspective view of an alternative embodiment of a patient bed having a bar code scanner (shown diagrammatically) that scans at least one bar code of an array of redundant bar codes that is affixed to a floor surface, the bed having circuitry (shown diagrammatically) that is coupled to the bar code scanner and that transmits data corresponding to the at least one bar code and bed ID to the network.

Referring now to FIG. 3, bed 20 has a bar code scanner 40 that scans at least one bar code 42 of an array 44 of redundant bar codes 42 that are affixed to a floor surface 46 of other horizontal surface. In some embodiments, array 44 of bar codes 42 is included on a floor mat that lies on the floor 46 and, in other embodiments, array 44 of bar codes 42 is included on a label that sticks to the floor 46. In still other embodiments, bar codes 42 are included on one or more floor tiles that form part of the floor surface. Circuitry 22 commands transmitter 28 to transmit data corresponding to the at least one bar code 42 and a bed ID to one or more remote computer devices 26 via the network 24. The bedto-room association is then made by the remote computer device 26 based on the data corresponding to the at least one bar code 42 and the bed ID. Having redundant bar codes 42 is an improvement over prior art system that may have only one bar code to be read by a bar code scanner. This is because the bed 20 does not need to be as precisely placed within the hospital room. Scanner 40 just needs to read one of the bar codes 42 of the array 44. In the illustrative example of FIG. 3, scanner 40 is mounted to an upper frame of the overall bedframe of bed 20 and scans downwardly through a large opening defined by frame members of a base frame of the bedframe of bed 20.

Figure 4:
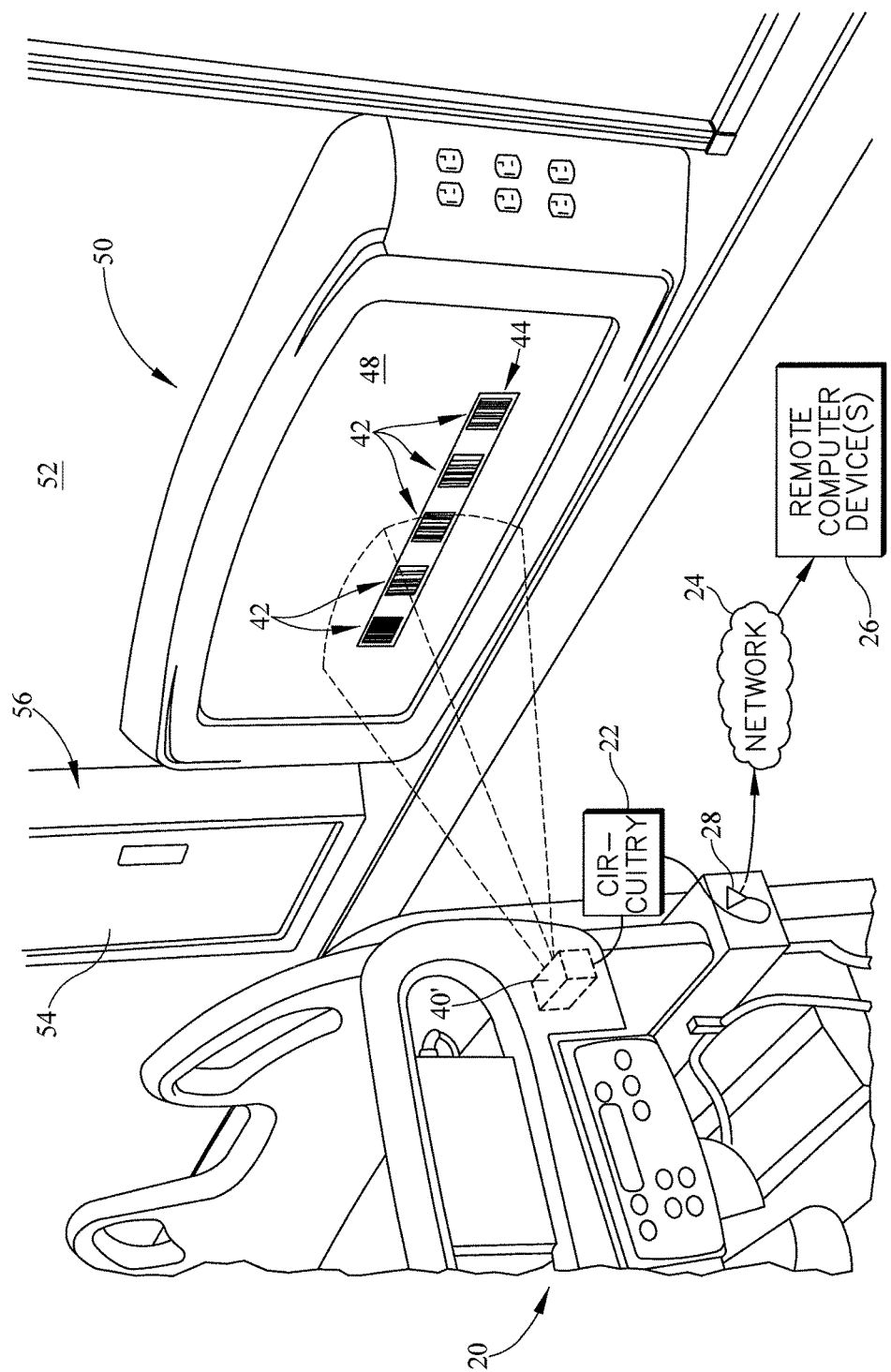
FIG. 4 is a partial perspective view of a bed, similar to that of FIG. 3, having a bar code scanner (shown diagrammatically) that scans at least one bar code of an array of redundant bar codes that is affixed to a vertical surface of a bed locator unit, the bed having circuitry (shown diagrammatically) that is coupled to the bar code scanner and that transmits data corresponding to the at least one bar code and bed ID to the network.

Referring now to FIG. 4, bed 20 has a bar code scanner 40' mounted to its upper frame and arranged to scan at least one bar code 42 of an array 44 of redundant bar codes 42 that is affixed to a vertical surface 48 of a bed locator unit 50 that is mounted to a room wall 52. In other embodiments, array 44 is affixed to room wall 52 or to a panel 54 of a piece of architectural equipment, such as, for example, the illustrative column 56, a headwall unit or an arm. Circuitry 22 commands transmitter 28 to transmit data corresponding to the at least one bar code 42 read by scanner 40' and a bed ID to one or more remote computer devices 26 via the network 24. The bed-to-room association is then made by the remote computer device 26 based on the data corresponding to the at least one bar code 42 and the bed ID. Having redundant bar codes 42 on a vertical surface, such as illustrative surface 48, is an improvement over prior art system that may have only one bar code to be read by a bar code scanner. By having redundant bar codes 42, the bed 20 does not need to be as precisely placed within the hospital room. Scanner 40' just needs to read one of the bar codes 42 of the array 44. In the illustrative example of FIG. 4, scanner 40' is mounted to an upper frame of the overall bedframe of bed 20 and scans generally horizontally outwardly from a head end of the bed 20.

Although only one row is included in the array 44 of FIG. 4, it will be appreciated that multiple rows are within the scope of this disclosure. Having multiple rows permits upper frame of bed 20 to be adjusted many different heights and yet scanner 40' can still read one of the bar codes 42 of the multi-rom array. Furthermore, while array 44 of FIG. 44 has five bar codes 42 and while each row of array 44 of FIG. 3 has three bar codes, embodiments having more or less bar codes 42 than three or five in any given row are within the scope of this disclosure. Moreover, arrays 42 having any number of rows greater than one are within the scope of this disclosure, the upper limit being bounded primarily by the size of the bar codes 42 and the size of the surface against which the array 44 is placed.

Figure 5:
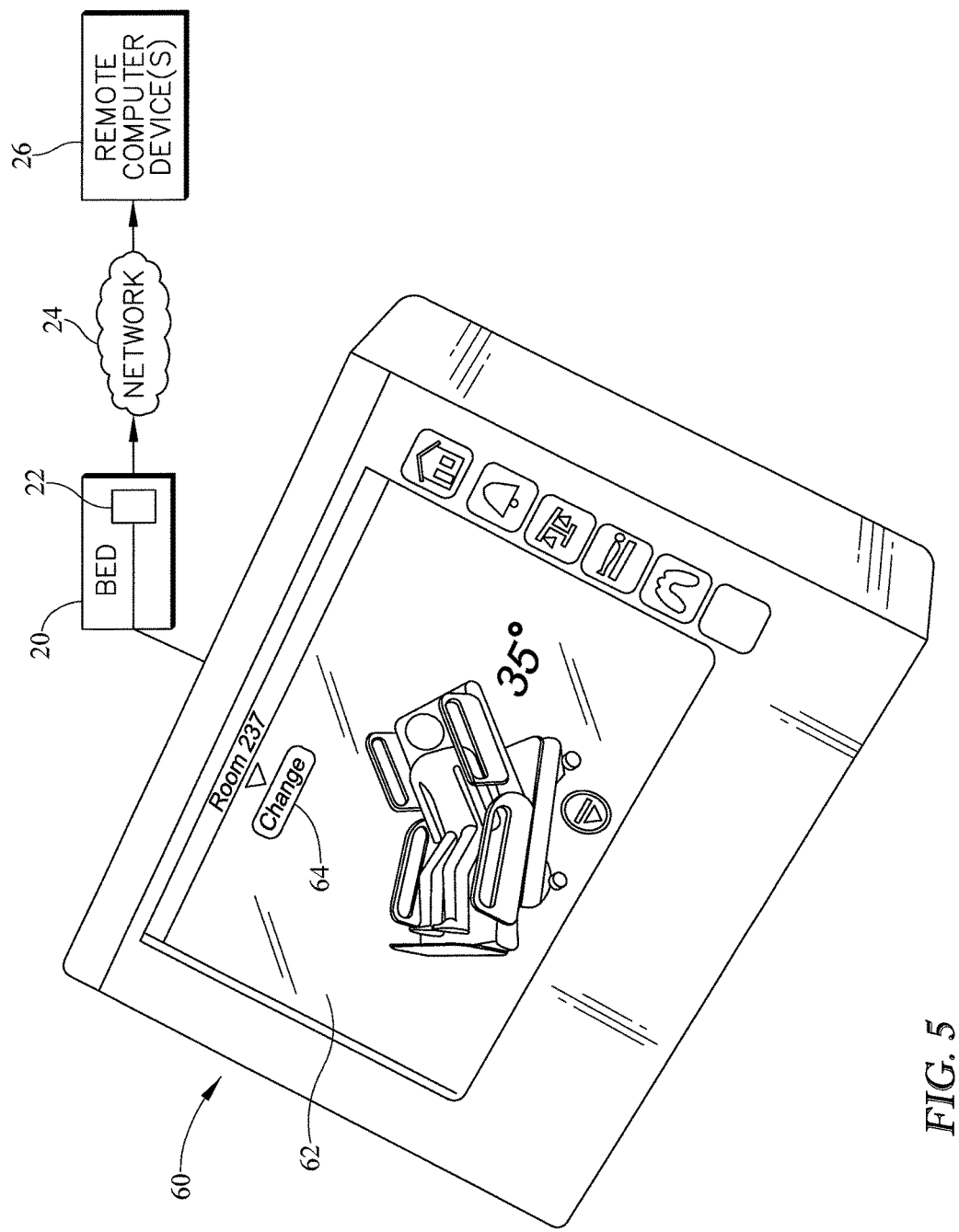
FIG. 5 is a diagrammatic view showing a graphical user interface (GUI) of a bed having a touch screen display that displays a room number and a change button, the bed being coupled to one or more remote computer devices via a network and the bed transmitting the room number and a bed ID to the one or more remote computer devices via the network.
Figure 6:
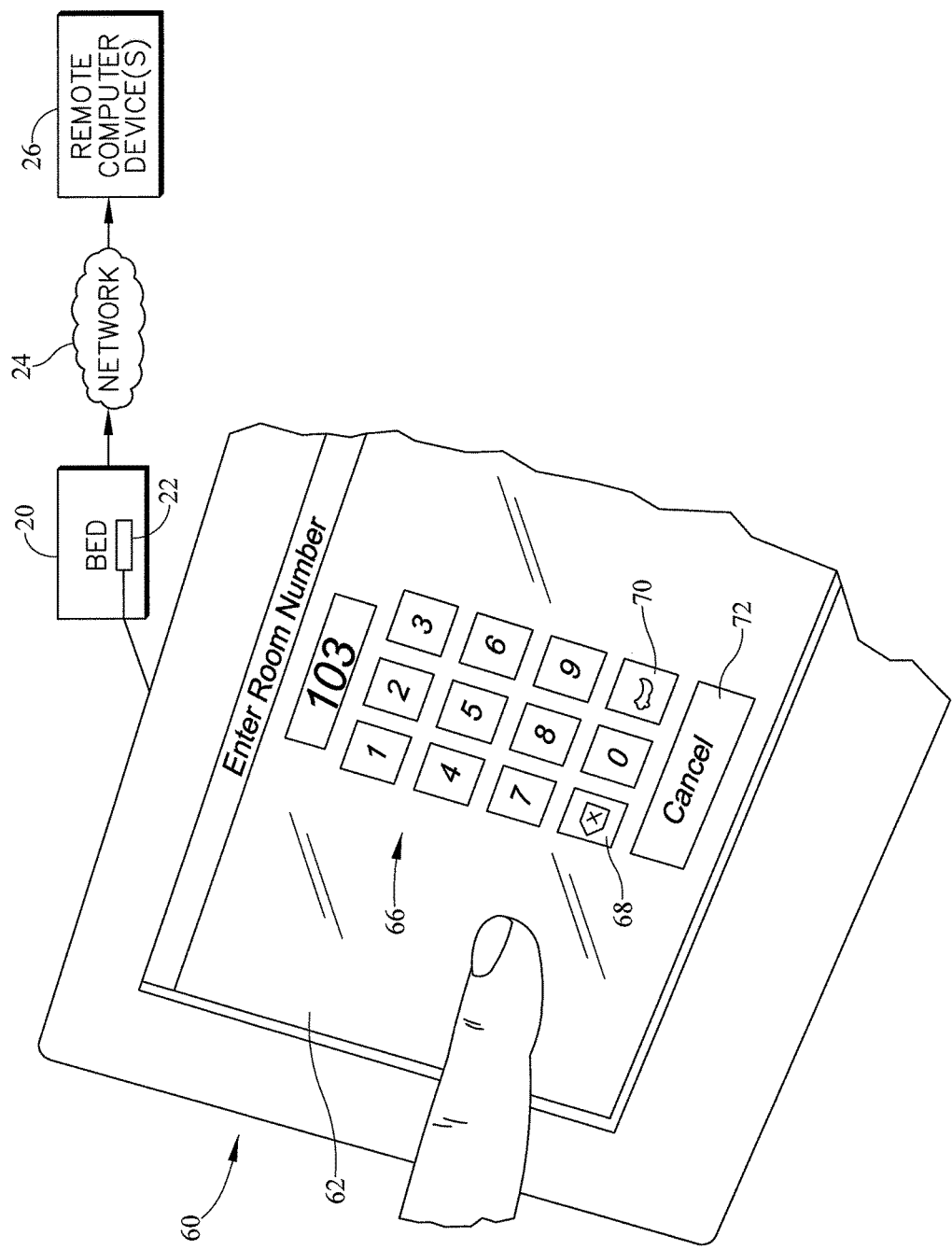
FIG. 6 is a diagrammatic view, similar to FIG. 5, showing a keypad that appears on the GUI after selection of the change button, the keypad being usable by a caregiver to enter a new room number corresponding to a new location of the bed.
Figure 7:
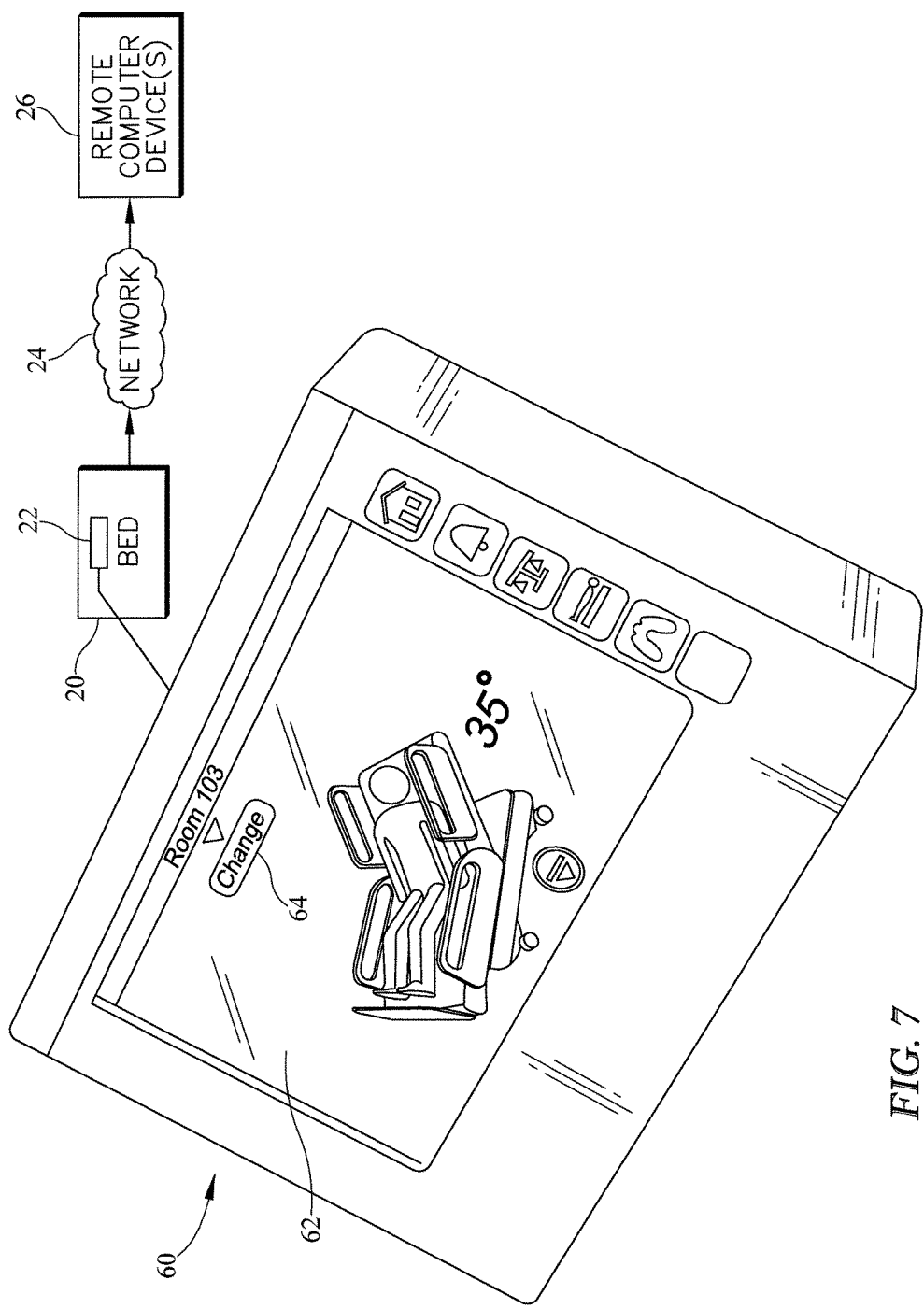
FIG. 7 is a diagrammatic view, similar to FIG. 5, showing the new room number being displayed on the GUI, the new room number and bed ID being transmitted by the bed to the one or more remote computer devices via the network.

Referring now to FIGS. 5-7, in an alternative embodiment according to this disclosure, bed 20 has a graphical user interface (GUI) 60 with a touch screen display 62 that displays a current room number, here "237," and a change button 64 on a home screen as shown in FIG. 5. As with the other embodiments disclosed herein, bed 20 of FIGS. 5-7 is coupled to one or more remote computer devices 26 via network 24 and the remote computer device(s) 26 make bed-to-room associations based on received location ID and bed ID.

In response to a caregiver selecting change button 64 on GUI 60, a keypad 66 appears on the GUI 60. The text "Enter Room Number" appears above keypad 66 in the illustrative example to suggest to the caregiver that a new room number be entered into the memory of circuitry 22 to replace the old room number. In the illustrative example, keypad 66 includes buttons having numbers 0-9 arranged in similar manner as a standard telephone, a back button 68, an enter button 70, and cancel button 72. In other embodiments an alphanumeric keyboard is provided to permit the user to indicate whether the bed is at an "A" location or a "B" location in a semi-private room for example.

Keypad 66 is used by a caregiver to enter the room number in which bed 20 is located into the memory of circuitry 22 of bed 20. Circuitry 22 of bed 20 then transmits the room number in any suitable format along with the bed ID to one or more remote computer devices 26 via network 24. Thus, the room number manually entered by the user or caregiver serves as the location ID for the respective bed 20. Bed 20 does not rely on any external device or artifact (e.g., light source, locator unit, bar code label, etc.) for obtaining the location ID to be transmitted from the bed 20. Accordingly, the embodiment of FIGS. 5-7, as well as the alternative embodiment of FIGS. 8-11 discussed below, are the lowest cost embodiments contemplated by this disclosure.

In the example of FIG. 6, the caregiver has entered a new room number, here "103," using keypad 66. If the caregiver wishes to revise the entered number, the back button 68 is selected and a revised digit can be entered by the caregiver using one of the numeric keys of keypad 66. If the caregiver is satisfied that the correct room number is entered, the caregiver selects the enter key 70. If the caregiver wishes to abort the room number change altogether, the caregiver selects the cancel key 72. After the enter key 70 is selected, GUI 60 returns to the home screen, as shown in FIG. 7, but having the new room number displayed on screen 62. Thereafter, circuitry 22 of bed 20 transmits the new (now the current) room number as the location ID rather than the old room number.

Figure 8:
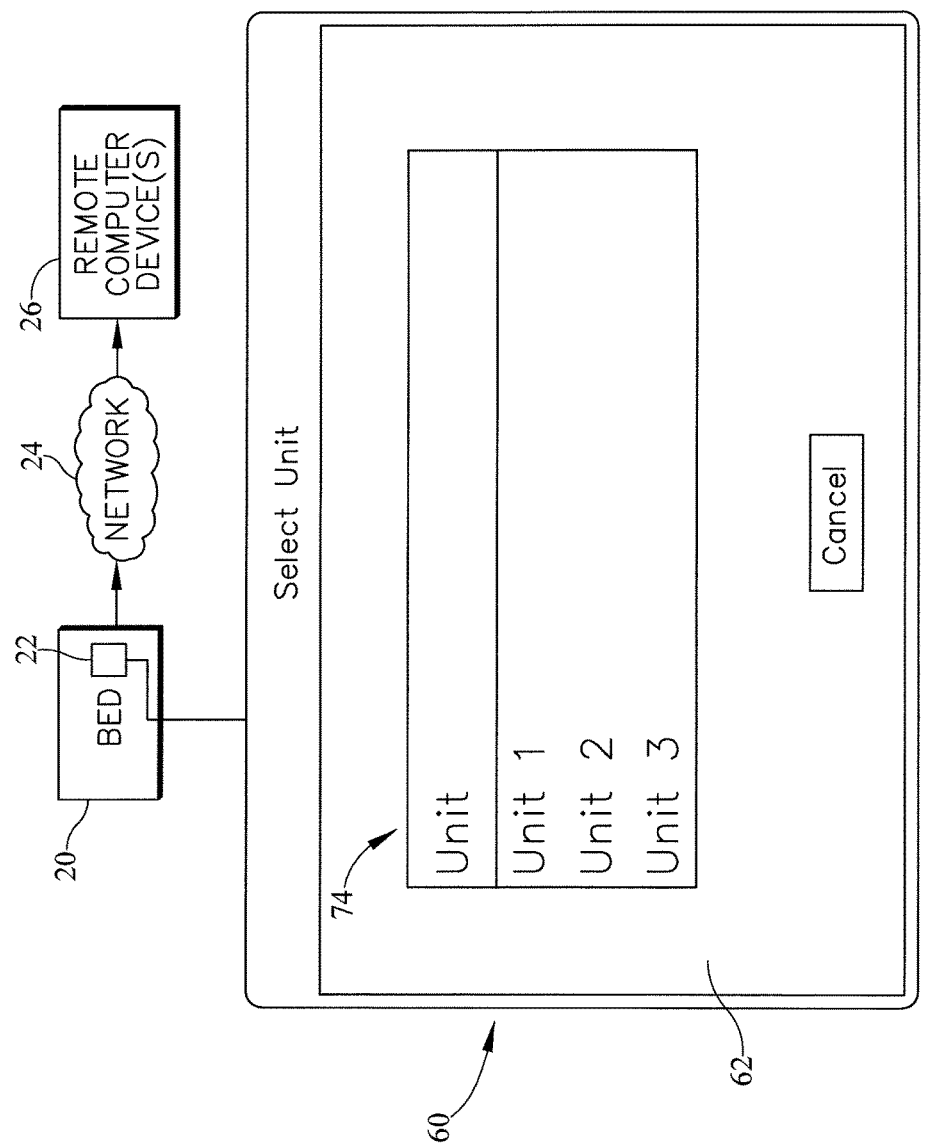
FIG. 8 is a diagrammatic view of an alternative embodiment showing the GUI displaying a menu of unit ID's that appear on a drop down menu in response to selection of the change button.

Referring now to FIG. 8, in some embodiments, after selection of the change button 64 of FIG. 5, an alternative screen appears on GUI 60 and on this alternative screen is displayed a menu of unit ID's, such as a drop down menu. The user then selects the desired unit by touching the display screen 62 over the text corresponding to the desired unit. In the illustrative example, the text "Unit 1," "Unit 2," and "Unit 3" appears in menu 74, but other unit names such as ICU, NICU, Med/Surg, Neurology, Pediatrics, and so forth, just to name a few, are within the scope of this disclosure. The text appearing in menu 74 is dictated by the programming of the software stored in circuitry 22 of bed 20. A cancel button 75 appears beneath menu 74 in the FIG. 8 example and is selected by a caregiver to abort changing the location ID of bed 20.

Figure 9:
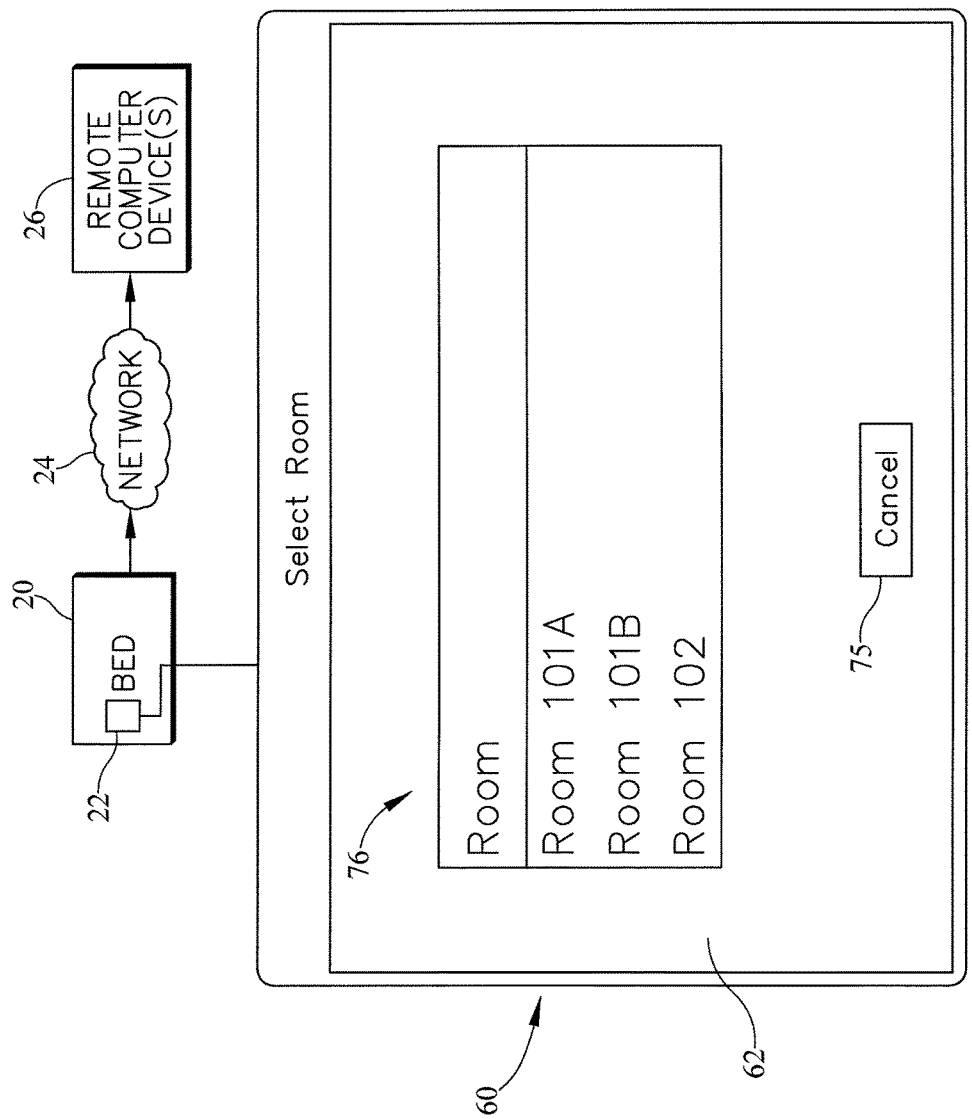
FIG. 9 is a diagrammatic view, similar to FIG. 8, showing the GUI displaying a menu of room ID's that appear on a drop down menu in response to selection of the unit ID on the GUI screen of FIG. 8.

In response to selection of the desired unit from unit menu 74 of FIG. 8, a room menu 76 appears on screen 62 of GUI 60 as shown in FIG. 9. Room menu 76 lists the rooms that are within the unit selected from menu 74. In the illustrative example, the text "Room 101A," "Room 101B," and "Room 102" appears in menu 76, but other room identifiers are within the scope of this disclosure. The text appearing in menu 76 is dictated by the programming of the software stored in circuitry 22 of bed 20. Cancel button 75 also appears beneath menu 76 in the FIG. 9 example and is selected by a caregiver to abort changing the location ID of bed 20. By providing one or both of menus 74, 76, rather than keypad 66, caregivers are only able to select location designators that are in the pre-approved format. In other words, it might be possible for caregivers to use keypad 66 to enter an erroneous room designation or to enter a room number that doesn't exist. By having menus 74, 76 with options from which caregivers select, the possibility for unit/room ID errors is minimized.

Figure 10:
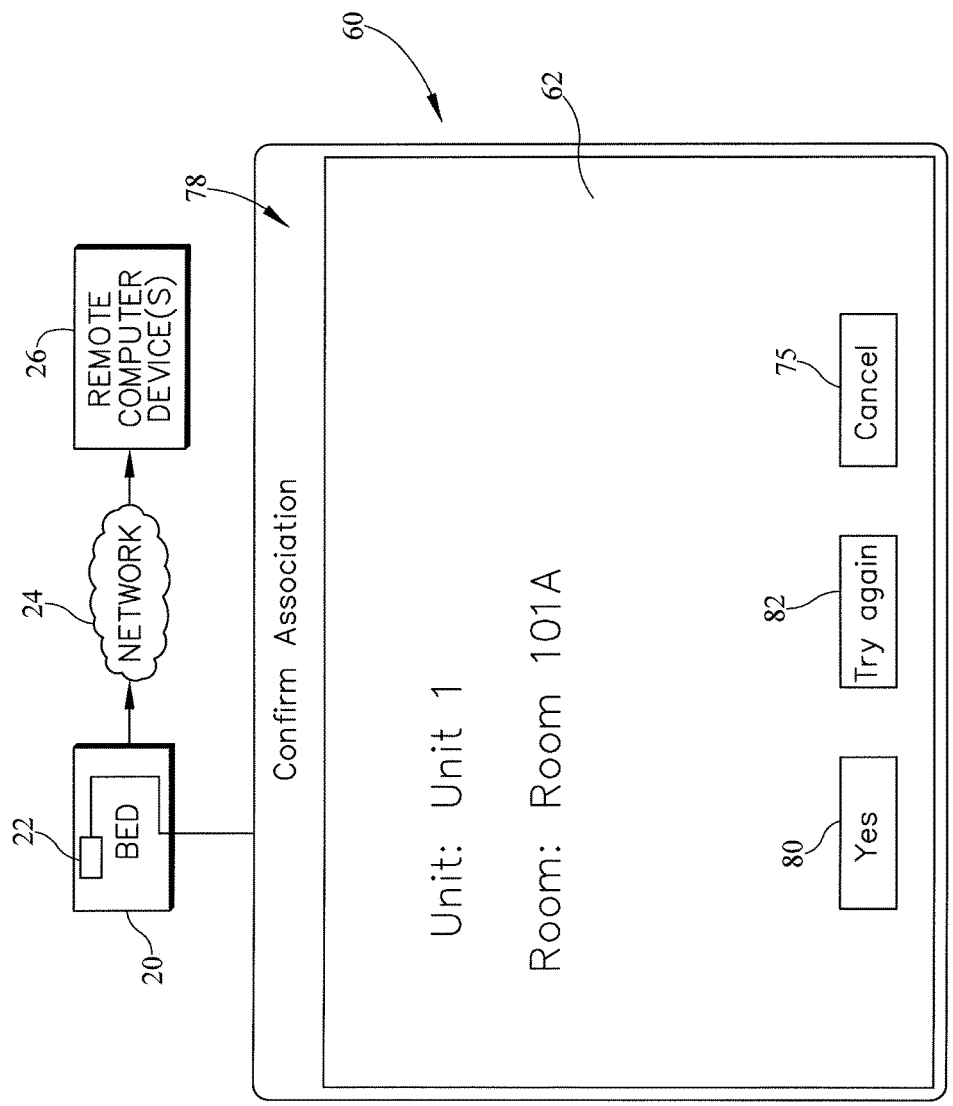
FIG. 10 is a diagrammatic view showing a Confirm Association screen that appears on the GUI after the unit ID and room ID have been selected, a yes button that is selected by the caregiver to confirm the association of the bed to the selected unit and the selected room, the bed transmitting the selected unit ID and the selected room ID, along with a bed ID, to the one or more remote computer devices via the network.

In response to selection of the desired room from room menu 76 of FIG. 9, a Confirm Association screen 78 appears on the GUI 60 as shown in FIG. 10. In the illustrative example of FIG. 10, there is text indicating that "Unit 1" was selected by the caregiver from menu 74 and "Room 101A" was selected by the caregiver from menu 76. Screen 78 includes a yes button 80 that is selected by the caregiver to confirm the association of the bed 20 to the selected unit and the selected room. The unit and room information, therefore, becomes the location ID for bed 20 in response to button 80 being selected. Bed 20, thereafter, transmits the selected unit ID and the selected room ID (now, the location ID), along with a bed ID, to one or more remote computer devices 26 via the network 24 and the one or more remote computer device(s) makes the bed-to-room association based on those ID's. Screen 78 has a Try again button 82 that the caregiver selects to return to the screen of FIG. 8 having the unit menu 74 to start the process anew. Screen 78 also has the back button 75 that is selected by the caregiver to abort the room change operation and return to the home screen of FIG. 5, for example.

Figure 11:
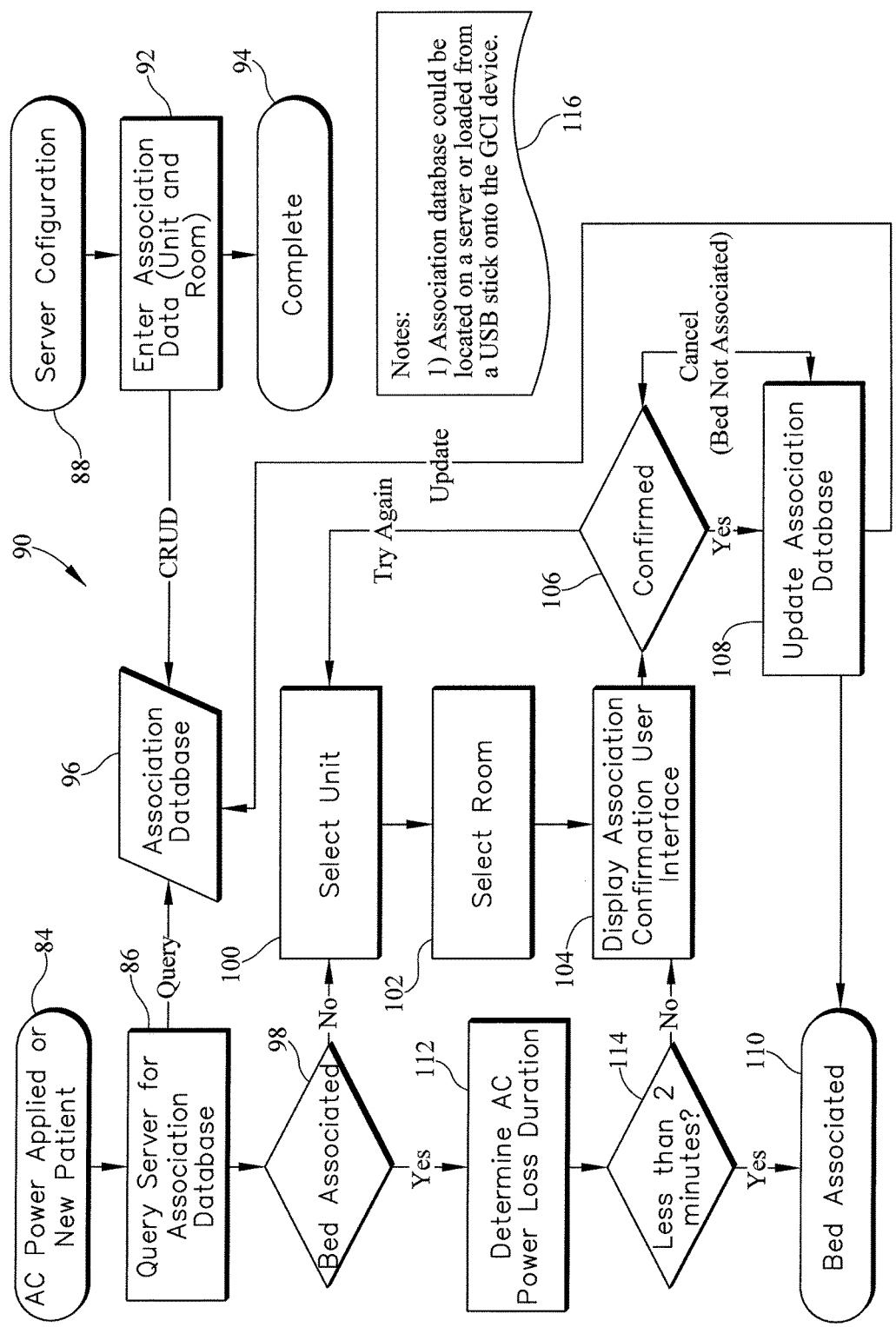
FIG. 11 is a flow chart of an algorithm of the bed that is embodied in software and that is executed to permit selection of the unit ID and the room ID by the caregiver.

Referring now to FIG. 11, a flow chart 90 is provided and is illustrative of software that is executed, in some embodiments, by bed 20 and by a remote server 26 to permit selection of the unit ID and the room ID by the caregiver in response to AC Power being applied or after a new patient arrives at the bed. In the embodiment contemplated by the flow chart of FIG. 11, bed 20 is capable of two way communication with the remote computer device or server 26. Accordingly, as indicated at block 84, after AC power is applied to the bed 20 (e.g., a power cord of the bed gets plugged into an AC outlet after having been unplugged) or after a new patient arrives at the bed 20, bed 20 queries the server for an association database as indicated at block 86. Thus, prior to use of bed 20, a server configuration is performed at the server 26 as indicated at block 88 of flow chart 90. During the server configuration, association data indicative of which rooms are included as part of each unit are entered into a database of server as indicated at block 92 until complete as indicated at block 94, at which point an association database exists for use by bed 20 as indicated at block 96. In some embodiments, prior bed-to-room associations are also populated in the association database of block 96.

After bed 20 queries server 26 for the existence of the association database, bed 20 proceeds to block 98 and determines whether the bed 20 is associated with a location, which in this example means the bed 20 is associated with a unit and a room. If there is no bed-to-location association in the database, then bed 20 proceeds to block 100 and the screen of FIG. 8 is presented to the caregiver on GUI 60 for selection of the appropriate unit occupied by the bed 20. After unit selection, bed 20 proceeds to block 102 and the screen of FIG. 9 is presented to the caregiver on GUI 60 for selection of the appropriate room occupied by the bed 20. After room selection, bed 20 proceeds to block 104 and the Confirm Association screen of FIG. 10 is presented to the caregiver on GUI 60. As indicated at block 106, if the caregiver selects the yes button 80, bed 20 proceeds to update the association database as indicated at block 108 such as by, for example, transmitting the bed ID and the manually entered location ID to the server 26 via network 24. At that point, the bed is associated with the location (room and unit in this example) as indicated at block 110.

If at block 106, the caregiver selects the Try again button 82, bed 20 proceeds back to block 100 as indicated in FIG. 11 and the software algorithm proceeds from there as already discussed above. If at block 106, the caregiver selects the cancel button 75, the bed 20 is not associated with any location and the association database is updated to indicate that there is no location associated with the bed. In some embodiments, further notifications are displayed on screen 62 of GUI to advise the caregiver that the bed is not associated and that the caregiver should try again by selection of button 82.

If at block 98 bed determines that it is associated with a location in the association database, bed 20 proceed to block 112 and determines how long the bed 20 experienced the AC power loss, such as being unplugged. As indicated at block 114, if the power loss was less than two minutes, then bed proceeds to block 110 and the prior bed-to-location association is maintained. If the power loss was more than two minutes, as determined at block 114, then Confirm Association screen 78 of FIG. 10 is presented to the caregiver on GUI 60 so that the caregiver can confirm the bed to location association or change it. As indicated in a notes block 116 of FIG. 11, in some embodiments, a universal serial bus (USB) stick is used in lieu of or in addition to the server 26 to store the association database. Thus, in some embodiments, the association database is loaded periodically into the memory of circuitry 22 of bed 20 using a USB stick or other similar type of portable memory device.

Figure 12:
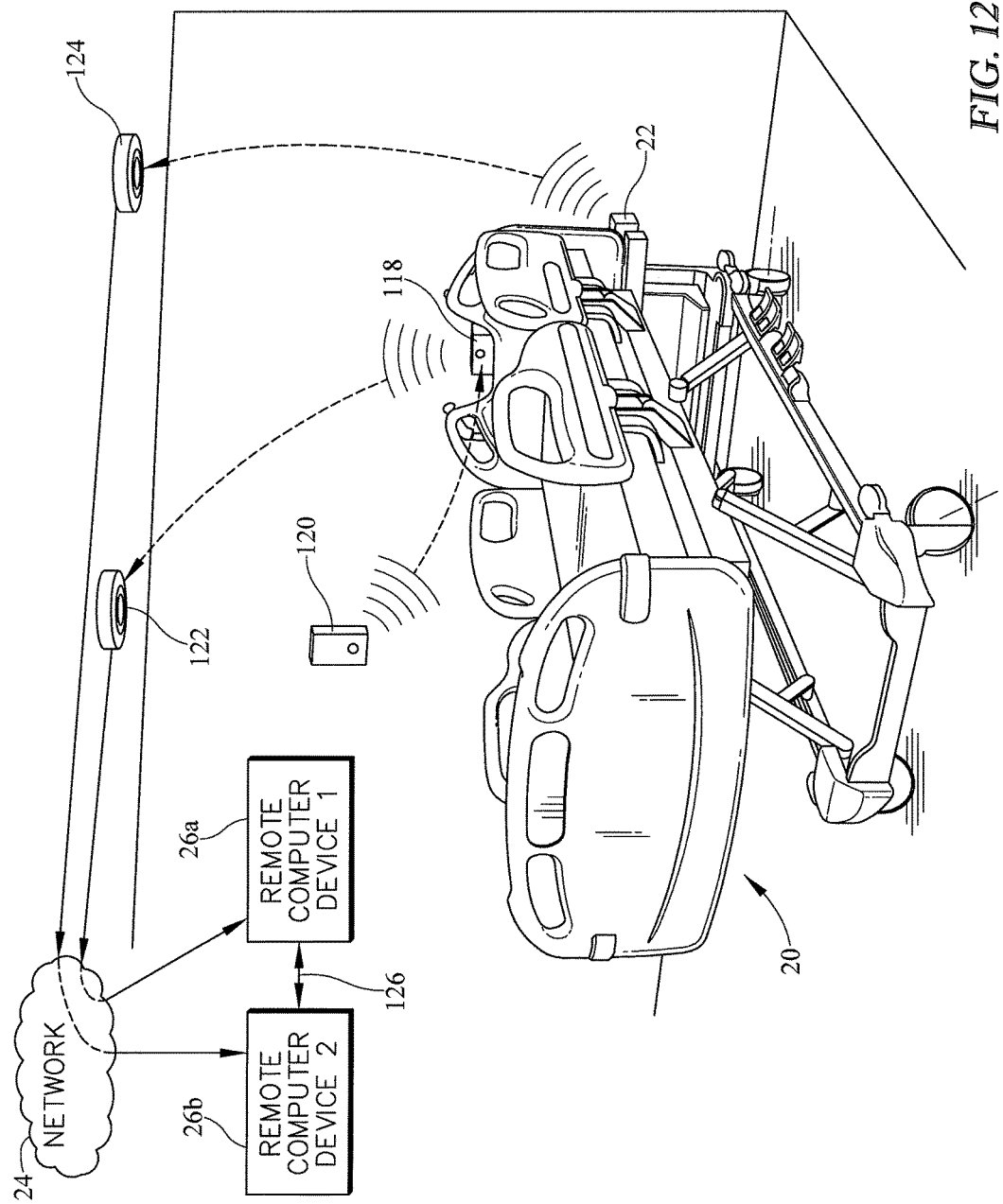
FIG. 12 is a diagrammatic view showing a patient bed having a tag that receives a locator ID from a fixed location unit and that transmits a tag ID and the locator ID to a first transceiver that, in turn, transmits via a network the tag ID and the locator ID to a first remote computer device, the patient bed having circuitry that transmits a bed ID and bed status data to a second transceiver that, in turn, transmits via the network the bed ID and the bed status data to a second remote computer device, and the first and second computer devices being communicatively coupled so as to cooperate to associate the location ID and the bed status data with the bed ID.

Referring now to FIG. 12, bed 20 has separate circuitry that communicates with first and second remote computer devices 26a, 26b via separate and generally parallel communication channels. According to this disclosure, first circuitry of bed 20 is included on a locating tag 118 that is affixed to bed 20 to be transported therewith. A locator or location unit 120 is mounted at a fixed location unit in the room, such as on a room wall, and transmits a locator ID to the tag 118. The tag 118 transmits a tag ID and the locator ID to a first transceiver 122 that, in turn, transmits via network 24 the tag ID and the locator ID to the first remote computer device 26a. Circuitry 22 of bed 20 serves as the second circuitry in this embodiment and transmits a bed ID and bed status data to a second transceiver 124 that, in turn, transmits via the network 24 the bed ID and the bed status data to the second remote computer device 26b. The first and second computer devices 26a, 26b are communicatively coupled, as indicated by the double headed arrow 126, so as to cooperate to associate the location ID and the bed status data with the bed ID. The association can occur in computer device 26a, computer device 26b, or both.

It is contemplated by this disclosure that the first circuitry of tag 118 transmits the first ID and the location ID using a first wireless transmission technology and that the second circuitry, here circuitry 22 of bed 20, transmits the bed ID and the bed status data using a second wireless transmission technology that is different than the first wireless transmission technology. For example, the first wireless transmission technology may comprise one of infrared (IR) technology, radio frequency (RF) technology, and ultrasonic (US) technology and the second wireless transmission technology comprises a different one of IR technology, RF technology, and ultrasonic technology.

Figure 13:
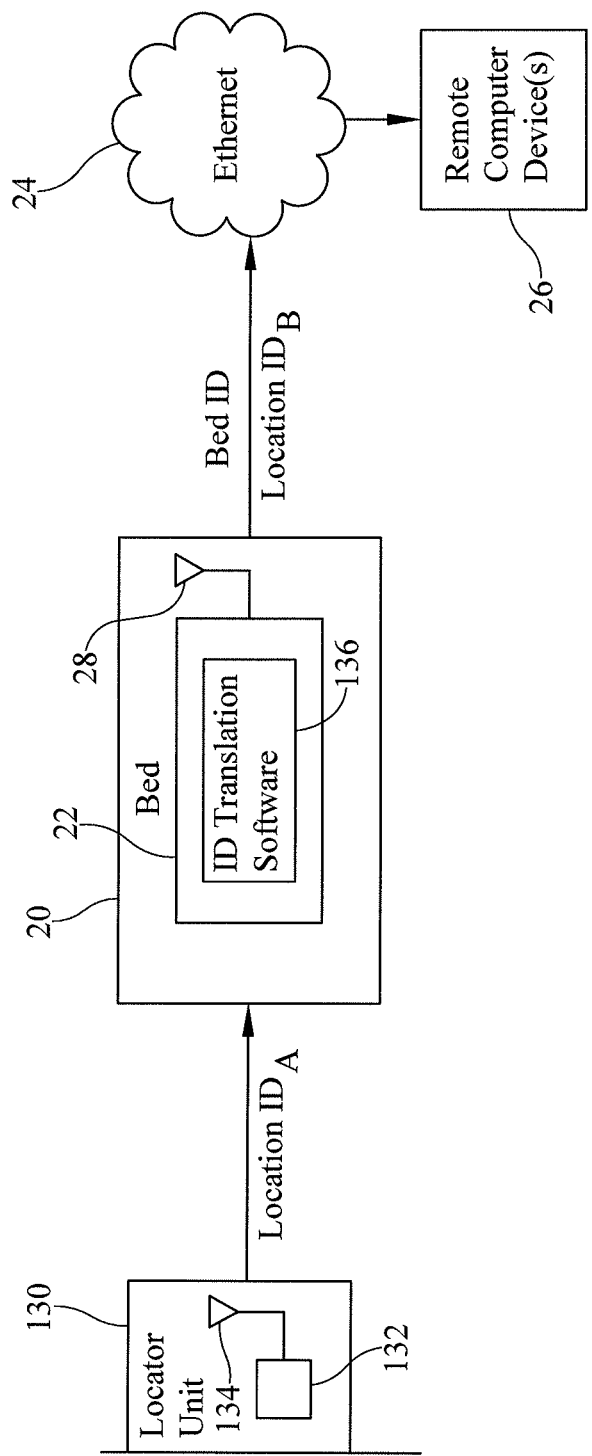
FIG. 13 is a diagrammatic view showing a locator unit transmitting a location $ID_A$, a bed receiving location $ID_A$ and having ID translation software stored in bed circuitry that converts location $ID_A$ to location $ID_B$, the bed transmitting a bed ID and location $ID_B$ to at least one remote computer device via a network, whereby the location $ID_A$ received by the circuitry of the patient bed is not transmitted by the circuitry.

Referring now to FIG. 13, a further embodiment according to this disclosure includes a locator unit 130 that is mounted to a fixed location in a healthcare facility. Unit 130 has circuitry 132 with a transmitter 134 that is commanded by circuitry 132 to transmit a first location ID, which in the illustrative example is designated as location $ID_A$. Circuitry 22 of bed 20 receives location $ID_A$ and has ID translation software 136 that is stored in circuitry 22 and that converts location $ID_A$ to a second location ID (sometimes referred to herein as a modified ID), which in the illustrative example is designated as location $ID_B$. For example, in some embodiments, the modified ID is or includes a room number of a room in a healthcare facility in which the patient bed is located and the translation software 136 includes a look up table that correlates the location ID with the room number of the modified ID. Thereafter, circuitry 22 of bed 20 commands transmitter 28 to transmit a bed ID and location $ID_B$ (i.e., the modified ID) to at least one remote computer device 26 via network 24, whereby the location $ID_A$ received by the circuitry of the patient bed 20 is not transmitted by the circuitry 22 of bed 20. For example, if the location $ID_A$ is 16 bits or 32 bits, or more, in length, the location $ID_B$ may be shorter in length and yet still suitable for the purpose of indicating the room location, such as being 8 bits, thereby conserving transmission power and increasing bandwidth of network 24 by reducing the number of bits that are transmitted by bed 20 over the network 24.

According to this disclosure, the modified ID created by bed translation software 136 may also be in a more desirable format for receipt by other computer devices 26. For example, if location $ID_A$ is a MAC address of locator unit 130, administrators of a healthcare facility may prefer to receive from bed 20 ASCII code of the room number for use in various other software programs on computer devices 26. Translation software 136, therefore, permits modified ID to be converted into the desired format. Computer devices(s) 26, therefore, operate to associate the bed ID and modified ID in an association database and make no use of location $ID_A$.

Figure 14:
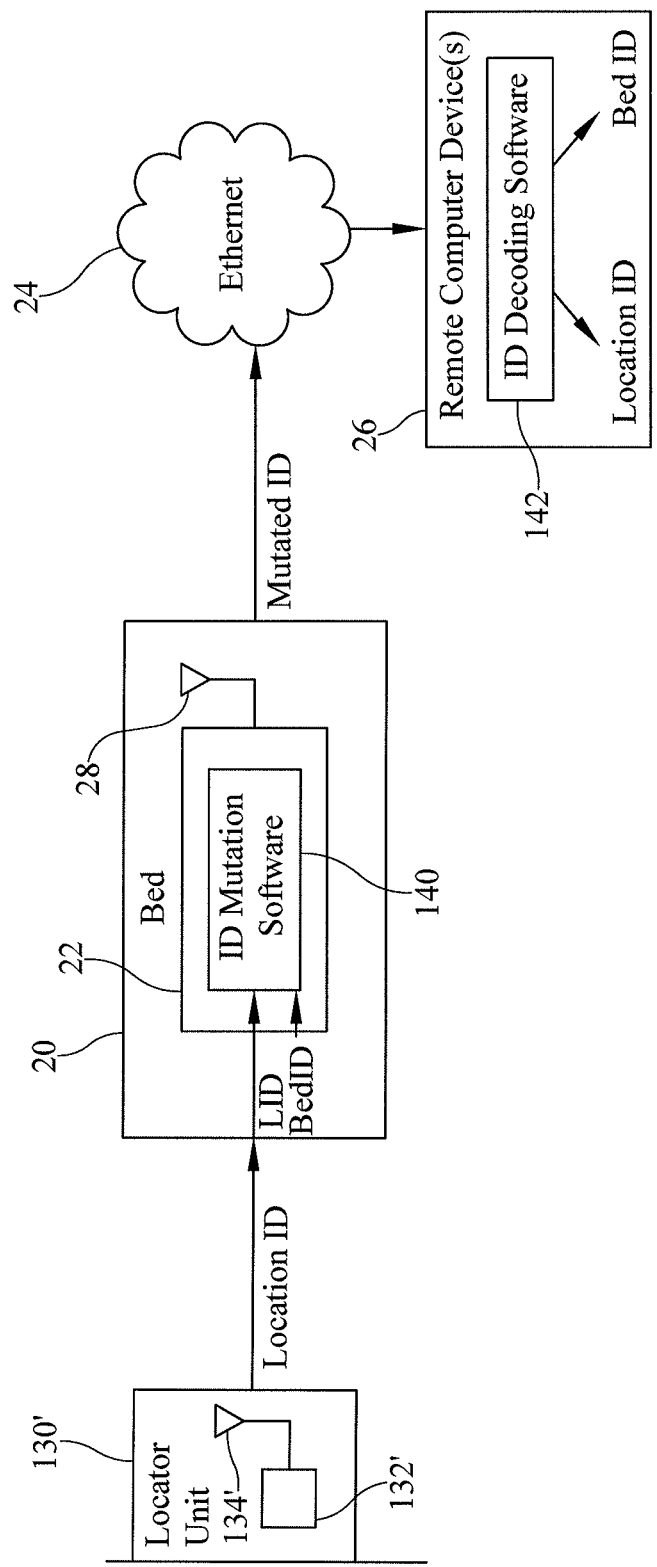
FIG. 14 is a diagrammatic view showing a locator unit transmitting a location ID, a bed having circuitry receiving the location ID and having ID mutation software that is stored in the circuitry and that mutates the location ID and a bed ID into a mutated ID that is a single unique ID that is transmitted by the circuitry of the bed to at least one remote computer device via a network, the remote computer device having ID decoding software that determines the location ID and bed ID that corresponds to the mutated ID.

Referring now to FIG. 14, another embodiment according to this disclosure includes a locator unit 130' that is mounted to a fixed location in a healthcare facility. Unit 130' has circuitry 132' with a transmitter 134' that is commanded by circuitry 132' to transmit a location ID. Circuitry 22 of bed 20 receives the location ID and has ID mutation software 140 that is stored in circuitry 22 and that mutates the location ID and the bed ID into to a single, unique mutated ID. Thereafter, circuitry 22 of bed 20 commands transmitter 28 to transmit the mutated ID to at least one remote computer device 26 via network 24, whereby the mutated ID transmitted from the patient bed 20 is neither the location ID nor the bed ID.

The mutation software 140, in some embodiments, uses a hash function, such as a cryptographic hash function, to mutate the location ID and the bed ID into the single, unique mutated ID. The one or more remote computer devices 26 then use ID decoding software 142 to correlate the mutated ID with the location ID and the bed ID. However, it should be appreciated that neither the location ID nor the bed ID were ever transmitted by the bed 20 to any device on the network 24.

To illustrate the method employed by software 140, consider the scenario in which location ID is in the form ROOM_ID_0001 and the bed ID is in the form BED_ID_0001. The software may add the location ID and the room ID and perform the hashing function by using software programming code such as SHA1 (ROOM_ID_0001+BED_ID_0001) and the resulting mutated ID, in hexadecimal format, is the following: 57e4f41a507079311acbb588d14cae4d564c7d43. While this example used the known SHA-1 hashing function, other known hashing functions may be employed in software 140, including the following: GOST, HAVAL, MD2, MD4, MD5, PANAMA, RadioGatun, RIPEMD, SHA-0, SHA-3, Tiger (2), and WHIRLPOOL.

Once the modified ID is created by the adding and hashing operation just described, the modified ID is transmitted off of the bed for receipt by one or more remote computer devices 26. The software 142 of each remote computer device 26 then uses a lookup table, in some embodiments, to correlate the received modified ID with the bed ID and room ID that created it. The lookup table includes the modified ID's and the associated bed ID and room ID for each possible combination of beds and rooms in a particular healthcare facility. An simple example of a lookup table for two beds that may be located in two different rooms is given as follows (and assumes a hashing function applied to the added room ID and bed ID as described above):

| Bed ID | Room ID | Modified (e.g., added and hashed) ID |
|---|---|---|
| BED_ID_0001 | ROOM_ID_0001 | ffa6160a5ba73befd3f0cfdd5554613fad2094ed |
| BED_ID_0002 | ROOM_ID_0001 | 6818ae262ae95541b03f5367829c1507e32ac595 |
| BED_ID_0001 | ROOM_ID_0002 | bf2019c988268cd007ef7dcb0a280d1e75c8dd45 |
| BED_ID_0002 | ROOM_ID_0002 | c1bf987848b483a8c6af9c4cf716466575db3dc7 |

Thus, if a bed with BED_ID_0001 as its bed ID is physically located in a room with ROOM_ID_0002 as its room ID, then bed 20 transmits via network 24 the modified ID bf2019c988268cd007ef7dcb0a280d1e75c8dd45 to the remote computer device 26 having software 142 and the software correlates the modified ID back to the room ID and bed ID that created it. However, neither the bed ID nor the room ID is transmitted by bed 20.

In an alternative embodiment, software 142 uses a list of all known bed ID's and a list of all known room ID's and the server computes the modified ID's (e.g., by adding and hashing) sequentially and compares each one to the received modified ID until a match is found, at which the point the bed ID and room ID that caused the match are known. This approach eliminates the need to store a large table of known combinations, but does potentially require a fair amount of computational power to perform the mutating operation sequentially.

In another contemplated embodiment, the bed only transmits a received or entered (e.g., via GUI 60) location ID along with other data such as bed status data. Thus, the bed ID is not transmitted off of the bed while the bed is in use. In such embodiments, the location ID is considered to be the bed ID while the bed is in the room associated with the room ID. In such embodiments, the bed may store in a database of circuitry 22 the room ID along with the start and end times at which the bed considered that particular room ID to be the bed ID. The start and end times include, for example, minutes, hours, day, month, and year. For many systems and software applications used in a healthcare environment, the end users are not interested in knowing the bed ID anyway. They are more interested in knowing which device status data goes with which patient. This can be accomplished in many instances by associating location ID, patient ID, and device status ID. In this regard, device status ID may include the patient's physiological data as measured by a particular device. Manufacturers are more interested in knowing bed ID for service and maintenance purposes. Thus, at a later time, a service technician downloads the bed ID along with the rooms in which the bed was located in the past. Appropriate data analysis is made by the service technician after the download.

Referring now to FIG. 15, bed 20 optionally includes an indicator module 150 that mounts to a portion of bed 20 such as upper frame 152. In other embodiments, module 150 is mounted to some other portion of bed 20 such as base frame 154, one of endboards 156, or one of siderails 158. Indicator module 150 has a first light emitting diode (LED) 160 that is illuminated to indicate Wi-Fi signal strength between circuitry 22 (not shown in FIG. 15) of bed 20 (and/or circuitry 166 of module 150) and a wireless access point 124. In one embodiment, LED 160 is a three color LED (e.g., red, yellow, green) that is illuminated a particular color to indicate the relative signal strength. In some embodiments, wireless access point 124 operates to determine the signal strength of the communication link between it and circuitry 22 of bed 20 (or circuitry 166 of module 150) and, in other embodiments, circuitry 22 of bed 20 (or circuitry 166 of module 150) operates to determine the signal strength of the communication link between it and wireless access point 124.

Module 150 has a second LED 162 that is illuminated to indicate that a successful communication link has been established between circuitry 22 (not shown in FIG. 15) of bed 20 and one or more remote computer devices, such as devices 26a, 26b of FIG. 12, one or both of which may be considered a remote nurse call computer device. Module 150 has a third LED 164 that is illuminated to indicate that a successful bed-to-room association has been made at a remote computer device such as one or both of remote computer devices 26a or 26b of FIG. 12. In some embodiments, device 26a is a server of a real time location system (RTLS) and device 26b is a server of a nurse call system. Having third LED 164 included on module 150 is an improvement over known prior art beds which did not have any indicator relating to whether a successful bed-to-room association had been made. Alternatively or additionally, indicator 164 provides an indication of a successful bed-to-patient association, a successful room-to-patient association, and/or a successful bed-to-room-to patient association.

In one embodiment, circuitry 166 of module 150 includes a Model No. WB45NBT device available from Laird Technologies of Earth City, Mo. Details of the Model No. WB45NBT device can be found in *Laird Reference Manual, Laird WB45NBT*, Version 1.0, dated Aug. 20, 2013, which is hereby expressly incorporated by reference herein. Circuitry 166 of module 150 connects to circuitry 22 of bed 20 via a universal serial bus (USB) cable in some embodiments. In such embodiments, therefore, circuitry 22 and circuitry 166 each include a USB port. In other embodiments, circuitry 166 of module 22 and circuitry 22 of bed 20 communicate wirelessly. Circuitry 166 controls the illumination of LED's 160, 162, 164 via shift registers in some embodiments. Circuitry 166 includes a Wi-Fi antenna and/or a Bluetooth (BT) antenna in some embodiments. For example, a suitable antenna for either or both of these purposes is the Laird Model No. 95310 antenna. In some embodiments contemplated by this disclosure, circuitry 22 of bed 20 does not have wireless communication capability but instead relies on the wireless communication capability of circuitry 166 of module 150 to communicate bed data wirelessly to and from network 24 via wireless access point 124.

In some embodiments of the systems illustrated in FIGS. 12 and 15, the RTLS components are available from CenTrak, Inc. of Newtown, Pa. For example, in some embodiments, tag 118 is a CenTrak model no. IT-710 tag; RTLS location beacon or location unit 120 is a CenTrak model no. ITK-313 Monitor or a CenTrak model no. IT-323 Virtual Wall; and RTLS aggregator or transceiver 122 is a CenTrak model no. IT-103 Star. It should be appreciated, however, that RTLS components from other suppliers may be used in lieu of, or in addition to, the CenTrak components.

In alternative embodiments, RF triangulation is used to locate bed 20 in a healthcare facility. In such embodiments, tag 118, location unit 120 and transceiver 122 are omitted. Instead, multiple (typically three or more) Wi-Fi transceivers, such as wireless access points 124, receive wireless transmissions from bed 20 and then a remote computer device, such as one of servers 26a, 26b, analyzes signal strength and or time-of-flight information from the multiple wireless access points 124 to determine the location of bed 20. Once the location has been determined, bed 20 is notified wirelessly and indicator 164 of module 150 is illuminated.

Referring now to FIG. 16, a block diagram of a wireless bed-to-room association system similar to that of FIG. 12 but including a Wi-Fi module 150' is provided. In FIG. 16, Wi-Fi module 150' is similar to module 150 of FIG. 15. A wired connection 168, such as a USB cable, interconnects circuitry 22 and module 150'. It is within the scope of this disclosure for module 150' to be considered part of circuitry 22 but these are illustrated as separate blocks in FIG. 16 for ease of discussion. Thus, module 150' and its associated circuitry, like circuitry 166 of module 150, are integrated into the overall electrical system of bed 20 in some embodiments.

As shown diagrammatically in FIG. 16, a monitor ID 170 is transmitted from location unit 120, referred to in FIG. 16 as an RTLS location beacon, to an RTLS tag 118 mounted to bed 20. Monitor ID 170 is transmitted as a low frequency or infrared (IR) signal from beacon 120 as indicated by block 172. Thus, it is contemplated by this disclosure that only the tags 118 of beds in the same room or in close proximity to beacon 120 are able to receive monitor ID 170. After tag 118 has received monitor ID 170, tag 118 transmits a radio frequency (RF) signal, as indicated at block 174 in FIG. 16, that includes the monitor ID plus tag ID 176 for receipt by transceiver 122, which in FIG. 16 is referred to as an RTLS aggregator. The term "aggregator" is use because transceiver 122 will potentially receive RF signals from a multitude of beds 20 that are within its reception range. As indicated by diagrammatic arrow 178 in FIG. 16, the signals received by aggregator 122 are forwarded to remote computer device 26a which is referred to in FIG. 16 as an RTLS server. The monitor ID and Tag ID are paired to form a location association by RTLS server 26a as indicated by the text within arrow 178.

Still referring to FIG. 16, remote computer device 26b is coupled to RTLS server 26a via communication link 126. Device 26b is referred to as a bed data server in FIG. 16 but may just as well be referred to as a nurse call server. Bed data server 26b includes a database table 180 in which is stored, among other things, the location association information based on the monitor ID and tag ID pairing received from RTLS server 26a. Thus, one or both of servers 26a, 26b include RTLS Application Programming Interface (API) Integration software as indicated by the text within double headed arrow 126 of FIG. 16.

Wi-Fi module 150' of bed 20 sends a Wi-Fi signal, as indicated at block 182, that includes bed ID data 184. It should be appreciated that bed 20 also transmits bed status data along with bed ID 184. Bed status data includes bed frame data such as siderail position data, caster brake position data, lift system data, head of bed angle data, weigh scale system data, bed exit system data, motor lockout data, and the like; support surface data such as therapy mode data, maximum inflate data, turn assist data, and the like; and other data such as battery charge data, AC present/not present data, nurse call button data, and the like. For a more exhaustive list of bed status data that may be associated with bed 20, see U.S. Patent Application Publication No. 2013/0135160 which is hereby incorporated by reference herein in its entirety to the extent not inconsistent with this disclosure which shall control as to any inconsistencies.

The bed status data and bed ID are received by server 26b and are processed by bed data aggregator software 186 as indicated diagrammatically in FIG. 16. Details of bed data aggregator software 186 can be found in U.S. Patent Application Publication No. 2012/0316892 which is hereby incorporated herein by reference herein in its entirety to the extent not inconsistent with this disclosure which shall control as to any inconsistencies. While FIG. 16 shows a single bed 20 communicating with server 26b, it should be appreciated that a multitude of beds 20 communicate with server 26b. Thus, the bed data aggregator software processes the bed status data and bed ID data from all of such beds.

Server 26a and/or server 26b stores information or has access to information that correlates the bed ID with the tag ID. Such information is entered into server 26a, 26b in connection with assigning tags 118 to the various beds 20 in some embodiments. Thus, the information correlating tag ID and bed ID is included in database table 180 in some embodiments. Furthermore, it will be appreciated that the monitor ID from each location beacon 120 corresponds to a particular location (e.g., room) of a healthcare facility. Accordingly, the bed status data that is transmitted with bed ID 184 is able to be associated with a particular location at which bed 20 is located due to the correlation of monitor ID with the tag ID of bed 20 and the correlation of the tag ID with the bed ID. These various correlated relationships are maintained in database 180 in some embodiments. The bed status data is also included in database 180 in some embodiments.

According to this disclosure, after the monitor ID, tag ID, and bed ID are correlated by server 26b, a prospective or preliminary bed-to-room association is considered to exit. However, before the bed-to-room association is considered to be finalized, server 26b determines whether a power plug 188 of power cord 190 of bed 20 is coupled into a receptacle 192 to receive AC power therefrom. The act of connecting plug 188 into receptacle 192 permits the inference to be drawn that bed 20 is likely to remain at the particular location for an extended period of time rather than simply being in transit or only temporarily at the location for a short period of time. If server 26b determines that the bed status data indicates that bed 20 is receiving AC power from receptacle 192, then location information 194 is transmitted to Wi-Fi module 150' to indicate a successful or finalized bed-to-room association has been made.

Figure 17:
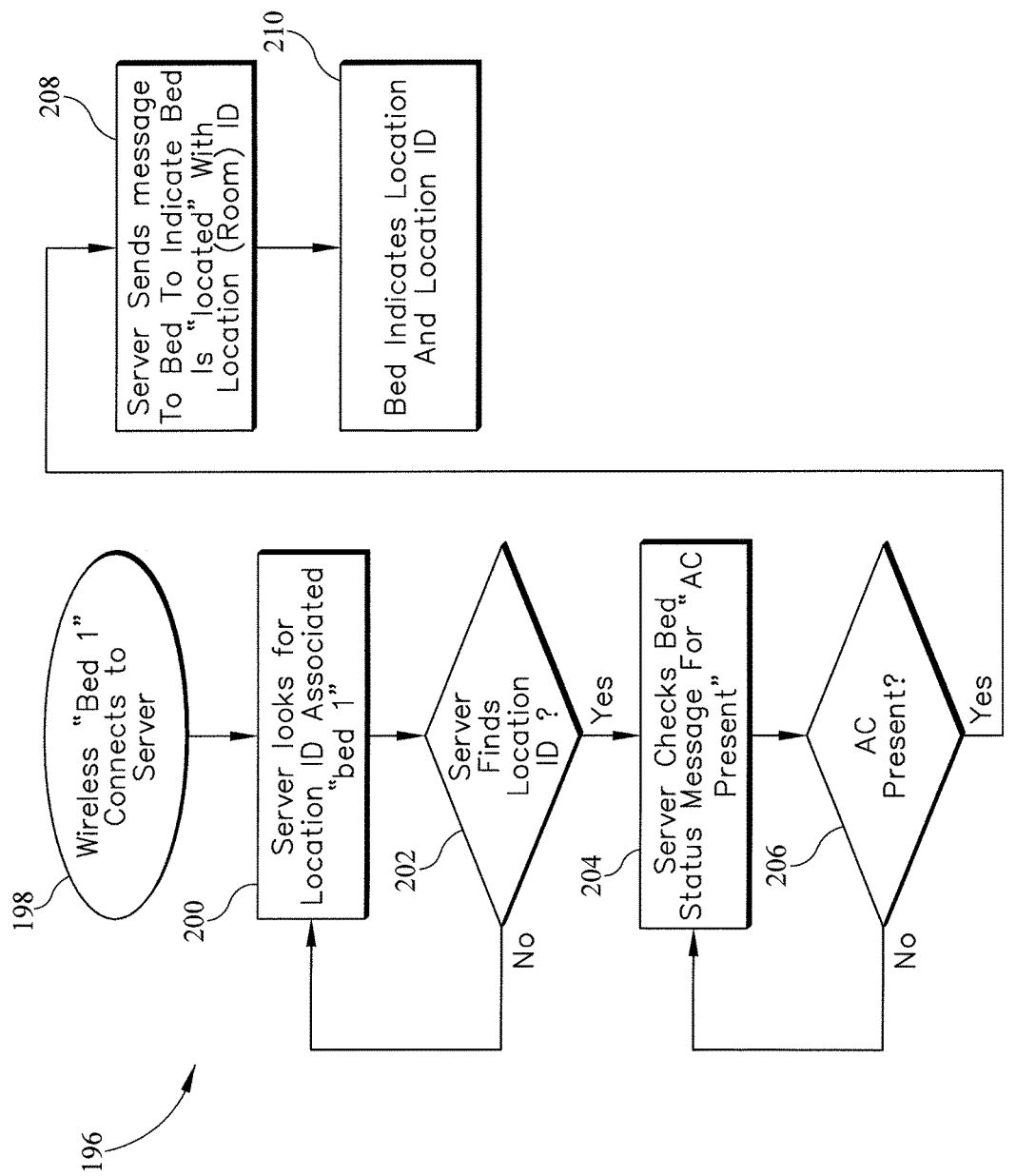
FIG. 17 is a flow chart showing an algorithm of a portion of the software executed by the remote server of the system of FIG. 16 in which the remote server first confirms that the hospital bed is plugged into an AC outlet prior to sending the location information to the circuitry of the hospital bed.

Referring now to FIG. 17, a flow chart of an algorithm 196 of a portion of the software executed by server 26b of the system of FIG. 16 is shown. Block 198 of the algorithm states "Wireless 'Bed 1" Connects to Server," which means that server 26b receives packets of data (e.g., bed ID 184 and bed status data) that have been communicated wirelessly from module 150' of bed 20. The packets are communicated to server 26b via transceiver 122 and network 24 as described previously in this disclosure. Thus, it should be appreciated that the so-called wireless packets are eventually communicated over various wired communication links (including fiber optic communication links in some embodiments) of the network infrastructure of a healthcare facility to reach server 26b.

As indicated at block 200, server 26b looks for location ID associated with bed 20. The location ID referenced in block 200 includes, for example, monitor ID 170 or a room number or other location name or number that correlates to monitor ID 170. If at block 202, server 26b does not find a location ID that is associated with bed 20, then the algorithm 196 loops back to block 200. It will be appreciated that, if algorithm remains in the block 200, 202 loop for a predetermined period of time or for a predetermined number of iterations, the software will exit from the loop and send an alarm message or return to some other portion of algorithm 196 or another algorithm.

If server 26b finds the location ID for bed 20 at block 202, server 26b proceeds to block 204 to check the bed status message for "AC present" data which means that the plug 188 of power cord 190 of bed 20 is plugged into receptacle 192. As indicated at block 206, if server 26b does not find AC present, then the algorithm 196 loops back to block 204. It will be appreciated that, if algorithm remains in the block 204, 206 loop for a predetermined period of time or for a predetermined number of iterations, the software will exit from the loop and send an alarm message or return to some other portion of algorithm 196 or another algorithm.

If server 26b finds AC present at block 206, server 26b proceeds to block 208 and sends a message to bed 20, including the Location or Room ID 194, to indicate that bed 20 has been successfully located. Thereafter, bed 20 indicates a successful bed-to-room location by displaying the location ID (e.g., room name or number) on a graphical display screen of bed 20 or by otherwise indicating a successful bed-to-room location such as by illuminating indicator 164 of module 150 as discussed above in connection with FIG. 15.

Figure 18:
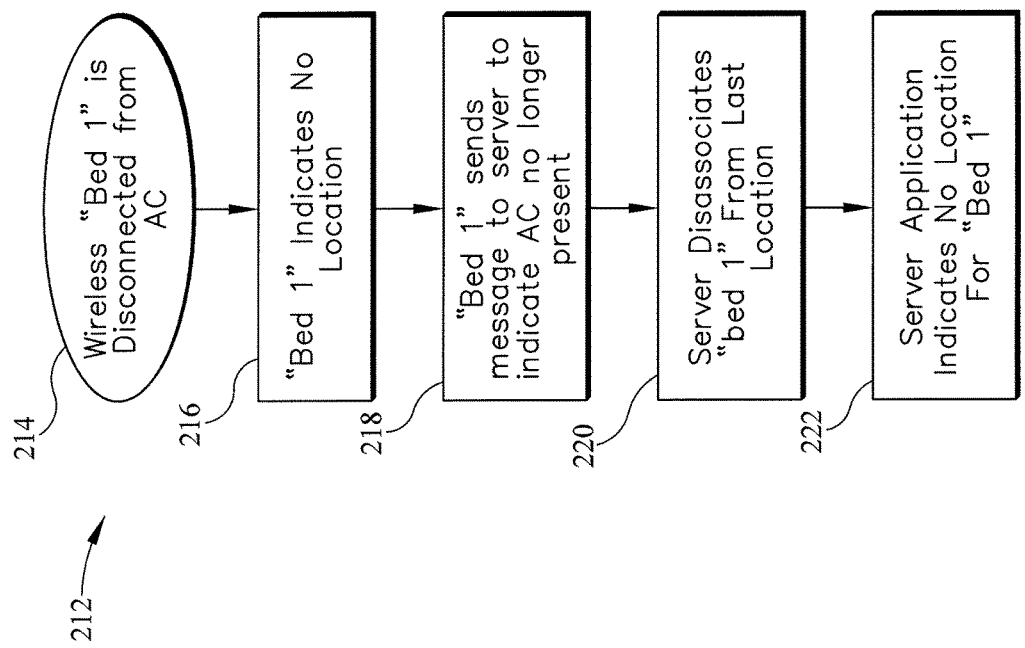
FIG. 18 is a flow chart showing a disassociation algorithm implemented by the hospital bed and remote server of FIG. 16 in response to the hospital bed being disconnected from an AC power outlet.

Referring now to FIG. 18 is a flow chart showing a disassociation algorithm 212 implemented by bed 20 and remote server 26b of FIG. 16 in response to the bed 20 being disconnected from the AC power outlet or receptacle 192. As indicated at block 214, algorithm 212 begins in response to plug 188 of bed 20 being disconnected from receptacle 192. After that occurs, bed 20 indicates no location such as, for example, by ceasing to display the room name or number on a graphical display screen of bed 20 or by turning off indicator 164 of module 150. Algorithm 212 then proceeds to block 218 at which bed 20 sends a message to server 26b indicating that AC is no longer present due to the unplugging of plug 188 from receptacle 192. After server 26b receives that message from bed 20, server 26b disassociates bed 20 from the last location as indicated at block 220 and proceeds to indicate no location for bed 20 as indicated at block 222. In some embodiments, this involves removing data from table 180. For example, the bed ID and bed status data may be maintained in table 180 but the monitor ID, tag ID and/or location ID (or other location information such as room name or room number) is removed and, if desired, replace with the string "no location." Alternatively, the monitor ID, tag ID and/or location ID (or other location information) is maintained in the table 180 and the bed ID and/or bed status data is removed from table 180.

Referring now to FIG. 19 a patient-to-bed association system includes a wireless heart rate monitor 224 that includes circuitry 226 configured to send data, including the patient's medical record number (MRN), wirelessly to circuitry of bed 20. In FIG. 19, the circuitry of bed is omitted but suffice it to say that the circuitry of bed 20 is discussed elsewhere herein in connection with each of the other embodiments in which bed 20 has wireless communication capability. As indicated by diagrammatic arrow 228 in FIG. 19, bed 20 is configured to transmit the patient's MRN and bed ID data wirelessly for used by one or more remote computer devices (e.g., servers 26a, 26b) to associate the patient to the bed 20. In some embodiments, heart rate monitor 224 also sends heart rate data to bed 20 for display on a graphical display screen of bed 20 or for wireless transmission to remote computer devices such as servers 26a, 26b and/or to one or more computer devices of an EMR system.

Circuitry 226 of heart rate monitor 224 is programmable with the patient's MRN. For example, such programming may occur upon admittance of the patient to a healthcare facility. In some embodiments, circuitry 226 includes a Bluetooth module for communication of wireless data via the Bluetooth protocol. A suitable heart rate monitor is the Wahoo Blue TICKR monitor available from Wahoo Fitness of Atlanta, Ga. In the illustrative example of FIG. 19, monitor 224 is coupled to the patient's arm via an arm band 230. In other embodiments, monitor 224 is coupled to the patient by a chest band that is similar to arm band 230, but larger to fit around the circumference of the patient's chest. In some embodiments, arm band 224 is adjustable and so is expandable so as to be usable as a chest band.

Alternatively or additionally, monitor ID data of heart rate monitor 224 is mapped or correlated with the patient's ID data in a database, such as in a database of RTLS server 26a or in database table 180 of server 26b or some other server such an ADT server. The monitor ID data is transmitted wirelessly from monitor 224 to bed 20 and then sent wireless from the bed 20 along with the bed ID data as indicated diagrammatically by arrow 228 in FIG. 19. Regardless of whether the patient's MRN is used or monitor ID data is used, a patient-to-bed association and therefore, a patient-to-bed-to-room association is made within database table 180 of server 26b in some embodiments. The capability to pair or otherwise association a patient with medical equipment or than bed 20 using heart rate monitor 224 in a similar manner is also contemplated by this disclosure. This is possible as long as the other medical equipment has the same or similar wireless communication capability as bed 20.

Referring now to FIG. 20, another bed data system is shown diagrammatically in which bed 20 is equipped with a first Bluetooth (BT) module 232 and optionally, in some embodiments, a second BT module 234. Modules 232, 234 communicate with a wall BT module 236 for transmission of bed data, including bed status data and bed ID data, after a BT pairing operation is conducted based on transmission of bed BT module ID data via a transponder 238 carried by a plug of a power cord 240 of bed 20 as indicated by diagrammatic block 242. It is contemplated by this disclosure that modules 232, 234, 236 are Class 2 Bluetooth devices that have a theoretical communication range of up to 33 feet (10 meters) but, in practice, have a communication range on the order of 15-20 feet. This is not to say that in other embodiments, Class 1 Bluetooth devices having a theortetical range of 329 feet (100 meters) or Class 3 Bluetooth devices having a theoretical range of 3.3 feet (1 meter) could not be used in lieu of modules 232, 234, 236. Furthermore, modules using other types of communication technology (e.g., ZigBee, Wi-Fi) are also within the scope of this disclosure for use as alternatives to modules 232, 234, 236.

By using modules 232, 234, 236, the traditional bed status or nurse call cable (e.g., a 37-pin connector cable) between bed 20 and a nurse call module 244 is eliminated. Thus, the power cord 240 is the only cord that connects to, and disconnects from, an associated receptacle. The bed data is communicated wirelessly from one or both of modules 232, 234 to module 236. In the illustrative example of FIG. 20, it is assumed that a nurse call system 246 having one or more nurse call modules 244 in each room is already installed in a healthcare facility. The nurse call modules 244 each are communicatively coupled to a nurse call server 246 as illustrated diagrammatically in FIG. 20 with double headed arrow 247. Thus, to convert the wireless data received by module 236 from either or both of modules 232, 234 into wired data that can be fed to the existing nurse call module 244, a communication board or circuit 248 is provided. Communication circuit 248 communicates with module 236 as indicated by double headed arrow 250. A 37-pin connector cable 252 interconnects communication circuit 248 and nurse call module 244 as indicated by diagrammatic block 254. Data received at nurse call module 244 is communicated to nurse call server 246.

In the illustrative embodiment, wall Bluetooth module 236 communicates with modules 232, 234 via radio frequency (RF) signals according to the Bluetooth protocol which operates on an unlicensed 2.4 gigahertz (GHz) band which is also shared with Wi-Fi and other protocols. To be more specific, the Bluetooth protocol implements an adaptive frequency hopping (AFH) methodology to transmit at any of 79 hopping channels that are 1 megahertz (MHz) apart between 2.4 GHz and 2.4835 GHz. Thus, in addition to receiving wireless signals from modules 232, 234 of bed 20, it is foreseeable that wall BT module 236 will be within the reception range of other devices, including other beds 20, and receive the wireless signals transmitted by those other devices. So, in order to pair module 236 with one or both of modules 232, 234, a loop antenna 256 is provided to read signals sent from transponder 23 as indicated diagrammatically at block 258 in FIG. 20. The signals from transponder 23 are encoded with a first module ID of first module 232 and, if present, a second module ID of second module 234.

If module 232 is the only module on bed 20, then in response to power cord 240 being plugged in, loop antenna 256 is powered up by communication circuit 248 and reads the first module ID from transponder 238 to communication circuit 248. Communication circuit then provides the first module ID to wall BT module 236. In some embodiments, the first module ID corresponds to a unique 48 bit Bluetooth device address (aka the MAC address) of module 232. The first 24 bits of this address represent the manufacturer of the Bluetooth circuitry of module 232 and the remaining 24 bits are unique for each Bluetooth device assigned by the manufacturer. However, any unique module ID would suffice. After receiving the first module ID, wall BT module 236 then operates to accept wireless transmissions from only module 232 and to ignore all other wireless transmissions. In this regard, module 236 accepts wireless transmission packets that contain the first module ID. This is sometimes referred to as an Out of Band (OOB) pair between modules 232, 236.

The transmission packets sent between modules 232, 236 include both audio and data packets in some embodiments. For example, Bluetooth technology is rated for 3 Mega bits per second (Mbps) transmission speed, but in practice the speed is about 2.1 Mbps, which is fast enough to permit audio and data packets to be sent. The delay in the audio signal using Bluetooth technology is about 50 to about 80 milliseconds (ms) which is less than the 100 ms delay required to synchronize television video and audio. Thus, modules 232, 236 of the system in FIG. 20 are an improvement over prior art bed data systems in which transmission of audio data was not possible.

If power cord 240 is unplugged, loop antenna 256 no longer provides the first module ID to communication circuit 248 and communication circuit 248 notifies wall BT module 236 to break its pairing with module 232 of bed 20. During the communication between module 232, 236, module 236 operates as a "master" module such as by controlling the frequency hopping channels over which communications with module 232 occur, and module 232, therefore, operates as a "slave."

If modules 232, 234 are both present on bed 20, then in response to power cord 240 being plugged in, loop antenna 256 is powered up by communication circuit 248 and reads the first module ID and the second module ID from transponder 238 to communication circuit 248. Communication circuit then provides the first module ID and the second module ID to wall BT module 236. Module 236, acting as a "master," assesses the signal strength of the communications from modules 232, 234 and chooses to communicate with the "slave" (i.e., one or the other of modules 232, 234) that has lower RF interference based on received signal strength indicator (rssi) and channel map. If communication with the chosen slave is lost at any time after the master-slave relationship between module 236 and one of modules 232, 234 is established, module 236 jumps or switches the communication over to the other of modules 232, 234 if the RF interference with the other of modules 232, 234 is acceptable. In some embodiments, if the master module 236 is unable to communicate with both slave modules 232, 234, then at least one of modules 232, 234, 236 triggers an audible and/or visual alarm.

In the illustrative embodiment, module 232 is on one side of bed 20 and module 234 is on the other side of bed 20. For example, module 232 is coupled to a right siderail of bed 20 and module 234 is coupled to a left siderail of bed 20 in some embodiments. It is contemplated by this disclosure that bed 20 may include an additional Wi-Fi module such as, for example, modules 150, 150' discussed above. It is preferable to place the Wi-Fi module on bed 20 as far from modules 232, 234 as possible since Wi-Fi operates in in the same frequency band as Bluetooth. However, placing the additional Wi-Fi module at the head end of bed 20 between modules 232, 234 at the sides of bed 20 is sufficient. It is contemplated by this disclosure that the first and second BT modules 232, 234 communicate in different time slots than the additional Wi-Fi module communicates. Thus, when either of the modules 232, 234 are turned on, the additional Wi-Fi module is turned off and vice versa. Thus, the time slots of transmission are non-overlapping time slots.

Figure 21:
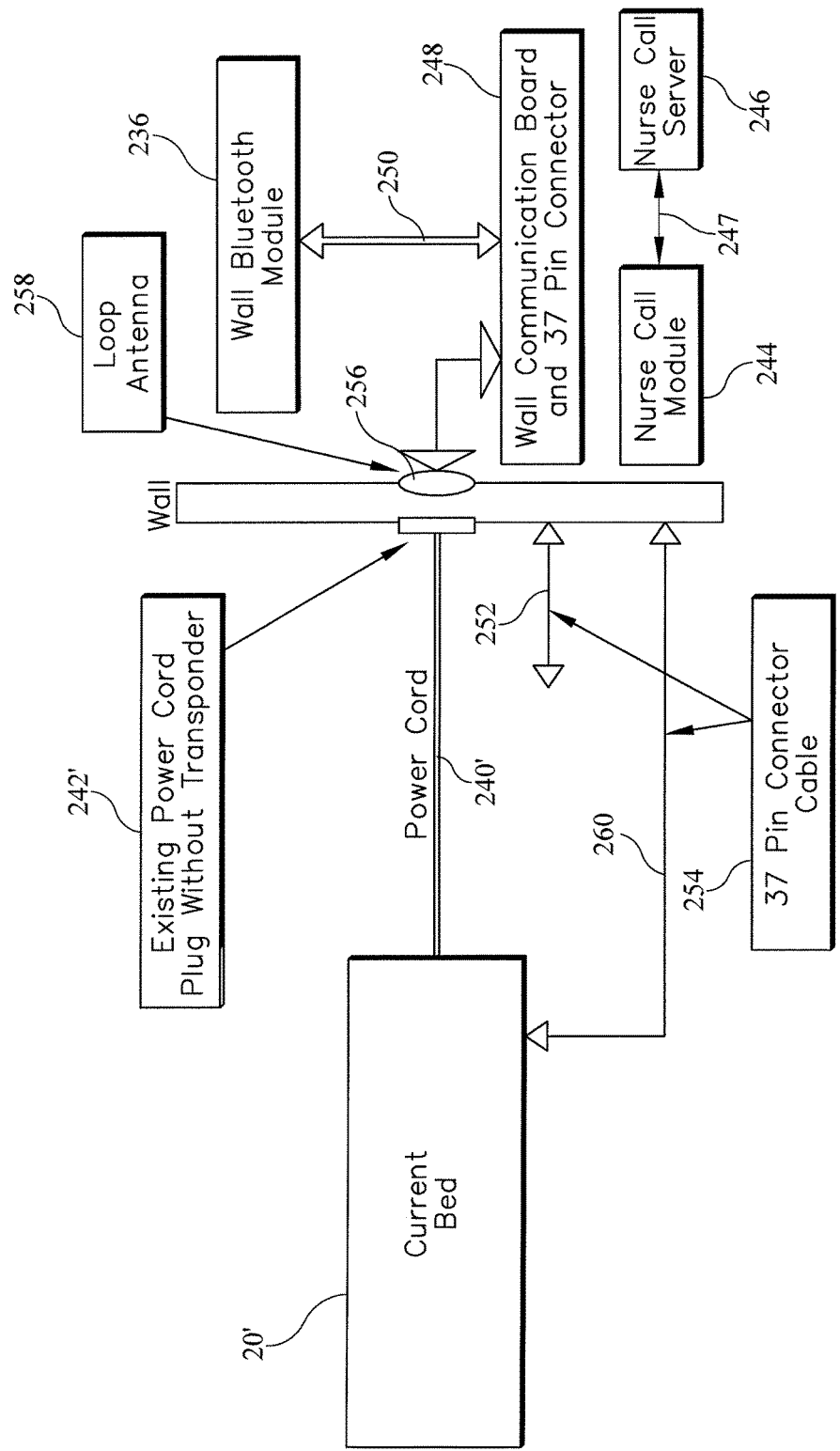
FIG. 21 is a block diagram showing a prior art bed that lacks any BT modules still being usable with the system of FIG. 20.

Referring now to FIG. 21, the scenario is illustrated in which a prior art bed 20' that lacks any wireless modules, such as modules 232, 234, is still able to be used with the system of FIG. 20. In this situation, bed 20' has a power cord 240' that does not have any transponder as indicated at diagrammatic block 242'. Instead, a traditional connector nurse call connector cable 260 is provided to provide a wired communication link between bed 20' and nurse call module 244. In the FIG. 21 example, it is contemplated that nurse call module 244 has only one nurse call cable connection port, such as a single 37-pin connection port. Thus, connector cable 252 is shown in FIG. 21 as being unplugged from the nurse call module 244 so that connector cable 260 can be plugged into the nurse call module 244. In some embodiments, nurse call module 244 is a Bed Interface Unit (BIU) that is marketed by Hill-Rom Company, Inc. of Batesville, Ind. In the FIG. 21 example, module 236, communication circuit 248, and loop antenna 256 are dormant, at least with regard to communication of bed data from bed 20' to and from nurse call server 246.

Figure 22:
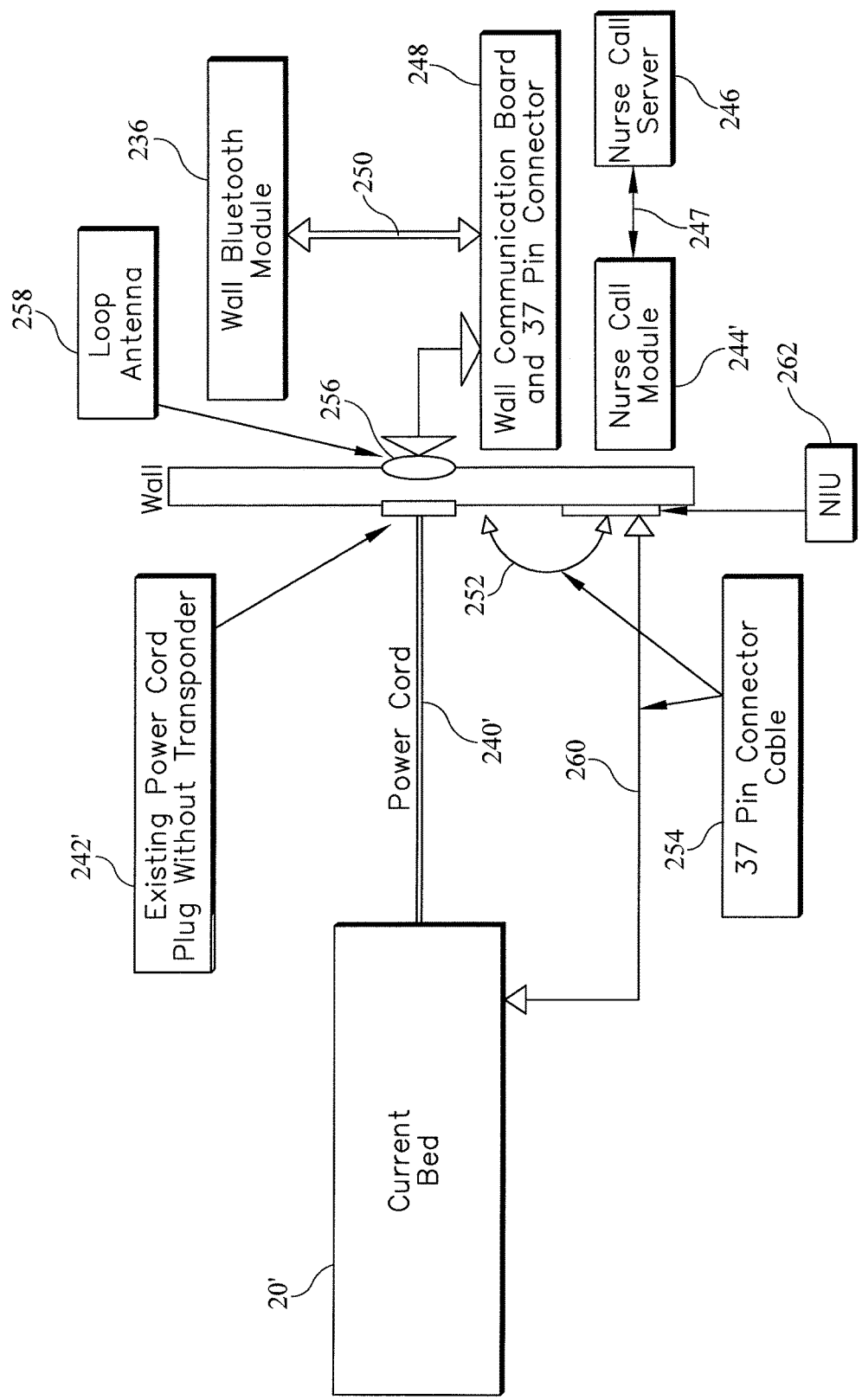
FIG. 22 is a block diagram similar to FIG. 21 but having a network interface unit (NIU) with two 37-pin cable connection ports so that a cable from a wall communication board remains plugged into one of the ports of the NIU even when a prior art bed has its 37-pin cable plugged into the other port of the NIU.

Referring now to FIG. 22, the scenario is illustrated in which a nurse call module 244' has two nurse call cable connection ports, such has having two 37-pin cable connection ports. An example of such a nurse call module 244' is a Network Interface Unit (NIU) which is indicated at diagrammatic block 262 in FIG. 22 and which is marketed by Hill-Rom Company, Inc. of Batesville, Ind. So, in the FIG. 22 example, cable 252 remains plugged into one of the connection ports of nurse communication module 244' even when the prior art bed 20' has its nurse call cable 260 plugged into the other of the connection ports of nurse call module 244'. In this situation, circuitry in nurse call module 244' operates so that the wired communication link between bed 20' and nurse call module 244' via cable 260 takes priority over the wired communication link between communication circuit 248 and nurse call module 244' via cable 252. In some embodiments, one of the connection ports of module 244' is a male 37-pin connector and the other of the connection ports of module 244' is a female 37-pin connector. The mating connectors at the ends of cables 252, 260 are fashioned accordingly.

Figure 23:
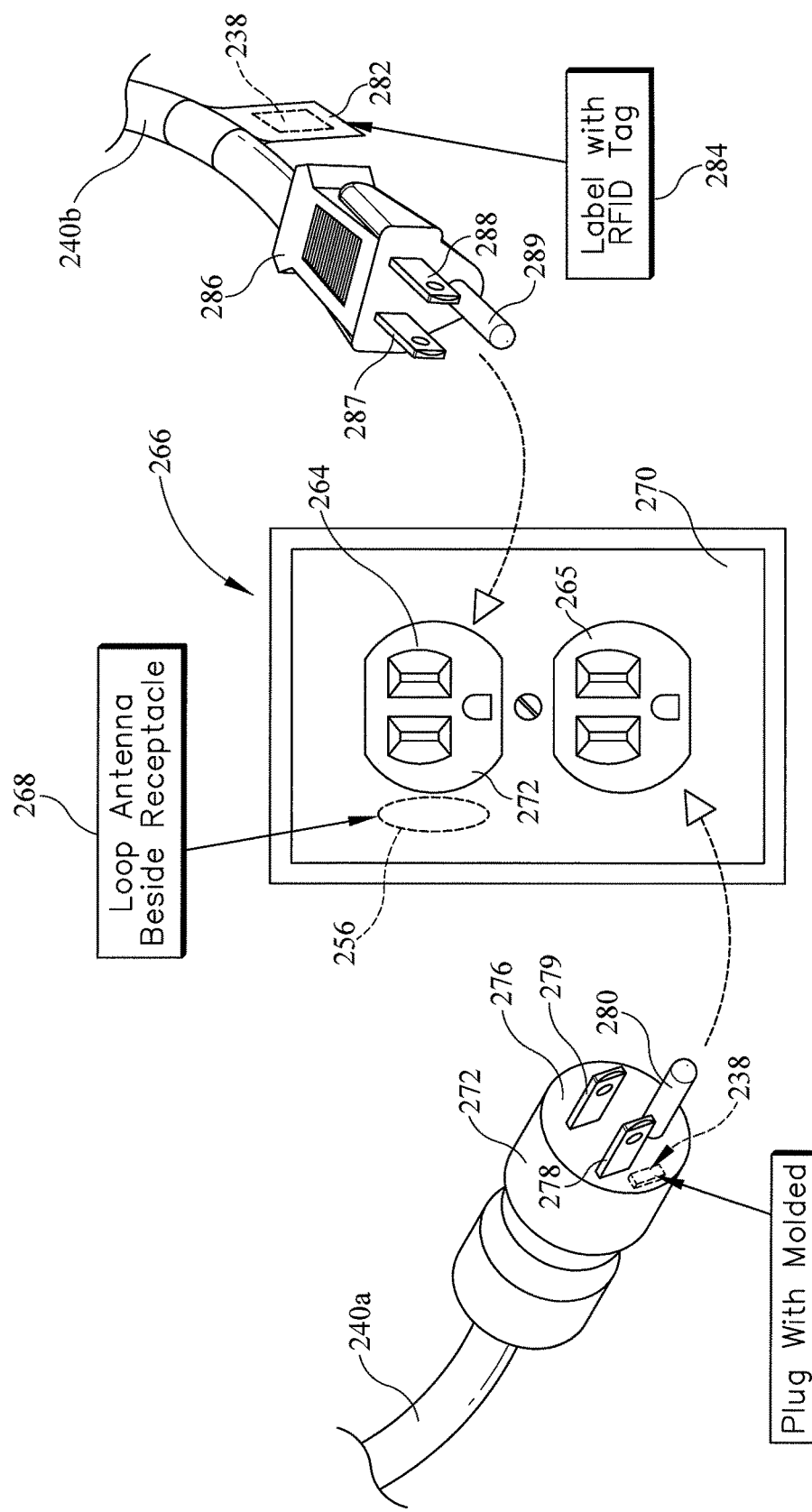
FIG. 23 is a perspective view showing a first AC power cord having an RFID tag molded into a plug body and showing a second AC power cord having an RFID tag included in a label that attaches to a cord portion adjacent a plug body.

Referring now to FIG. 23, loop antenna 256 of FIGS. 20-22 is shown situated beside a receptacle 264 of a duplex AC outlet 266 as indicated with diagrammatic block 268. For example, antenna 256 is mounted to a back surface of a duplex cover plate 270 adjacent the aperture 272 in cover plate 270 that receives receptacle 264. A first AC power cord 240a has its transponder 238 embodied as an RFID tag that is molded into a plug body 272 as indicated at diagrammatic block 274. Transponder 238 in plug body 272 is located closely behind a front surface 276 from which power prongs 278, 279 and ground prong 280 extend. When prongs 278, 279, 280 are received in a receptacle 265 of duplex AC outlet 266, transponder 238 of plug body 272 is sufficiently close to loop antenna 256 for wireless communication to be established therebetween. Of course, prongs 278, 279, 280 may also be received in receptacle 264, if desired, and antenna 256 and transponder 238 will communicate just as well. In the illustrative example, cord 240a and plug body 272 meet NEMA 5-15 hospital grade requirements.

A second AC power cord 240b has its transponder 238 embodied as an RFID tag included in a label 282 as indicated at diagrammatic block 284 in FIG. 23. Label 282 attaches to cord 240b at a position spaced from, but adjacent to, a plug body 286. Power prongs 287, 288 and a ground prong 289 extend from plug body 286. When prongs 297, 288, 289 are received in receptacle 264 (or receptacle 265, if desired) of duplex outlet 266, transponder 238 of label 282 is sufficiently close to loop antenna 256 for wireless communication to be established therebetween.

Active and passive transponders 238 (e.g., RFID tags) are contemplated by this disclosure. For example, transponder 238 of label 282 is a passive transponder whereas transponder 238 of plug body 272 is an active transponder that is powered by a 5 Volt (V) or 3.3 V power supply of bed 20. As shown in FIG. 25, power cord 240a contains AC power conductors 290, 292, a ground conductor 294, and DC power/data conductors 296, 298. Conductors 290, 292, 294 are coupled to prongs 278, 279, 280, respectively, and conductors 296, 298 are coupled to transponder 238 in plug body 272. Thus, conductors 296, 298 provided the power to transponder 238 and are also usable as data lines to program the first and second module ID's into memory of transponder 238.

In some embodiments, transponder 238 is an RFID tag having an EEPROM which is programmed by bed circuitry 22, such as by using a multipoint control unit (MCU), via a serial peripheral interface (SPI) protocol or Inter-Integrated Circuit (I2C) protocol. For the passive transponder 238, the first and second module ID's are written to memory wirelessly. In some embodiments contemplated by this disclosure, transponders 238 are programmed in an active mode, such as via conductors 296, 298, and then operate in a passive mode when loop antenna 256 is reading the module ID's from the transponder 238. In such embodiments, loop antenna 256 is energized by communication circuit 248 and transfers energy to transponder 238 that is used by the transponder to transmit the first and second module ID's fro reception by antenna 256.

Figure 24:
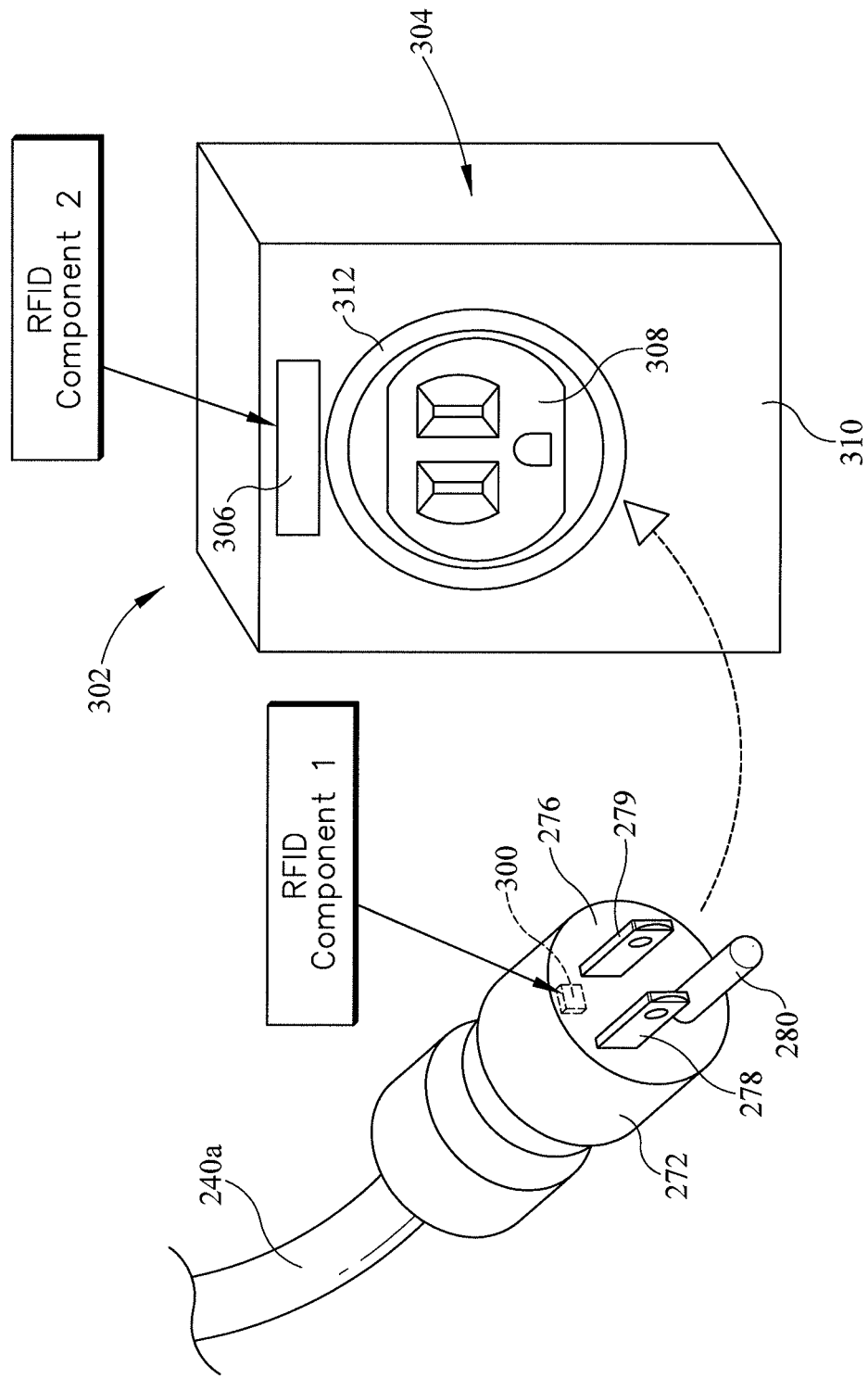
FIG. 24 is a perspective view showing an AC cord having a plug that carries a first RFID component and a receptacle module having a second RFID component, a light-up ring is provided around a receptacle of the receptacle module and is illuminated when a successful bed-to-room association has been made.

Referring now to FIG. 24, AC power cord 240a carries a first RFID component 300 in plug body 272 and a receptacle module 302 has a housing 304 that carries a second RFID component 306. Module 302 has an AC receptacle 308 at a front face 310 thereof. In some embodiments, module 302 plugs into an existing AC outlet and so power and ground prongs (not shown) extend from a back of housing 304 in such embodiments. In other embodiments, receptacle is wired directly to the power grid of the corresponding healthcare facility. Module 302 also has a light-up ring 312 that is provided at front face 310 and that circumscribes or encompasses receptacle 312. Light-up ring 312 is illuminated when a successful bed-to-room association has been made.

In a first scenario for determining a successful bed-to-room association, RFID component 306 includes a reader that receives bed ID data from RFID component 300 when power cord 240a is plugged in with prongs 278, 279, 280 being received by receptacle 308 of module 302. After RFID component 306 receives the bed ID data from RFID component 300, module 302 sends room ID data to the circuitry 22 of the bed 20 that is designated with the bed ID data using wireless transmission circuitry included in module 302. In some embodiments, the wireless communication circuitry of module 302 operates according to the Bluetooth protocol. In such embodiments, bed 20 includes Bluetooth circuitry. Bed 20 receives the room ID data and then transmits the bed ID data and the room ID data using a Wi-Fi transmitter of circuitry 22. Bed 20 also transmits a Bluetooth message back to the circuitry of module 302 to confirm the bed-to-room association. In response to that message, module illuminates light-up ring 312. Ring 312 is illuminated green in some embodiments.

In a second scenario for determining a successful bed-to-room association, RFID component 306 includes a passive RFID tag and RFID component 300 comprises a reader that receives power from conductors 296, 298 of cord 240a. RFID component 300 senses RFID component 306 when cord 240a is plugged into module 302 and reads room ID data that is encoded in RFID component 306. RFID component 300 then sends the room ID data to circuitry 22 of bed 20 via wired connection, such as one or both of conductors 296, 298. Bed 20 then transmits the bed ID data and the room ID data using a Wi-Fi transmitter of circuitry 22. In this scenario, module 302 receives a Wi-Fi signal or other wireless signal once a successful bed-to-room association is made (either at bed 20 or at a remote computer device, such as servers 26a, 26b) and the circuitry of module 302 turns on the light-up ring 312 to indicate the successful bed-to-room association.

Referring now to FIG. 26, another bed-to-room association system according to this disclosure is shown in which bed 20 has wireless transceiver, such as an illustrative Bluetooth transceiver 150", coupled to circuitry 22 and operable to establish wireless communications with circuitry 314 of a handheld pillow speaker unit 320 as indicated by diagrammatic dashed arrow 316. In this embodiment, the pillow speaker unit 320 acts as a communication intermediary between the bed 20 and a nurse call system 322 as well as one or more other remote computer devices 324. Bed data, including bed status data and bed ID data, is communicated to unit 320 wirelessly from bed 20 for reception by an antenna or transceiver 315 of circuitry 314 and, in turn, circuitry 314 of unit 320 sends the bed data to nurse call system 322 along with pillow speaker unit ID data. A computer device of nurse call system 322 and/or one of the other computer devices 324 includes a database that correlates the pillow speaker unit ID data with a patient room 326 in which unit 320, and therefore, bed 20 is located.

Pillow speaker unit 320 is coupled via a wired power and data connection to a nurse call interface 330 as indicated by diagrammatic double headed arrow 328. Nurse call interface 330 is coupled to nurse call system 322 as indicated by diagrammatic double headed arrow 332. Nurse call interface 330 is also coupled to a television (TV) 334, room lights 336, and window shades 338 as indicated by diagrammatic arrows 340, 342, 344, respectively. Pillow speaker unit 320 has user inputs 350 that are used to control functions of TV 334, lights 336, shades 338, and bed 20. Bed 20 has user inputs 352 that are also used to control functions of TV 334, lights 336, shades 338, and bed 20. Thus, when user inputs 350 of unit 320 are used to control bed 20, control signals from unit 320 are communicated to transceiver 150" wirelessly from circuitry 314 of unit 320. Similarly, when user inputs 352 of bed 20 are used to control TV 334, 336, 338, control signals from bed 20 are communicated from transceiver 150" wirelessly to circuitry 314 of unit 320. A pairing operation, such as the pairing operation described above in connection with FIG. 20, takes place between the circuitry 314 of unit 320 and the circuitry of bed 20 so that other, unrelated wireless transmissions are ignored by unit 320 and bed 20.

Figure 27:
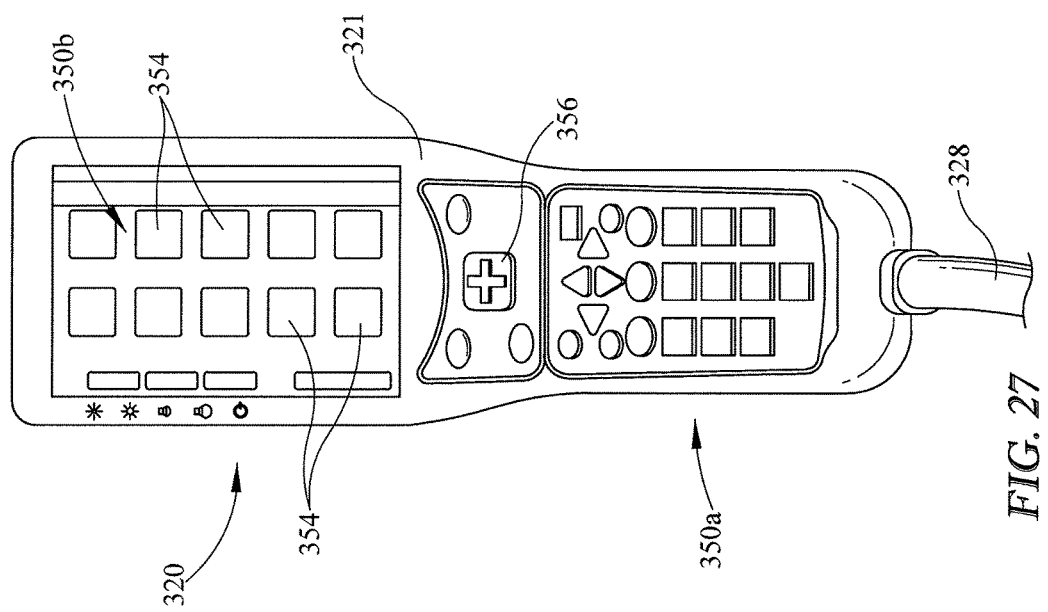
FIG. 27 is a front elevation view of a first embodiment of a handheld pillow speaker unit showing the pillow speaker unit having a graphical user interface (GUI) with touchscreen buttons and a number of manual buttons beneath the GUI.

Referring now to FIG. 27, a first embodiment of handheld pillow speaker unit 320 is shown in which a housing 321 carries a set of manual buttons 350a and a graphical user interface (GUI) 350b having electronic touchscreen buttons 354. The manual buttons 350a are located beneath the GUI 350b in the illustrative example. Known prior art pillow speaker units only have manual buttons. Thus, by equipping unit 320 with GUI 350b, unit 320 is able to have more sophisticated functionality than known pillow speaker units. However, pillow speaker unit 320 includes a manual nurse call button 356 which is pressed to send a general nurse call signal to nurse call system 322 in order to contact or summon an assigned caregiver. Others of the manual buttons are used to place telephone calls, to control TV 334, to control a radio, and to control room lights 336 and shades 338 in some embodiments.

In some embodiments, the touchscreen buttons 354 of GUI 350b have the functionality described in U.S. application Ser. No. 14/177,851, which was filed Feb. 11, 2014, which is titled "Workflow Canvas for Clinical Applications," and which is hereby incorporated by reference herein to the extent not inconsistent with the present disclosure which shall control as to any inconsistencies. In general, each button 354 is selected to send a specific message to an assigned caregiver. Such messages, for example, indicate that the patient needs to go to the bathroom, that the patient wants water, that the patient is in pain, that there is a problem with an intravenous (IV) pump or liquid, that there is a problem with a catheter, or that there is a problem with other equipment, such as bed 20. This list of messages is not intended to be exhaustive but merely to give a few examples. GUI 350b also permits a user to navigate to screens for controlling bed functions in some embodiments.

Figure 28:
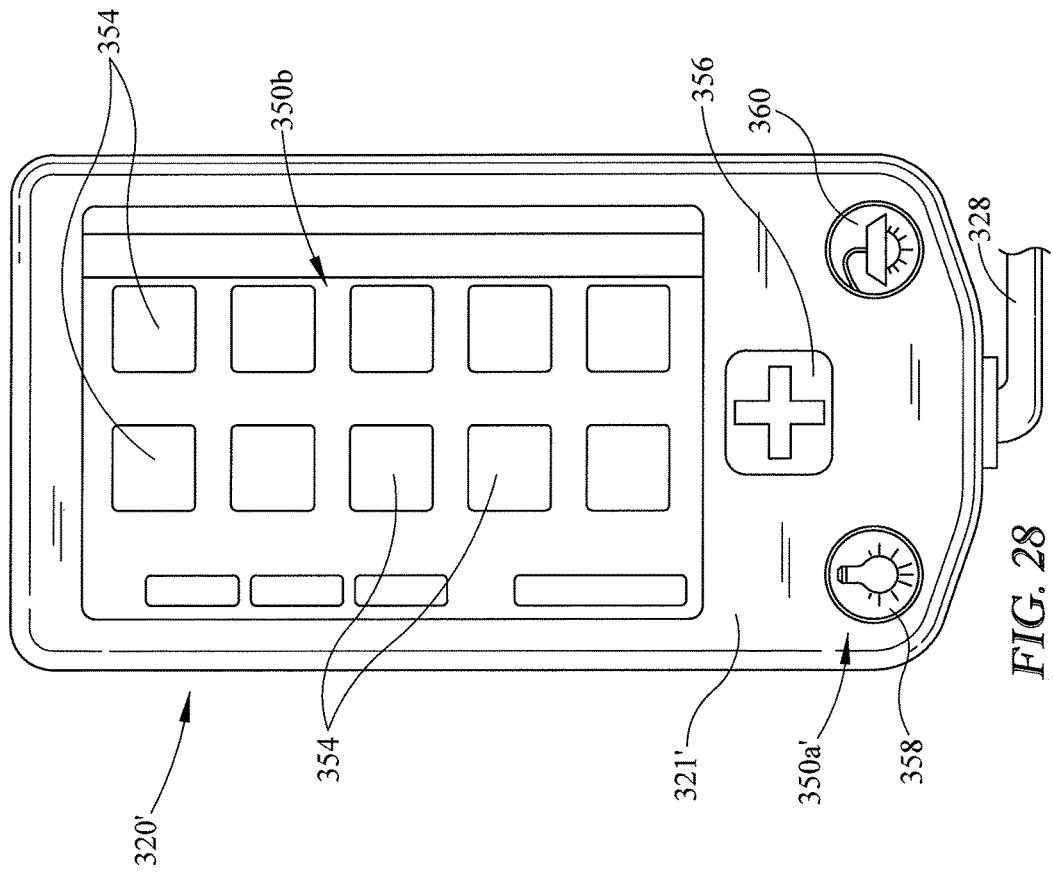
FIG. 28 is a front elevation view of a second embodiment of a handheld pillow speaker unit showing the pillow speaker unit having a GUI with touchscreen buttons, a manual nurse call button beneath the GUI, a first on/off button for control of a first light, and a second on/off button for control of a second light.

Referring now to FIG. 28, is a second embodiment of a handheld pillow speaker unit 320' is shown in which a housing 321' carries a reduced set of manual buttons 350a' but still has GUI 350b with electronic touchscreen buttons 354. The reduced set of manual buttons includes manual nurse call button 356 beneath the GUI 350b, a first on/off button 358 for control of a first light, and a second on/off button 360 for control of a second light. For example, the first light is one of room lights 336 and the second light is a reading light of bed 20 in some embodiments.

It will be appreciated that units 320, 320' of FIGS. 27 and 28 have traditional manual buttons 350a, 350b that older patients may be more comfortable using and also have GUI 350b that is similar to modern day smart phones that younger patients may be more comfortable using. However, because units 320, 320' are tethered to nurse call interface 330 by wired connection 328, units 320, 320' will not become lost or misplaced by patients as may tend to occur if units 320, 320' were wireless units. The enhanced functionality afforded to units 320, 320' by GUI 350b allows for a better patient experience due to more effective communications between the patient and the caregiving staff of the healthcare facility.

Each of the embodiments disclosed herein can have features of one or more of each of the other embodiments. For example, the patient-to-bed association system of FIG. 19 in which a patient wears a device that transmits data that corresponds to patient ID can be used in combination with the various embodiments of FIGS. 1-18 and 20-28. Furthermore, it is contemplated that a system can employ different bed-to-room association embodiments in different patient rooms. Thus, one room of a healthcare facility may have the embodiment of FIG. 1 or 2 (location data encoded in light), another room in the healthcare facility may have the embodiment of FIG. 3 or 4 (bar code array), another room in the healthcare facility may have the embodiment of FIGS. 5-10 (manual location entry), and so on. Thus, a system employing, at the same time, each and every embodiment disclosed herein is within the scope of this disclosure.

Although certain illustrative embodiments have been described in detail above, variations and modifications exist within the scope and spirit of this disclosure as described and as defined in the following claims.

The invention claimed is:
1. A system for associating a bed to a room of a healthcare facility, the system comprising
   a locator unit that is fixed in place in the room and that transmits a location ID,
   a patient bed having first circuitry that has a first ID and that receives the location ID, the patient bed having second circuitry that is independent of the first circuitry, the second circuitry being configured to transmit a bed ID and bed status data,
   a first transceiver spaced from the locator unit and spaced from the patient bed, the first transceiver receiving the first ID and location ID transmitted by the first circuitry,
   a second transceiver that is spaced from and independent of the first transceiver, the second transceiver receiving the bed ID and the bed status data transmitted by the second circuitry,
   a first remote computer device receiving the location ID and first ID transmitted to the first remote computer device by the first transceiver, and
   a second remote computer device that receives the bed ID and the bed status data which is transmitted to the second computer device by the second transceiver, wherein the first and second remote computer devices cooperate to associate the location ID and the bed status data with the bed ID, wherein the patient bed includes an indicator coupled to the second circuitry and that is signaled by the second circuitry to provide an indication that a successful bed-to-room association has been made.

2. The system of claim 1, wherein the first circuitry is included as part of a tag that attaches to an exterior surface of the patient bed.

3. The system of claim 1, wherein the first circuitry transmits the first ID and the location ID using a first wireless transmission technology, the second circuitry transmits the bed ID and the bed status data using a second wireless transmission technology, and the first wireless transmission technology differs from the second wireless transmission technology.

4. The system of claim 3, wherein the first wireless transmission technology comprises one of infrared technology, radio frequency technology, and ultrasonic technology and the second wireless transmission technology comprises a different one of infrared technology, radio frequency technology, and ultrasonic technology.

5. The system of claim 1, wherein the indicator is turned on in response to the successful bed-to-room association being made and the indicator being turned off in the absence of the successful bed-to-room association.

6. The system of claim 1, wherein the indicator is illuminated a first color in response to the successful bed-to-room association being made and the indicator being illuminated a second color in the absence of the successful bed-to-room association.

7. The system of claim 1, wherein the indication that the successful bed-to-room association has been made is communicated to the second circuitry from the first remote computer device or the second remote computer device.

8. The system of claim 1, wherein the patient bed includes at least one other indicator that includes a communication indicator to indicate that a successful communication link has been established with the second remote computer device via the second transceiver.

9. The system of claim 1, wherein the patient bed includes at least one other indicator that includes an alarm monitor indicator to indicate that one or more conditions of the patient bed have been selected using the second remote computer for monitoring of alarm conditions.

10. The system of claim 1, wherein the patient bed includes at least one other indicator that includes a signal strength indicator that indicates a strength of a wireless communication link with the second transceiver.

11. The system of claim 1, wherein the second circuitry is only notified of the successful bed-to-room association if the bed status data includes information indicating that a power cord of the patient bed is plugged into a power outlet in the room.

12. The system of claim 1, wherein the patient bed includes a graphical display that is coupled to the second circuitry and that is signaled by the second circuitry to display location information on the graphical display as an indication that a successful bed-to-room association has been made.

13. The system of claim 1, wherein the first circuitry receives the location ID via infrared (IR) communication.

14. The system of claim 1, wherein the first circuitry transmits the location ID and the first ID using radio frequency (RF) communication.

15. The system of claim 1, wherein the second circuitry communicates wireless using Wi-Fi communication.

16. The system of claim 1, further comprising a second patient bed and association means for associating the second patient bed to a second room of the healthcare facility.

17. The system of claim 13, wherein the association means comprises at least one or more of the following:
   (i) a light source that emits visible light having a signature that is unique to a location of the healthcare facility;
   (ii) an array of redundant bar codes and a bar code reader that is coupled to the second patient bed and that reads at least one of the redundant bar codes in the array;
   (iii) a graphical user interface that is coupled to the second patient bed and that displays at least one user interface screen that is used by a caregiver to manually enter location data indicative of a location in a healthcare facility occupied by the second patient bed;
   (iv) third circuitry coupled to the second patient bed and having stored therein ID translation software, the third circuitry receiving a second room location ID in a first format and, in accordance with the ID translation software, converting the second room location ID to a modified ID having a second format different than the first format, the third circuitry transmitting the modified ID;
   (v) fourth circuitry coupled to the second patient bed and having stored therein ID mutation software, the fourth circuitry receiving the second location ID and, in accordance with the ID mutation software, mutating the second location ID and a second bed ID of the second bed into a mutated ID, the mutated ID being a single unique ID, the fourth circuitry transmitting the mutated ID;
   (vi) at least one bed Bluetooth (BT) module coupled to the second patient bed and in communication with a wall BT module for transmission of bed data after a BT pairing operation is conducted based on transmission of bed BT module ID data via a transponder carried by a plug of a power cord of the second patient bed;
   (vii) a power cord of the second patient bed carrying a first RFID component, and a receptacle module carrying a second RFID component, the receptacle module having a receptacle into which the power cord plugs to receive power and to bring the first and second RFID components into communicative proximity, the receptacle module having an indicator that is activated in response to successful communication being established between the first and second RFID components.

18. The system of claim 1, further comprising an apparatus for communicating with a nurse call system of the healthcare facility, the apparatus comprising a second patient bed configured for wireless communication of second bed identification (ID) data and second bed status data, and a handheld pillow speaker unit having a pillow speaker transceiver in wireless communication with the second patient bed, the pillow speaker unit being in hardwired communication with the nurse call system, wherein the pillow speaker unit serves as a communication intermediary between the second patient bed and the nurse call system.

19. The system of claim 1, further comprising a pillow speaker unit to communicate with a nurse call system of the healthcare facility, the pillow speaker unit comprising a handheld housing, a set of manual buttons accessible on the housing, and a touchscreen graphical display that displays electronic buttons, at least one of the manual buttons and at least one of the electronic buttons being usable to send a respective signal to the nurse call system.

* * * * *